(12) United States Patent
Rao et al.

(10) Patent No.: US 12,241,080 B2
(45) Date of Patent: Mar. 4, 2025

(54) BACTERIOPHAGE-BASED ARTIFICIAL VIRUSES FOR HUMAN GENOME REMODELING

(71) Applicant: The Catholic University of America, Washington, DC (US)

(72) Inventors: Venigalla B. Rao, Washington, DC (US); Jingen Zhu, Washington, DC (US)

(73) Assignee: The Catholic University of America, Washington, DC (US)

(*) Notice: Subject to any disclaimer, the term of this patent is extended or adjusted under 35 U.S.C. 154(b) by 660 days.

(21) Appl. No.: 17/546,183

(22) Filed: Dec. 9, 2021

(65) Prior Publication Data

US 2022/0090139 A1 Mar. 24, 2022

Related U.S. Application Data

(60) Division of application No. 17/359,711, filed on Jun. 28, 2021, now Pat. No. 11,401,530, which is a continuation-in-part of application No. 16/990,289, filed on Aug. 11, 2020, now Pat. No. 11,155,835.

(60) Provisional application No. 62/888,576, filed on Aug. 19, 2019, provisional application No. 63/058,012, filed on Jul. 29, 2020.

(51) Int. Cl.
C12N 15/86 (2006.01)
C12N 7/00 (2006.01)

(52) U.S. Cl.
CPC ............... *C12N 15/86* (2013.01); *C12N 7/00* (2013.01); *C12N 2795/00043* (2013.01); *C12N 2795/00051* (2013.01)

(58) Field of Classification Search
None
See application file for complete search history.

(56) References Cited

U.S. PATENT DOCUMENTS

| | | | | |
|---|---|---|---|---|
| 8,148,130 | B2 * | 4/2012 | Alving ................. | C07K 14/005 435/235.1 |
| 8,685,694 | B2 * | 4/2014 | Rao ....................... | A61K 39/295 435/235.1 |
| 11,155,835 | B2 * | 10/2021 | Rao ....................... | C12N 15/86 |
| 11,401,530 | B2 * | 8/2022 | Rao ....................... | C12N 15/102 |
| 2006/0035364 | A1 | 2/2006 | Wright et al. | |
| 2009/0226525 | A1 | 9/2009 | de los Rios et al. | |
| 2011/0111459 | A1 | 5/2011 | Boyce | |
| 2019/0330643 | A1 | 10/2019 | Rao et al. | |

FOREIGN PATENT DOCUMENTS

| | | |
|---|---|---|
| WO | 99/63348 A1 | 6/1999 |
| WO | 03/040720 A1 | 5/2003 |
| WO | 2014/135998 A1 | 9/2014 |
| WO | 2018/035387 A1 | 2/2018 |
| WO | 2018/191750 A2 | 10/2018 |
| WO | 2019/169159 A1 | 9/2019 |

OTHER PUBLICATIONS

Kabadi, et al. (2014) "Multiplex CRISPR/Cas9-based genome engineering from a single lentiviral vector", Nucleic Acids Research, 42(19): e147, 11 pages. (Year: 2014).*
Tao, P., Mahalingam, M., Marasa, B.S., Zhang, Z., Chopra, A.K., and Rao, V.B. (2013). In vitro and in vivo delivery of genes and proteins using the bacteriophage T4 DNA packaging machine. Proceedings of the National Academy of Sciences of the United States of America 110, 5846-5851.
Tao, P., Wu, X., and Rao, V. (2018a). Unexpected evolutionary benefit to phages imparted by bacterial CRISPR-Cas9. Science Advances 4, eaar4134.
Tao, P., Wu, X., Tang, W.C., Zhu, J., and Rao, V. (2017). Engineering of Bacteriophage T4 Genome Using CRISPR-Cas9. ACS Synthetic Biology 6, 1952-1961.
Tao, P., Zhu, J., Mahalingam, M., Batra, H., and Rao, V.B. (2018b). Bacteriophage T4 nanoparticles for vaccine delivery against infectious diseases. Advanced Drug Delivery Reviews.
Torchilin, V.P., Rammohan, R., Weissig, V., and Levchenko, T.S. (2001). TAT peptide on the surface of liposomes affords their efficient intracellular delivery even at low temperature and in the presence of metabolic inhibitors. Proceedings of the National Academy of Sciences of the United States of America 98, 8786-8791.
Vafabakhsh, R., Kondabagil, K., Earnest, T., Lee, K.S., Zhang, Z., Dai, L., Dahmen, K.A., Rao, V.B., and Ha, T. (2014). Single-molecule packaging initiation in real time by a viral DNA packaging machine from bacteriophage T4. Proceedings of the National Academy of Sciences of the United States of America 111, 15096-15101.
Van Meer, G., Voelker, D.R., and Feigenson, G.W. (2008). Membrane lipids: where they are and how they behave. Nature Reviews Molecular Cell Biology 9, 112-124.
Wang, M., Zuris, J.A., Meng, F., Rees, H., Sun, S., Deng, P., Han, Y., Gao, X., Pouli, D., Wu, Q., et al. (2016). Efficient delivery of genome-editing proteins using bioreducible lipid nanoparticles. Proceedings of the National Academy of Sciences of the United States of America.
Wu, F., Zhao, S., Yu, B., Chen, Y.M., Wang, W., Song, Z.G., Hu, Y., Tao, Z.W., Tian, J.H., Pei, Y.Y., et al. (2020). A new coronavirus associated with human respiratory disease in China. Nature 579, 265-269.

(Continued)

*Primary Examiner* — Robert M Kelly
(74) *Attorney, Agent, or Firm* — Ajay A. Jagtiani; Miles & Stockbridge P.C.

(57) ABSTRACT

Described is an "artificial virus" (AV) programmed with biomolecules that can enter human cells and carry out precise human genome modification. The AVs comprise: at least one viral vector, such as bacteriophage T4; at least one therapeutic molecule, such as DNA, RNA, protein and their complex; and a lipid coating. Also described is a method of human genome modification, using such an AV, and a method of program such an AV.

6 Claims, 53 Drawing Sheets
(52 of 53 Drawing Sheet(s) Filed in Color)
Specification includes a Sequence Listing.

(56) References Cited

OTHER PUBLICATIONS

Yap, M.L., and Rossmann, M.G. (2014). Structure and function of bacteriophage T4. Future Microbiology 9, 1319-1327.
Yin, H., Kanasty, R.L., Eltoukhy, A.A., Vegas, A.J., Dorkin, J.R., and Anderson, D.G. (2014). Non-viral vectors for gene-based therapy. Nature Reviews Genetics 15, 541-555.
Yin, H., Kauffman, K.J., and Anderson, D.G. (2017). Delivery technologies for genome editing. Nature Reviews Drug Discovery 16, 387-399.
Zhang, Z., Kottadiel, V.I., Vafabakhsh, R., Dai, L., Chemla, Y.R., Ha, T., and Rao, V.B. (2011). A promiscuous DNA packaging machine from bacteriophage T4. PLoS Biology 9, e1000592.
Zhou, T., Georgiev, I., Wu, X., Yang, Z.Y., Dai, K., Finzi, A., Kwon, Y.D., Scheid, J.F., Shi, W., Xu, L., et al. (2010). Structural basis for broad and potent neutralization of HIV-1 by antibody VRC01. Science 329, 811-817.
Zhu, J., Tao, P., Mahalingam, M., Sha, J., Kilgore, P., Chopra, A.K., and Rao, V. (2019). A prokaryotic-eukaryotic hybrid viral vector for delivery of large cargos of genes and proteins into human cells. Science Advances 5, eaax0064.
Zuris, J.A., Thompson, D.B., Shu, Y., Guilinger, J.P., Bessen, J.L., Hu, J.H., Maeder, M.L., Joung, J.K., Chen, Z.Y., and Liu, D.R. (2015). Cationic lipid-mediated delivery of proteins enables efficient protein-based genome editing in vitro and in vivo. Nature Biotechnology 33, 73-80.
Black LW, Showe MK, Steven AC (1994) Morphogenesis of the T4 head. In: Karam JD (ed) Molecular biology of bacteriophage T4. American Society for Microbiology Press, Washington, DC, pp. 218-258.
International Search Report and Written Opinion received in PCT Application No. PCT/IB2021/056248 mailed Oct. 13, 2021.
Li et al., "Artifical Virus Delivers CRISPR-Cas9 System for Genome Editing of Cells in Mice", ACS Nano, pp. 1-58 (2016).
Wang et al., "Efficient delivery of genome-editing proteins using bioreducible lipid nanoparticles", PNAS, vol. 113, No. 11, pp. 2868-2873 (2016).
Zhang et al., "Lipid nanoparticle-mediated efficient delivery of CRISPR/Cas9 for tumor therapy", NPG Asia Materials, vol. 9, Article No. 441, pp. 1-8 (2017).
Barr, J.J., Auro, R., Furlan, M., Whiteson, K.L., Erb, M.L., Pogliano, J., Stotland, A., Wolkowicz, R., Cutting, A.S., Doran, K.S., et al. (2013). Bacteriophage adhering to mucus provide a non-host-derived immunity. Proceedings of the National Academy of Sciences of the United States of America 110, 10771-10776.
Behzadi, S., Serpooshan, V., Tao, W., Hamaly, M.A., Alkawareek, M.Y., Dreaden, E.C., Brown, D., Alkilany, A.M., Farokhzad, O.C., and Mahmoudi, M. (2017). Cellular uptake of nanoparticles: journey inside the cell. Chemical Society Reviews 46, 4218-4244.
Butler, K.V., Kalin, J., Brochier, C., Vistoli, G., Langley, B., and Kozikowski, A.P. (2010). Rational design and simple chemistry yield a superior, neuroprotective HDAC6 inhibitor, tubastatin A. Journal of the American Chemical Society 132, 10842-10846.
Casjens, S.R. (2011). The DNA-packaging nanomotor of tailed bacteriophages. Nature Reviews Microbiology 9, 647-657.
Chen, Z., Sun, L., Zhang, Z., Fokine, A., Padilla-Sanchez, V., Hanein, D., Jiang, W., Rossmann, M.G., and Rao, V.B. (2017). Cryo-EM structure of the bacteriophage T4 isometric head at 3.3—A resolution and its relevance to the assembly of icosahedral viruses. Proceedings of the National Academy of Sciences of the United States of America 114, E8184-E8193.
Cong, L., Ran, F.A., Cox, D., Lin, S., Barretto, R., Habib, N., Hsu, P.D., Wu, X., Jiang, W., Marraffini, L.A., et al. (2013). Multiplex genome engineering using CRISPR/Cas systems. Science 339, 819-823.
D'Astolfo, D.S., Pagliero, R.J., Pras, A., Karthaus, W.R., Clevers, H., Prasad, V., Lebbink, R.J., Rehmann, H., and Geijsen, N. (2015). Efficient intracellular delivery of native proteins. Cell 161, 674-690.
Danhier, F., Le Breton, A., and Preat, V. (2012). RGD-based strategies to target alpha(v) beta(3) integrin in cancer therapy and diagnosis. Molecular Pharmaceutics 9, 2961-2973.

De Beer, T., Fang, J., Ortega, M., Yang, Q., Maes, L., Duffy, C., Berton, N., Sippy, J., Overduin, M., Feiss, M., et al. (2002). Insights into specific DNA recognition during the assembly of a viral genome packaging machine. Molecular Cell 9, 981-991.
DeKelver, R.C., Choi, V.M., Moehle, E.A., Paschon, D.E., Hockemeyer, D., Meijsing, S.H., Sancak, Y., Cui, X., Steine, E.J., Miller, J.C., et al. (2010). Functional genomics, proteomics, and regulatory DNA analysis in isogenic settings using zinc finger nuclease-driven transgenesis into a safe harbor locus in the human genome. Genome Research 20, 1133-1142.
Dion, M.B., Oechslin, F., and Moineau, S. (2020). Phage diversity, genomics and phylogeny. Nature Reviews Microbiology 18, 125-138.
Doherty, G.J., and McMahon, H.T. (2009). Mechanisms of endocytosis. Annual Review of Biochemistry 78, 857-902.
Dong, Y., Siegwart, D.J., and Anderson, D.G. (2019). Strategies, design, and chemistry in siRNA delivery systems. Advanced Drug Delivery Reviews 144, 133-147.
Escors, D., and Breckpot, K. (2010). Lentiviral vectors in gene therapy: their current status and future potential. Archivum Immunologiae Et Therapiae Experimentalis 58, 107-119.
Fang, Q., Tang, W.C., Tao, P., Mahalingam, M., Fokine, A., Rossmann, M.G., and Rao, V.B. (2020). Structural morphing in a symmetry-mismatched viral vertex. Nature Communications 11, 1713.
Fokine, A., Chipman, P.R., Leiman, P.G., Mesyanzhinov, V.V., Rao, V.B., and Rossmann, M.G. (2004). Molecular architecture of the prolate head of bacteriophage T4. Proceedings of the National Academy of Sciences of the United States of America 101, 6003-6008.
Fokine, A., Islam, M.Z., Zhang, Z., Bowman, V.D., Rao, V.B., and Rossmann, M.G. (2011). Structure of the three N-terminal immunoglobulin domains of the highly immunogenic outer capsid protein from a T4-like bacteriophage. Journal of Virology 85, 8141-8148.
Fuller, D.N., Rickgauer, J.P., Jardine, P.J., Grimes, S., Anderson, D.L., and Smith, D.E. (2007). Ionic effects on viral DNA packaging and portal motor function in bacteriophage phi 29. Proceedings of the National Academy of Sciences of the United States of America 104, 11245-11250.
Gao, X., Tao, Y., Lamas, V., Huang, M., Yeh, W.H., Pan, B., Hu, Y.J., Hu, J.H., Thompson, D.B., Shu, Y., et al. (2018). Treatment of autosomal dominant hearing loss by in vivo delivery of genome editing agents. Nature 553, 217-221.
Hernandez-Garcia, A., Kraft, D.J., Janssen, A.F., Bomans, P.H., Sommerdijk, N.A., Thies-Weesie, D.M., Favretto, M. E., Brock, R., de Wolf, F.A., Werten, M.W., et al. (2014). Design and self-assembly of simple coat proteins for artificial viruses. Nature Nanotechnology 9, 698-702.
Ishii, T., and Yanagida, M. (1977). The two dispensable structural proteins (soc and hoc) of the T4 phage capsid; their purification and properties, isolation and characterization of the defective mutants, and their binding with the defective heads in vitro. Journal of Molecular Biology 109, 487-514.
Johnson, J.E., and Chiu, W. (2007). DNA packaging and delivery machines in tailed bacteriophages. Current Opinion In Structural Biology 17, 237-243.
Kim, Y.B., Zhao, K.T., Thompson, D.B., and Liu, D.R. (2019). An anionic human protein mediates cationic liposome delivery of genome editing proteins into mammalian cells. Nature Communications 10, 2905.
Kondabagil, K.R., Zhang, Z., and Rao, V.B. (2006). The DNA translocating ATPase of bacteriophage T4 packaging motor. Journal of Molecular Biology 363, 786-799.
Leffers, G., and Rao, V.B. (1996). A discontinuous headful packaging model for packaging less than headful length DNA molecules by bacteriophage T4. Journal of Molecular Biology 258, 839-850.
Leiman, P.G., Chipman, P.R., Kostyuchenko, V.A., Mesyanzhinov, V.V., and Rossmann, M.G. (2004). Three-dimensional rearrangement of proteins in the tail of bacteriophage T4 on infection of its host. Cell 118, 419-429.
Li, Q., Shivachandra, S.B., Zhang, Z., and Rao, V.B. (2007). Assembly of the small outer capsid protein, Soc, on bacteriophage

(56) References Cited

OTHER PUBLICATIONS

T4: a novel system for high density display of multiple large anthrax toxins and foreign proteins on phage capsid. Journal of Molecular Biology 370, 1006-1019.

Mali, P., Yang, L., Esvelt, K.M., Aach, J., Guell, M., DiCarlo, J.E., Norville, J.E., and Church, G.M. (2013). RNA-guided human genome engineering via Cas9. Science 339, 823-826.

Mastrobattista, E., van der Aa, M.A., Hennink, W.E., and Crommelin, D.J. (2006). Artificial viruses: a nanotechnological approach to gene delivery. Nature Reviews Drug Discovery 5, 115-121.

Meinke, G., Bohm, A., Hauber, J., Pisabarro, M.T., and Buchholz, F. (2016). Cre Recombinase and Other Tyrosine Recombinases. Chemical Reviews 116, 12785-12820.

Miller, E.S., Kutter, E., Mosig, G., Arisaka, F., Kunisawa, T., and Ruger, W. (2003). Bacteriophage T4 genome. Microbiology and Molecular Biology Reviews: MMBR 67, 86-156, table of contents.

Mullaney, J.M., and Black, L.W. (1996). Capsid targeting sequence targets foreign proteins into bacteriophage T4 and permits proteolytic processing. Journal of Molecular Biology 261, 372-385.

Muzyczka, R.J.S.a.N. (2014). AAV-Mediated Gene Therapy for Research and Therapeutic Purposes. Annual Review of Virology, 427-451.

Natarajan, P., Lander, G.C., Shepherd, C.M., Reddy, V.S., Brooks, C.L., 3rd, and Johnson, J.E. (2005). Exploring cosahedral virus structures with VIPER. Nature Reviews Microbiology 3, 809-817.

Nayerossadat, N., Maedeh, T., and Ali, P.A. (2012). Viral and nonviral delivery systems for gene delivery. Advanced Biomedical Research 1, 27.

Nelson, C.E., and Gersbach, C.A. (2016). Engineering Delivery Vehicles for Genome Editing. Annual Review of Chemical and Biomolecular Engineering 7, 637-662.

Ni, R., Zhou, J., Hossain, N., and Chau, Y. (2016). Virus-inspired nucleic acid delivery system: Linking virus and viral mimicry. Advanced Drug Delivery Reviews 106, 3-26.

Paez-Espino, D., Eloe-Fadrosh, E.A., Pavlopoulos, G.A., Thomas, A.D., Huntemann, M., Mikhailova, N., Rubin, E., Ivanova, N.N., and Kyrpides, N.C. (2016). Uncovering Earth's virome. Nature 536, 425-430.

Qin, L., Fokine, A., O'Donnell, E., Rao, V.B., and Rossmann, M.G. (2010). Structure of the small outer capsid protein, Soc: a clamp for stabilizing capsids of T4-like phages. Journal of Molecular Biology 395, 728-741.

Ran, F.A., Hsu, P.D., Wright, J., Agarwala, V., Scott, D.A., and Zhang, F. (2013). Genome engineering using the CRISPR-Cas9 system. Nature protocols 8, 2281-2308.

Rao, V.B., and Feiss, M. (2008). The bacteriophage DNA packaging motor. Annual Review of Genetics 42, 647-681.

Rao, V.B., and Feiss, M. (2015). Mechanisms of DNA Packaging by Large Double-Stranded DNA Viruses. Annu Rev Virol 2, 351-378.

Rao, V.B., Thaker, V., and Black, L.W. (1992). A phage T4 in vitro packaging system for cloning long DNA molecules. Gene 113, 25-33.

Rauch, B.J., Silvis, M.R., Hultquist, J.F., Waters, C.S., McGregor, M.J., Krogan, N.J., and Bondy-Denomy, J. (2017). Inhibition of CRISPR-Cas9 with Bacteriophage Proteins. Cell 168, 150-158 e110.

Robertson, K., Furukawa, Y., Underwood, A., Black, L., and Liu, J.L. (2012). Deletion of the Hoc and Soc capsid proteins affects the surface and cellular uptake properties of bacteriophage T4 derived nanoparticles. Biochemical and Biophysical Research Communications 418, 537-540.

Sahin, U., Kariko, K., and Tureci, O. (2014). mRNA-based therapeutics—developing a new class of drugs. Nature Reviews Drug Discovery 13, 759-780.

Shivachandra, S.B., Rao, M., Janosi, L., Sathaliyawala, T., Matyas, G.R., Alving, C.R., Leppla, S.H., and Rao, V.B. (2006). In vitro binding of anthrax protective antigen on bacteriophage T4 capsid surface through Hoc-capsid interactions: a strategy for efficient display of large full-length proteins. Virology 345, 190-198.

Stewart, M.P., Sharei, A., Ding, X., Sahay, G., Langer, R., and Jensen, K.F. (2016). In vitro and ex vivo strategies for Intracellular delivery. Nature 538, 183-192.
Sun, L., Zhang, X., Gao, S., Rao, P.A., Padilla-Sanchez, V., Chen, Z., Sun, S., Xiang, Y., Subramaniam, S., Rao, V.B., et al. (2015). Cryo-EM structure of the bacteriophage T4 portal protein assembly at near-atomic resolution. Nature Communications 6, 7548.
Sun, S., Kondabagil, K., Draper, B., Alam, T.I., Bowman, V.D., Zhang, Z., Hegde, S., Fokine, A., Rossmann, M.G., and Rao, V.B (2008). The structure of the phage T4 DNA packaging motor suggests a mechanism dependent on electrostatic forces. Cell 135, 1251-1262.
Karimi et al., "Bacteriophages and Phage-Inspired Nanocarriers for Targeted Delivery of Therapeutic Cargos", Adv. Drug. Deliv. Rev., pp. 45-62 (2016).
Pranjol et al., "Bacteriophage-Derived Vectors for Targeted Cancer Gene Therapy", Viruses, 7, pp. 268-284 (2015).
Official Action received in Canadian Application No. 3,148,369 dated May 11, 2023.
Official Action received in Chinese Application No. 202080065773.1 dated Mar. 15, 2023.
Extended European Search Report received in European Application No. 20855101.0 mailed Aug. 28, 2023.
Office Action received in Chinese Application No. 202080065773.1 issued Jul. 5, 2022.
Office Action received in Japanese Application No. 2022-510123 mailed Aug. 9, 2022.
Office Action received in Korean Application No. 10-2022-7008043 dated Aug. 22, 2022.
Karimi et al., "Bacteriophages and Phage-Inspired Nanocarriers for Targeted Delivery of Therepeutic Cargos", Adv Drug Deliv Rev. (2016).
Pranjol et al., "Bacteriophage-Derived Vectors for Targeted Cancer Gene Therapy", Viruses, vol. 7, pp. 268-284 (2015).
Zhu et al., "A prokaryotic-eukaryotic hybrid vector for delivery of large cargos of genes and proteins into human cells", Science Advances (2019).
Ozturk et al. "A Modular linked-AAV building block system for gene and protein delivery", 60 (9); Abstract 2901 (2019).
Office Action received in U.S. Appl. No. 17/488,542, filed Feb. 15, 2024.
Office Action received in U.S. Appl. No. 17/488,542, filed Mar. 28, 2024.
Non-Final Office Action received in U.S. Appl. No. 17/359,711, filed Jan. 21, 2022.
Final Office Action received in U.S. Appl. No. 17/359,711, filed Feb. 11, 2022.
Zhu et al., "A universal bacteriophage T4 nanoparticle platform to design multiplex SARS-CoV-2 vaccine candidates by CRISPR engineering", Science Advances, 7, Article eabh 1547, pp. 1-18 (2021).
Decision on Rejection received in Japanese Application No. 2022-510123 issued Jan. 11, 2023.
Office Action received in Korean Application No. 10-2022-7008043 dated Feb. 27, 2023.
Zhu et al., "A prokaryotic-eukaryotic hybrid vector for delivery of large cargos of genes and proteins into human cells", Science Advances, 5(8) 2019.
Office Action received in Chinese Application No. 202080065773.1 issued Oct. 25, 2022.
Karimi et al., "Bacteriophages and Phage-Inspired Nanocarriers for Targeted Delivery of Therapeutic Cargos", Adv. Drug. Deliv. Rev., 106(Pt A): pp. 45-62 (2016).
Balakrishnan et al., "Biopolymers augment viral vectors based on gene delivery", J. Biosc., vol. 44, No. 4, pp. 1-8 (2019).
Choi et al., "Lentivirus pre-packed with Cas9 protein for safer gene editing", Gene Therapy, vol. 23, pp. 627-633 (2016).
European extended Search Report received in EP Application No. 21850710.1 dated Sep. 9, 2024.
European extended Search Report received in EP Application No. 24155130.8 dated Jul. 24, 2024.

(56) References Cited

OTHER PUBLICATIONS

Fein et al., "Cationic Lipid Formulations Alter the In Vivo Tropism of AAV2/9 Vector in Lung", The American Society of Gene & Cell Therapy, vol. 17, No. 12, pp. 2078-2087 (2009).
Examination Report received in GB Application No. GB2301200.8 dated Aug. 8, 2024.
Examination Report received in GB Application No. GB2400771.8 dated Jul. 18, 2024.
Kabadi et al., "Multiplex CRISPR/Cas9-based genome engineering from a single lentiviral vector", Nucleic Acids Research, vol. 42, No. 19, e147, pp. 1-11 (2014).
Li et al., "Artificial Virus Delivers CRISPR-Cas9 System for Genome Editing of Cells in Mice", ACS Nano, vol. 11, pp. 95-111 (2017).
Liu et al., "Supporting Documents", Proceeding of the National Academy of Sciences, vol. 111, No. 37, pp. 13319-13324 (2014).
Liu et al., "Viral nanoparticle-encapsidated enzyme and restructured DNA for cell delivery and gene expression", PNAS, vol. 111, No. 37, pp. 13319-13324 (2014).
Lyu et al., "Delivering Cas9/sgRNA ribonucleoprotein (RNP) by lentiviral capsid-based bionanoparticles for efficient 'hit- and-run' genome editing", Nucleic Acids Research, pp. 1-13 (2019).
Mangeot et al., "Genome editing in primary cells and in vivo using viral-derived Nanoblades loaded with Cas9-sgRNA ribonucleoproteins", Nature Communications, pp. 1-15 (2019).
Mullaney et al., Capsid Targeting Sequence Targets Foreign Proteins into Bacteriophage T4 and Permits Proteolytic Processing, J. Mol. Biol., vol. 261, pp. 372-385 (1996).
Mullaney et al., "Bacteriophage T4 Capsid Packaging and Unpckaging of DNA and Proteins", Protocols for In Vitro Cultures and Secondary Metabolic Analysis of Aromatic and Medicinal Plants, Second Edition, Springer New York, vol. 1108, pp. 69-85 (2013).
Examination Report received in Canadian Application No. 3,148,369 dated Aug. 15, 2024.
Non-final Office Action received in U.S. Appl. No. 17/546,183, filed Sep. 6, 2024.
Song et al., "Delivery of CRISPR/Cas systems for cancer gene therapy and immunotherapy", Advanced Drug Delivery Reviews, vol. 168, pp. 158-180 (2021).
Tao et al., "Engineering of Bacteriophage T4 Genome Using CRISPR-Cas9" ACS Synth. Biol., 6 (10), pp. 1952-1961 (2017).
Tao et al., "In vitro and in vivo delivery of genes and proteins using the bacteriophage T4 DNA packaging machine", PNAS, vol. 110, No. 15, pp. 5846-5851 (2013).
Zhu et al., "Design of bacteriophage T4-based artificial viral vectors for human genome remodeling", Nature Communicaitons, 14:2928, pp. 1-19 (2023).
Zhu et al., "A prokaryotic-eukaryotic hybrid viral vector for delivery of large cargos of genes and proteins into human cells", Science Advances, vol. 5, pp. 1-14 (2019).

\* cited by examiner

BACTERIOPHAGE-BASED ARTIFICIAL VIRUSES FOR HUMAN GENOME REMODELING

CROSS-REFERENCE TO RELATED APPLICATIONS

This application is a divisional which claims benefit of priority of U.S. application Ser. No. 17/359,711, entitled "Design of Bacteriophage-based Artificial Viruses for Human Genome Remodeling, filed Jun. 28, 2021, which is a continuation in part of and claims benefit of priority of U.S. patent application Ser. No. 16/990,289, entitled "Prokaryotic-Eukaryotic Hybrid Viral Vector for Delivery of Large Cargos of Genes and Proteins into Human Cells," filed Aug. 11, 2020, which claims benefit of priority of U.S. Provisional Patent Application No. 62/888,576 filed on Aug. 19, 2019, entitled "A Prokaryotic-Eukaryotic Hybrid Viral Vector for Delivery of Large Cargos of Genes and Proteins into Human Cells". This application also claims benefit of priority of U.S. Provisional Patent Application No. 63/058,012, entitled "Design of Bacteriophage-based Artificial Viruses for Human Genome Remodeling," filed Jul. 29, 2020. The entire contents and disclosures of these patent applications are incorporated herein by reference in their entirety.

GOVERNMENT INTEREST STATEMENT

This invention was made with the United States government support under Grant Nos. AI111538 and AI081726 awarded by The National Institutes of Health (NIH) and Grant No. MCB-0923873 awarded by The National Science Foundation (NSF). The government has certain rights in the invention.

REFERENCE TO A "SEQUENCE LISTING"

The present application includes a Sequence Listing which has been submitted electronically in an ASCII text format. This Sequence Listing is named 109007-23787US01_sequence listing.TXT was created on Jun. 7, 2021, is 51,445 bytes in size and is hereby incorporated by reference in its entirety.

BACKGROUND

Field of the Invention

The present disclosure relates to generally to a human genome remodeling components, compositions, mechanisms and methods thereof.

Background of the Invention

Designing "artificial viruses" (AVs) programmed with biomolecules that can enter human cells and carry out precise molecular repairs will have broad applications to medicine. However, formulating an AV particle that can efficiently and safely deliver both therapeutic genes and proteins into the target cell to remodel human genome is still a major challenge. The present application overcomes the shortcomings of the prior art as described herein.

SUMMARY

According to a first broad aspect, the present disclosure provides a human genome remodeling artificial virus (AV) comprising: at least one viral vector; at least one therapeutic molecule; and a lipid coating, wherein at least one of the therapeutic molecules has gene modification or gene silencing activities.

According to a second broad aspect, the present disclosure provides a human genome remodeling artificial virus (AV) comprising: a T4 capsid; Cas9 protein; at least one RNA; at least one DNA; and a lipid coating, wherein the DNA is packaged inside the T4 capsid, wherein the RNA is selected from the group consisting of mRNA, siRNA and gRNA, wherein the lipid coating comprises at least one cationic lipid.

According to a third broad aspect, the present disclosure provides a method of genome modification comprising: infecting animal cells with an artificial virus (AV), wherein the AV comprises a viral vector; at least one therapeutic molecule; and a lipid coating, wherein at least one of the therapeutic molecules has gene modification or gene silencing activities.

According to a fourth broad aspect, the present disclosure provides a CRISPR-based method of programming artificial virus (AV) with genome modification capabilities comprising: generating a "acceptor" phage by deleting ipI and ipII genes from a wild type T4 phage; generating a host bacteria cell with a plasmid containing a gene of target protein and a spacer plasmid that expresses Cas9 or Cpf1 and CRISPR RNA corresponding to a protospacer sequence in the deleted region of the acceptor phage; infecting the host bacteria cell with the "acceptor" phage; recovering an engineered "acceptor" phage from the host bacteria cell; obtaining an empty engineered T4 capsid from the engineered "acceptor" phage; packaging at least one DNA in the engineered T4 capsid, wherein the gene of target protein is flanked by capsid targeting sequence (CTS) at the C-terminus and nuclear localization sequence (NLS) at the N-terminus to form CTS-gene-NLS sequence.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE INVENTION

Definitions

Figure 1:
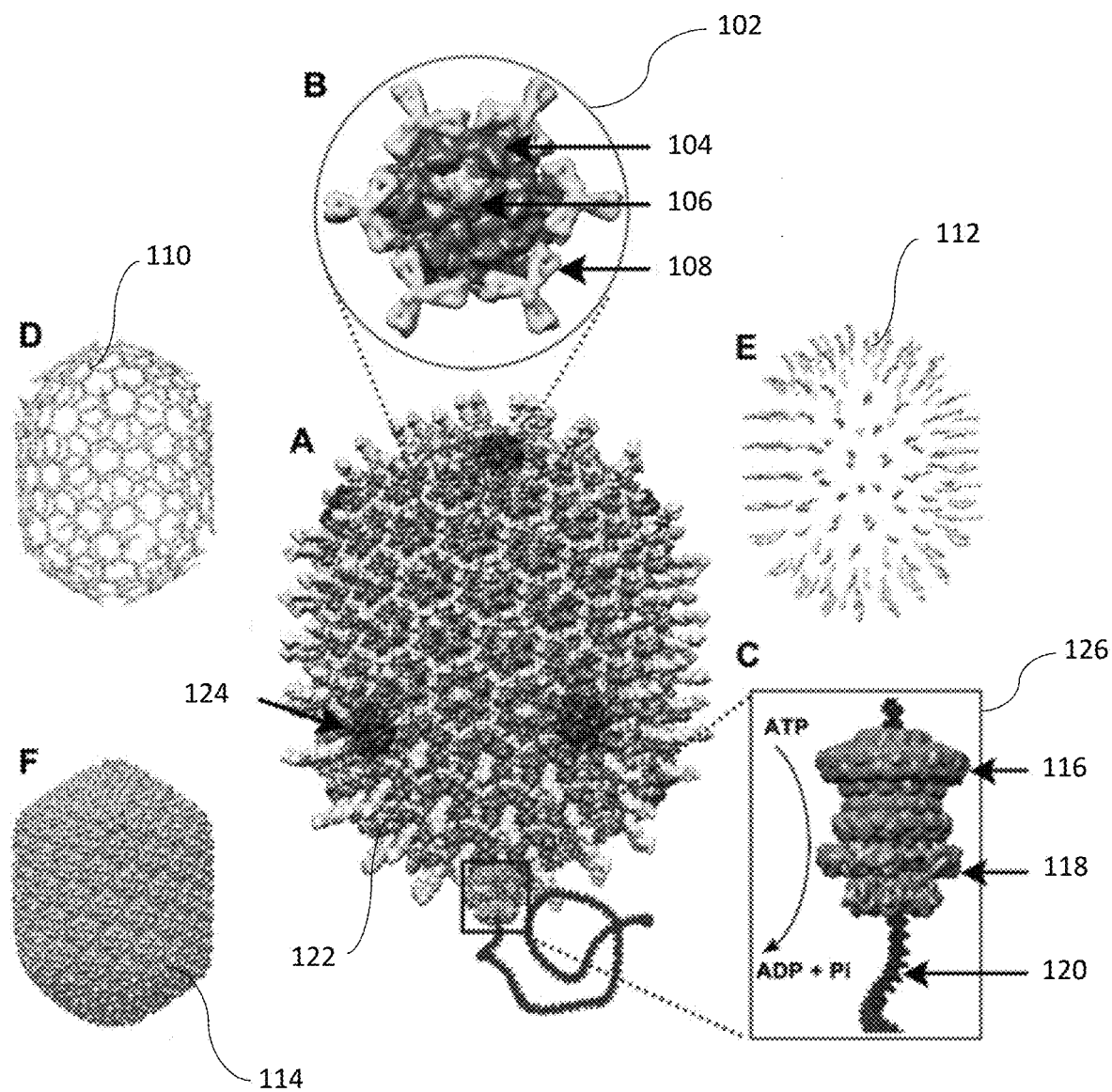
FIG. 1 is a schematic diagram of the bacteriophage T4-based artificial viruses according to one exemplary embodiment of the present invention.

Where the definition of terms departs from the commonly used meaning of the term, applicant intends to utilize the definitions provided below, unless specifically indicated.

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

For purposes of the present disclosure, the term "comprising", the term "having", the term "including," and variations of these words are intended to be open-ended and mean that there may be additional elements other than the listed elements.

For purposes of the present disclosure, directional terms such as "top," "bottom," "upper," "lower," "above," "below," "left," "right," "horizontal," "vertical," "up," "down," etc., are used merely for convenience in describing the various embodiments of the present disclosure. The embodiments of the present disclosure may be oriented in various ways. For example, the diagrams, apparatuses, etc., shown in the drawing figures may be flipped over, rotated by 90° in any direction, reversed, etc.

For purposes of the present disclosure, a value or property is "based" on a particular value, property, the satisfaction of a condition, or other factor, if that value is derived by performing a mathematical calculation or logical decision using that value, property or other factor.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present invention, the term "bacterial viruses", "bacteriophages", and "phages" are used interchangeably. These terms refer to a virus or a viral particle that can infect bacteria.

For purposes of the present invention, the term "capsid" and the term "capsid shell" refer to the protein shell of a virus comprising several structural subunits of proteins. The capsid encloses the nucleic acid core of the virus.

For purposes of the present invention, the term "vector", "vehicle", and "nanoparticle" are used interchangeably. These terms refer to a virus or a hybrid viral particle that can be used to deliver genes or proteins.

For purposes of the present invention, the term "bind," the term "binding" and the term "bound" refer to any type of chemical or physical binding, which includes but is not limited to covalent binding, hydrogen binding, electrostatic binding, biological tethers, transmembrane attachment, cell surface attachment and expression.

For purposes of the present invention, the term "nucleic acid" refers to polymers of nucleotides of any length, and include DNA and RNA. The nucleic acid bases that form nucleic acid molecules can be the bases A, C, G, T and U, as well as derivatives thereof. Derivatives of these bases are well known in the art. The term should be understood to include, as equivalents, analogs of either DNA or RNA made from nucleotide analogs. The term should also be understood to include both linear and circular DNA. The term as used herein also encompasses cDNA, that is complementary, or copy, DNA produced from an RNA template, for example by the action of reverse transcriptase.

For purposes of the present invention, the term "neck protein" and the term "tail protein" refer to proteins that are involved in the assembly of any part of the necks or tails of a virus particle, in particular bacteriophages. Tailed bacteriophages belong to the order Caudovirales and include three families: The Siphoviridae have long flexible tails and constitute the majority of the tailed viruses. Myoviridae have long rigid tails and are fully characterized by the tail sheath that contracts upon phage attachment to bacterial host. The smallest family of tailed viruses are podoviruses (phage with short, leg-like tails). For example, in T4 bacteriophage gp10 associates with gp11 to forms the tail pins of the baseplate. Tail-pin assembly is the first step of tail assembly. The tail of bacteriophage T4 consists of a contractile sheath surrounding a rigid tube and terminating in a multiprotein baseplate, to which the long and short tail fibers of the phage are attached. Once the heads are packaged with DNA, the proteins gp13, gp14 and gp15 assemble into a neck that seals of the packaged heads, with gp13 protein directly interacting with the portal protein gp20 following DNA packaging and gp14 and gp15 then assembling on the gp13 platform. Neck and tail proteins in T4 bacteriophage may include but are not limited to proteins gp6, gp25, gp53, gp8, gp10, gp11, gp7, gp29, gp27, gp5, gp28, gp12, gp9, gp48, gp54, gp3, gp18, gp19, gp13, gp14, gp15 and gp63.

For purposes of the present invention, the term "MOI" and the term "multiplicity of infection" refer to the ratio of agents (e.g. phage or more generally virus, bacteria) to infection targets (e.g. cell). In the present disclosure, these terms refer to the ratio of "artificial virus" (AV) particles to the human cells infected.

For purposes of the present invention, the term "RNP" and the term "ribonucleoprotein" refer to a complex of ribonucleic acid and RNA-binding protein (e.g. the complex of Cas9 protein and RNA). Examples of RNA include gRNA, mRNA and siRNA.

Figure 6:
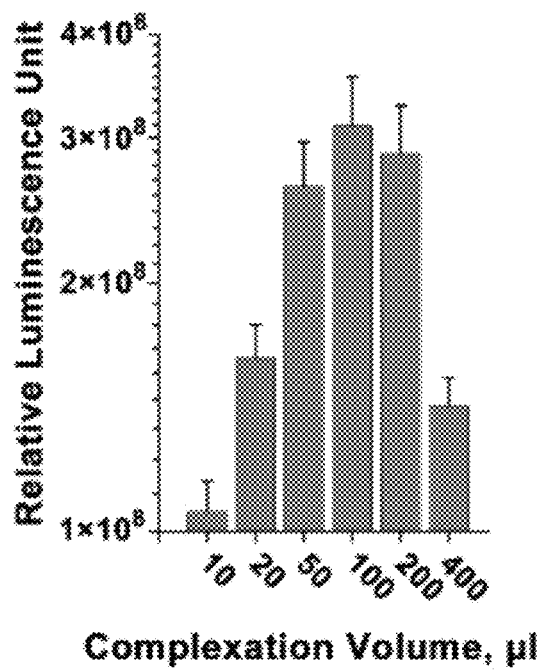
FIG. 6 is a graph showing the effect of T4 and lipid complexation volume on DNA delivery efficacy according to one exemplary embodiment of the present invention.

For purposes of the present invention, the term "complexation volume" refer to the total volume of mixture, in which a reaction is carried out. For instance, the complexation volume is the total volume of T4 and lipid mixture, which can range from 10-400 µl, as shown in FIG. 6, when evaluating the impact of complexation volume on DNA delivery efficacy.

Figure 7:
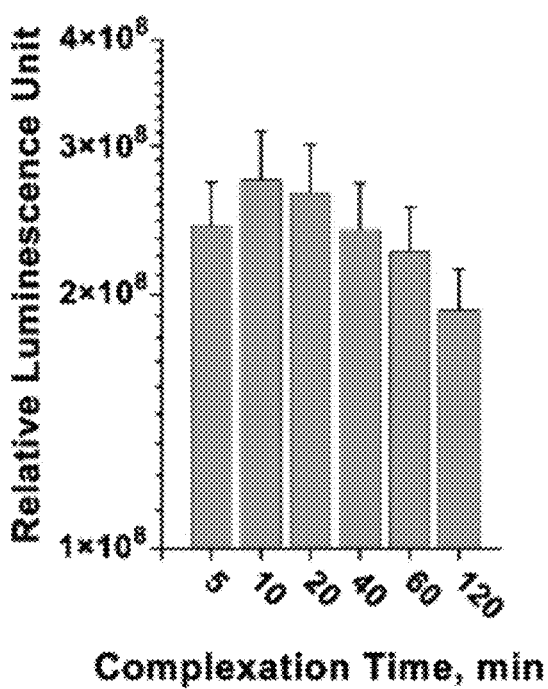
FIG. 7 is a graph showing the effect of T4 and lipid complexation time on DNA delivery efficacy according to one exemplary embodiment of the present invention.

For purposes of the present invention, the term "complexation time" refer to the total reaction time, for which a reaction is carried out. For instance, the complexation time is the total amount of time, for which T4 and lipid are mixed in order for T4 to be coated by lipid, which can range from 5-120 min, as shown in FIG. 7, when evaluating the impact of complexation time on DNA delivery efficacy.

For purposes of the present invention, the term "N.S." and the term "not significant" and the term "not significantly" refer to when the p value of Student's t-tests performed between two groups of data is less than 0.05.

For purposes of the present invention, the term "knock down" and the term "silencing" refer to a regulation of gene expression in a cell to prevent the expression of a certain gene. This regulation can occur through genetic modification or other treatment during either transcription or translation and is often used in research.

Description

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

Viruses are the most numerous and widely distributed organisms on Earth. They are also the most efficient biological machines[38]. A single virus about 100 nm in size containing a genetic code of mere 10,000-30,000 nucleotides, such as HIV, influenza virus, or coronavirus, can impair or kill a human person consisting of about 37 trillion cells, each ~100 µm in size and carrying a genetic code of ~3 billion nucleotides. This is because viruses evolved efficient mechanisms to replicate and assemble progeny on fast timescales, on the order of minutes in the case of bacterial viruses[11,34]. Hundreds to thousands of progeny viruses emerge from each infection, rapidly accumulating billions to trillions of new viruses starting from a single infection. This can cause global pandemics such as the current one caused by the novel coronavirus SARS-CoV-2[59]. If some of the efficient viral mechanisms could be harnessed by building "artificial viruses" (AVs) in the test tube, programmed with therapeutic molecules, such viruses, instead of replicating in host, could perform beneficial tasks to restore human health. Depending on the biomolecules it is programmed with, an artificial virus could replace a defective gene with a functional gene (gene therapy), manufacture a therapeutic molecule (immunotherapy), kill a cancer cell (cancer therapy), and so on[29,35,62]. However, despite many attempts over the years, the concept of artificial viruses remained a theoretical possibility.

An alternative approach researchers have taken was to engineer natural human viruses such that they can deliver a piece of therapeutic DNA or RNA as part of their genome. Two types of viruses, lentiviruses with ~10 Kbp size single-stranded RNA genome and adeno-associated viruses (AAVs) with ~5 Kbp size single-stranded DNA genome have been extensively employed[14,33]. While this approach has been successful, it also has inherent limitations. These viruses at best can deliver 1 or 2 therapeutic genes and it is difficult to incorporate additional therapeutic molecules such as proteins or protein-nucleic acid complexes that are essential for complex molecular operations such as genome editing. Safety concerns due to broad infectivity to human cells, pre-existing immunity, toxicity, and potential integration into host genome pose serious concerns[30,61].

In the present disclosure, a new type of artificial virus platform using the bacteriophage T4 is described. T4 belongs to myoviridae family and infects *Escherichia coli* bacterium, and it does not have any of the above limitations or safety concerns[31]. With an infection efficiency near 100%, and replicating at a rate of ~20 minutes, T4 is one of the most efficient viruses known[60]. FIG. 1 shows components of bacteriophage T4-based artificial viruses. Panel A of FIG. 1 shows structural model of phage T4 head (capsid), in which pentameric gp24* (124) vertices are shown in dark red. Panel B of FIG. 1 shows enlarged capsomer (hexamer), illustrating the arrangement of the major capsid protein gp23* (104) (dark green), Soc trimers (108) (light green), and Hoc fiber (106) (cyan). Panel C of FIG. 1 shows enlarged portal vertex showing gp20 (116) dodecamer (brown) and pentameric DNA packaging motor gp17 (118) (yellow). Panel D of FIG. 1 shows eight hundred and seventy Soc (108) molecules assembled at the quasi-three fold axes form a molecular cage (110) around the T4 capsid. Panel E of FIG. 1 shows one hundred and fifty-five Hoc fibers (112) from the center of capsomers. Panel F of FIG. 1 shows surface view of T4 capsid depicting the distribution of negative charges (114). Each negative charge is shown in red color.

As shown in FIG. 1, it contains a large 120×86 nm prolate icosahedral capsid (head) (122) assembled with 930 molecules or 155 hexameric capsomers (102) of 930 copies of the major capsid protein gp23* (104) ("*" represents cleaved mature form), 55 copies or 11 pentamers of gp24* (124) at eleven of the twelve vertices, and 12 copies of the portal protein gp20 (116) at the unique twelfth vertex5, 16, 34.

As shown in panel B of FIG. 1, each hexameric capsomers contains one copy of Hoc protein (106), 6 copies of gp23* (104) and 6 copies of Soc protein (108) that are shared with adjacent capsomers. Accordingly, each T4 head contains 155 copies of Hoc protein (106), 930 copies of gp23* (104) and 870 copies of Soc protein (108).

As shown in panel C of FIG. 1, attached to the twelfth vertex is the DNA packaging machine (126), containing 12 copies of the portal protein gp20 (116), and 5 copies of motor protein gp17 (118) and a central channel through which DNA of about 170 Kb (120) is transported. The portal vertex is a ring structure with a ~35 Å central channel through which the viral genome is transported into capsid by an ATP-powered pentameric molecular motor attached to it[15, 50]. The molecular motor contains 5 copies of motor protein gp17 (118). After one headful of genome, equivalent to ~170 Kbp linear dsDNA (120), is packaged[4, 42], the motor dissociates and "neck" proteins assemble followed by tail and tail fiber assembly to generate an infectious virion[26, 60].

The surface of T4 capsid is arrayed with two nonessential outer capsid proteins, Soc (108) (small outer capsid protein) (9.1 kDa; 870 copies per capsid) and Hoc (106) (highly antigenic outer capsid protein) (40.4 kDa; 155 copies per capsid)[16, 21]. Soc (108) is a tadpole-shaped molecule and binds at the quasi three-fold axes as a trimer. Each Soc (108) subunit acts as a "molecular clamp" by clasping two adjacent capsomers. As shown in panel D of FIG. 1, eight hundred and seventy such clamps form a molecular cage around the capsid greatly reinforcing the pressurized capsid due to its tightly packed DNA approaching crystalline density[39]. Consequently, the capsid is very stable even under harsh conditions such as pH 11. Hoc (106) on the other hand is a 170 Å-long fiber containing a string of four Ig-like domains with the C-terminal domain bound to the center of each gp23* capsomer (102). One hundred and fifty-five symmetrically positioned Hoc fibers emanate from T4 head[17]. Unlike Soc, Hoc provides only marginal stability to capsid. Its main function might be to allow phage to adhere to host surfaces through its Ig-like domains[1].

There are many reasons why phage T4 is an ideal platform to build artificial viruses. In fact, this concept evolved over ~40-years of genetic, biochemical, and structural analyses. First, the architecture of T4 phage with a stable capsid, external surface exposing 1,025 nonessential molecules, and an internal volume that can accommodate up to ~170 Kbp DNA provide a large amount of cargo space to incorporate therapeutic biomolecules[5, 54]. Second, there is a rich amount of accumulated knowledge on the genetic and biochemical mechanisms of head assembly and genome packaging that allow in vitro manipulations to build artificial viruses9, 22, 41, 47. Third, the atomic structures of almost all the capsid and packaging motor components that provided a wealth of information to engineer the T4 nanoparticle have been determined[5, 15, 17, 39, 49, 50]. Fourth, a series of studies demonstrated that Soc and Hoc serve as excellent adapters to tether foreign proteins to T4 capsid surface[27, 47]. Both have nanomolar affinity and exhibit exquisite specificity to T4 capsid, properties that are critically important for in vitro assembly[51, 65]. Fifth, a robust in vitro DNA packaging system in which a stable "emptied" T4 capsid can be re-filled with foreign DNA using the powerful DNA packaging motor has been developed[18, 63]. Finally, a CRISPR engineering strategy has been developed recently, which allowed facile insertion of foreign DNA fragments into phage genome to generate recombinant phages with unique phenotypic properties[44, 52, 53].

These provided an extraordinary foundation to design an artificial virus platform using T4 phage. The artificial virus design in the present disclosure takes an assembly-line approach, beginning with the empty capsid shell containing only three minimally essential capsid proteins gp23* (104), gp24* (124), and gp20 (116), and devoid of DNA and all other structural components including Soc, Hoc, neck, tail, and fibers. Using this protein shell as the basic building block, layers of cargo molecules are incorporated by a sequential process. Both the inside and outside of the shell are filled with these molecules that include proteins, DNAs, RNAs, and their complexes. The capsids are then coated with lipid molecules to create an "envelope" around these virus-like nanoparticles. The artificial viruses thus assembled mimic natural (human) viruses with a lipid coat, surface molecules, capsid shell, and packaged "genome". As the exemplary embodiments and examples in the present disclosure would demonstrate, these artificial viruses appear to use similar pathways used by natural viruses for entry into cells and trafficking to intracellular destinations.

As proof of this concept, the assembly of a series of artificial viruses that are directed to perform specific molecular operations to remodel the human genome is demonstrated in the present disclosure. These include: genome editing, gene recombination, gene replacement, gene expression, and gene silencing. For example, in one configuration, an artificial virus was programmed with five different components; Cas9 genome editing nuclease, Cre recombinase, two gRNAs, donor, and reporter plasmids. These AVs entered human cells by endocytosis and delivered payload molecules in the cytosol, which, upon reaching the appropriate intracellular locations, performed genome editing and site-specific recombination at distinct sites on the human genome. Such a large capacity, all-in-one, multiplex, programmable, and phage-based artificial viruses represent a new category of nanomaterial that could potentially transform future human therapies and personalized medicine[48].

Assembly of Phage T4 Artificial Viruses

Figure 2:
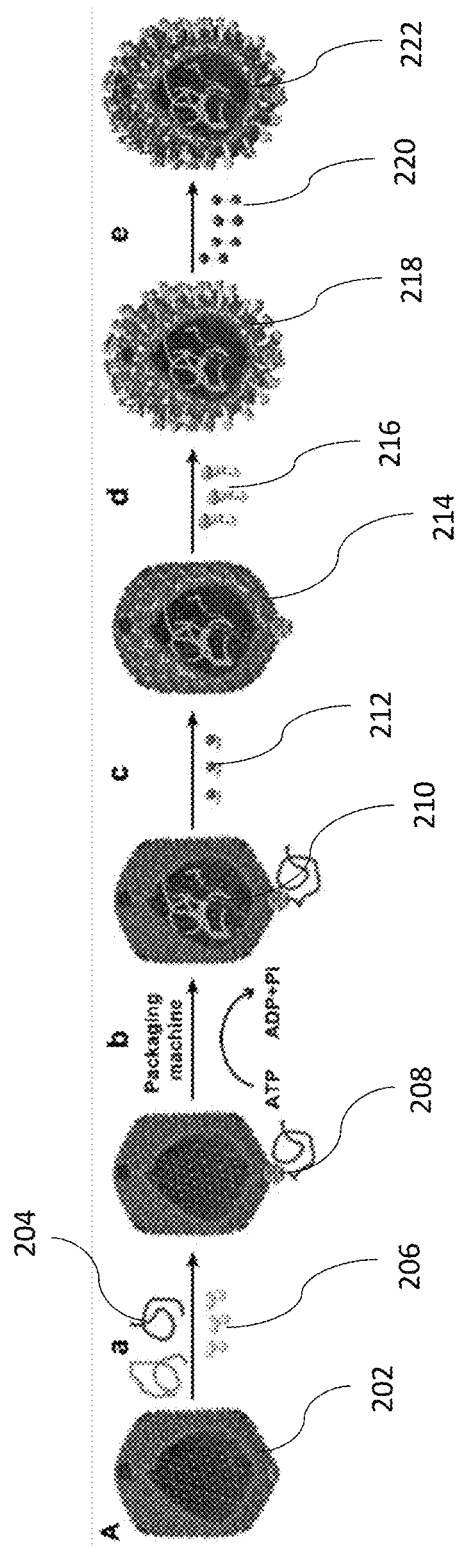
FIG. 2 is a schematic diagram of sequential assembly-line to generate T4-AVs according to one exemplary embodiment of the present invention.

In one embodiment, the artificial viruses are assembled by sequential incorporation of purified biomaterials to generate a virus structural mimic, as shown in FIG. 2. Starting with an empty capsid shell (202) isolated from a neck- and tail-minus T4 phage mutant-infected *E. coli*[63], a pentameric packaging motor (208) was assembled on the portal vertex by simply adding the (monomeric) motor protein gp17 (206) to the reaction mixture. The capsid interior is then filled with foreign DNA by adding linearized plasmid DNA and ATP to the assembly reaction (a, b in FIG. 2)[50]. The T4 packaging motor (208) captures DNA (204) and translocates the DNA into capsid from one end to the other in a processive fashion. This can repeat many times resulting in successive packaging of a series of DNA molecules until the head is full (headful packaging)[25, 56]. Consequently, multiple copies of multiple plasmids are packaged inside the ~170 Kbp capacity T4 head[63]. The DNA packed T4 head (210) is shown in FIG. 2 after step b. Since the motor exhibits no sequence specificity, the composition of the packaged "genome" would be the same as that presented to the assembly reaction.

The exterior of the capsid was then arrayed with Soc- (212) and/or Hoc-fused protein (216) molecules by adding these proteins to the same reaction mixture (c, d in FIG. 2). The Soc-fused protein (212) may be Soc-protein or Soc-ribonucleoprotein (RNP). The Hoc-fused protein (216) is Hoc-protein combination. At ~20:1 ratio of molecules to binding sites, full occupancy, i.e., up to 870 Soc- (212) and 155 Hoc-fused proteins (216) per capsid, can be achieved[5, 51]. The particles (214 and 218) coated with Soc- (212) and/or Hoc-fused protein (216) molecules are shown in FIG. 2., after steps c and d, respectively. The particles are then coated with cationic lipid molecules (220) (e in FIG. 2), resulting in the final artificial virus particle (222).

Figure 3:
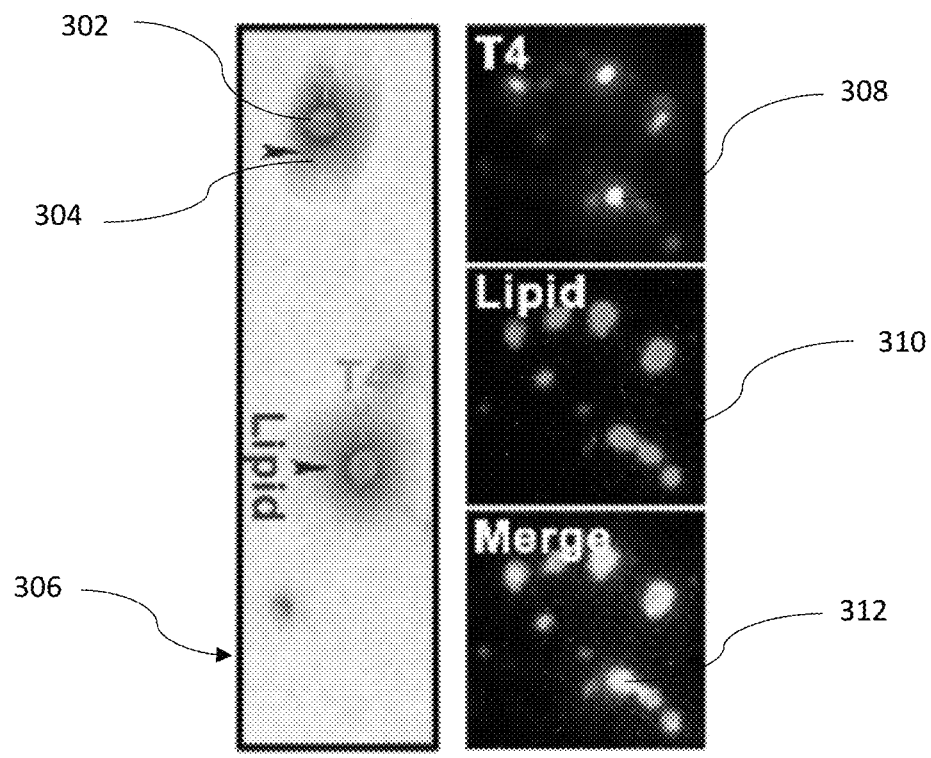
FIG. 3 is a graph showing the lipid-coated T4-AVs according to one embodiment of the present invention.

Since the T4 capsid has a high density of negative charges, ~8,700 per capsid[5,45], as shown in panel F of FIG. 1, cationic lipids would spontaneously assemble on T4 capsid via electrostatic interaction. In one embodiment, extensive lipid binding occurs when cationic lipids are added to T4 capsids. FIG. 3 contains microscopic photos showing the lipid (304) surrounding the T4 capsid (302). As shown in FIG. 3, a negative EM photo (306) shows a diffused stain (304), which is lipid, around the T4 capsid (302). When labeled with fluorophores, these "enveloped" particles (yellow, after combining Alexa Fluor 594 fluorophore and NBD fluorophore) (312) showed co-localization of the T4 capsid-labeled Alexa Fluor 594 fluorophore (red) (308) and the lipid-labeled NBD fluorophore (green) (310). The T4-AV nanoparticles thus assembled possess the basic architecture of naturally enveloped viruses with lipid coat, surface-exposed molecules, capsid shell, and packaged "genome".

The T4 Artificial Viruses Efficiently Deliver Genetic Payloads into Human Cells

The T4-AVs by virtue of their positively charged lipid coat would efficiently bind to the negatively charged and lipophilic surface of human cells and allow efficient entry[57]. Several cationic lipids and cell penetration peptides have been well-documented to exhibit such a property[19, 66]. Indeed, a series of embodiments in the present disclosure have demonstrated that the lipid-coated T4-AVs efficiently delivered genetic payloads into human cells.

In one embodiment, when co-packaged with two different plasmids, on average ~5 molecules each of GFP reporter plasmid (5.4 Kbp) and luciferase plasmid (Luci, 6.3 Kbp) per capsid, these AVs transduced both the reporter plasmids into human embryonic kidney HEK293T(293) cells at near 100% efficiency.

Figure 4:
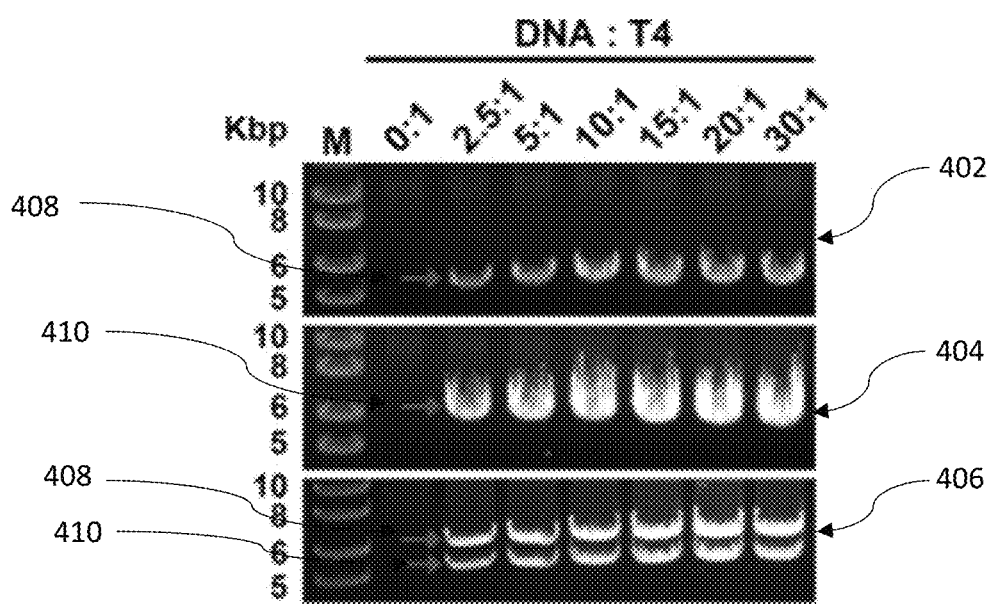
FIG. 4 is a graph showing the quantification of packaged GFP and luciferase DNAs for various T4-AVs at different DNA to T4 ratio according to one exemplary embodiment of the present invention.

FIG. 4 shows the Quantification of packaged GFP and luciferase DNAs for T4-AVs described in the present disclosure. As shown in FIG. 4, the linearized DNAs are incubated with T4 at increasing DNA-to-capsid ratios as indicated at the top of the panels, with the red arrows indicate the position of the packaged GFP (408) and luciferase DNA band(s) (410) as analyzed by agarose gel electrophoresis. The top panel of FIG. 4 (402) shows the agarose gel electrophoresis of the packaged GFP DNA band(s), the middle panel of FIG. 4 (404) shows the agarose gel electrophoresis of the packaged luciferase DNA band(s), the bottom panel of FIG. 4 (406) shows the agarose gel electrophoresis of both packaged GFP and luciferase DNA band(s). Maximum packaging capacity is reached at a ratio of 15-20:1.

Figure 5:
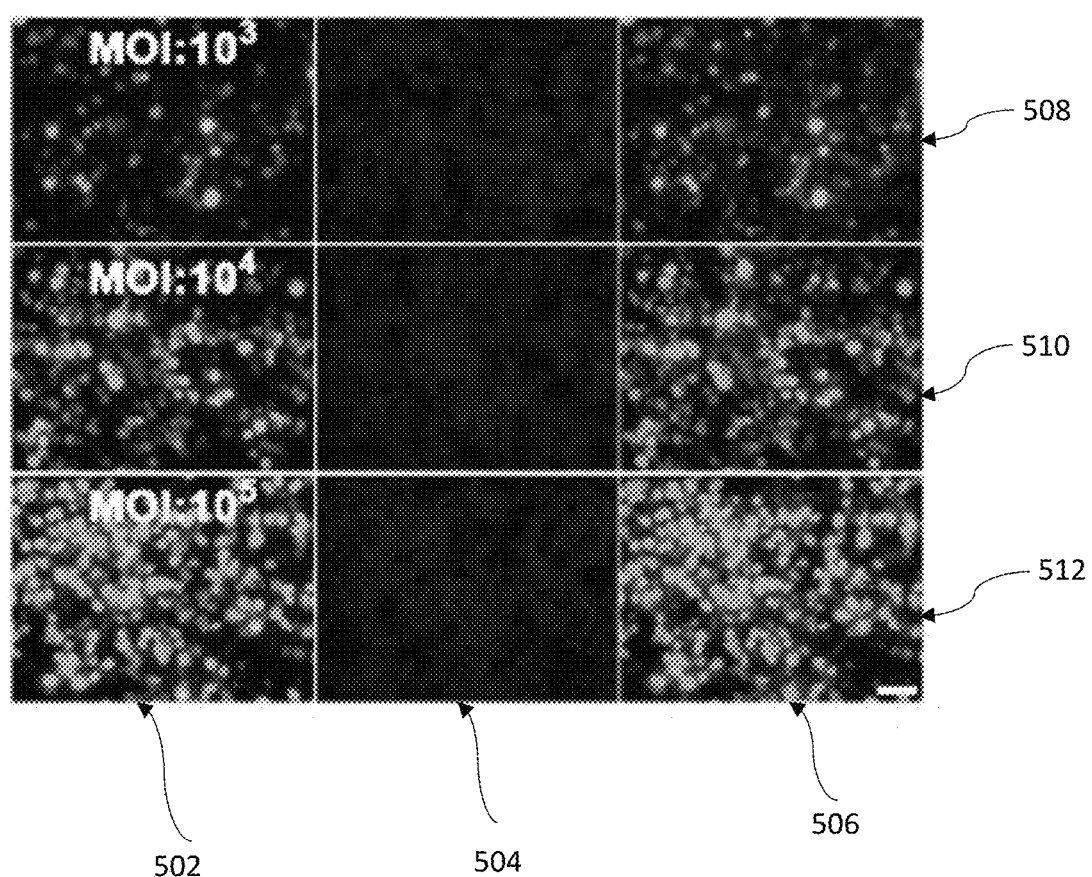
FIG. 5 is a graph showing the delivery of packaged DNA by T4(GFP)-AVs into 293 cells at different multiplicity of infection (MOI) according to one exemplary embodiment of the present invention.

FIG. 5 shows the efficient delivery of packaged DNA by T4(GFP)-AVs into 293 cells, at the MOI of $10^3$, $10^4$ and $10^5$. The T4(GFP)-AVs delivered is determined by GFP expression, as shown in the left column (502) of FIG. 5. Cell nuclei are stained and visualized with Hoechst, as shown in the middle column (504) of FIG. 5. The right column (506) of FIG. 5 shows the co-localization of T4(GFP)-AVs delivered and the cell nuclei, indicating the efficient delivery of T4(GFP)-AVs. Furthermore, the top row (508) of FIG. 5 shows the delivery of T4(GFP)-AVs at MOI of $10^3$. The middle row (510) of FIG. 5 shows the delivery of T4(GFP)-AVs at MOI of $10^4$. The bottom row (512) of FIG. 5 shows the delivery of T4(GFP)-AVs at MOI of $10^5$.

Figure 8:
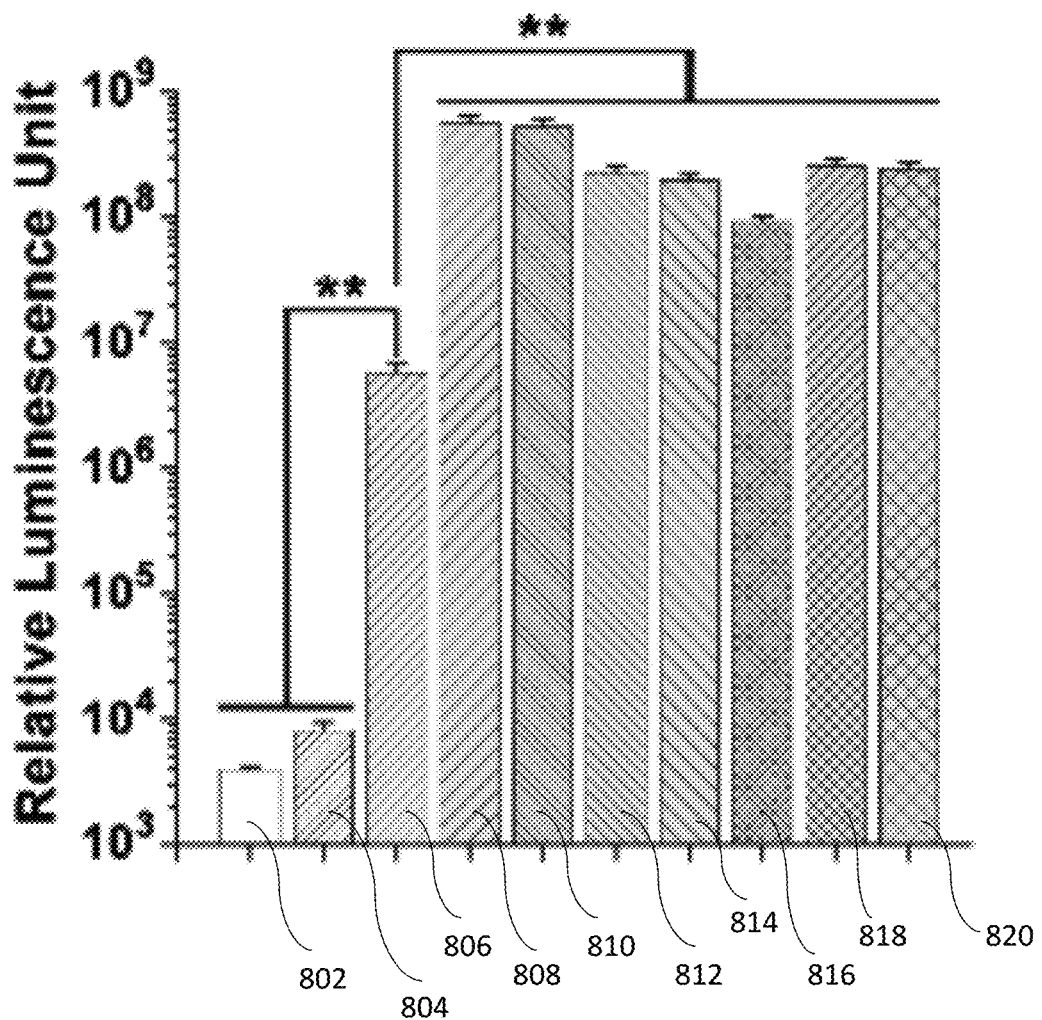
FIG. 8 is a graph showing the transduction efficiencies of AVs coated with different cationic lipids according to exemplary embodiments of the present invention.

FIGS. 6 and 7 show the effect of T4 and lipid complexation volume and time on DNA delivery efficacy, determined by luciferase activity. The luciferase activity is measured by relative luminescence unit. As shown in FIG. 6, the relative luminescence unit is impacted by complexation volume and maximizes at the complexation volume of 100 μl. As shown in FIG. 7, the relative luminescence unit is also impacted by complexation time and maximizes at the complexation time of 10 min. FIG. 8 shows the transduction efficiencies of AVs coated with different cationic lipids, including LPF2K-AV (808), LPFRNAiMAX-AV (810), LPF3K-AV (812), LPFLTX-AV (814), LPFStem-AV (816), EXPI-AV (818) and FECT-AV (820), while the cell control (802), the "naked" T4 (Luci) capsid (804) and cationic T4 (Luci) capsid without lipid (T4 (Luci)-TAT) (806) are used for comparison.

Figure 9:
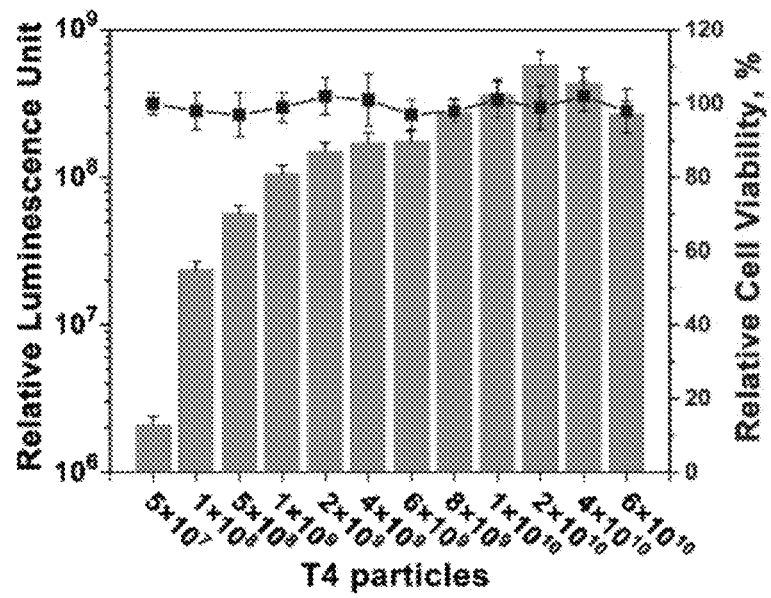
FIG. 9 is a graph showing the optimal ratio of T4 head particles to LPF2K concentration on delivery efficacy and cell viability according to one exemplary embodiment of the present invention.
Figure 10:
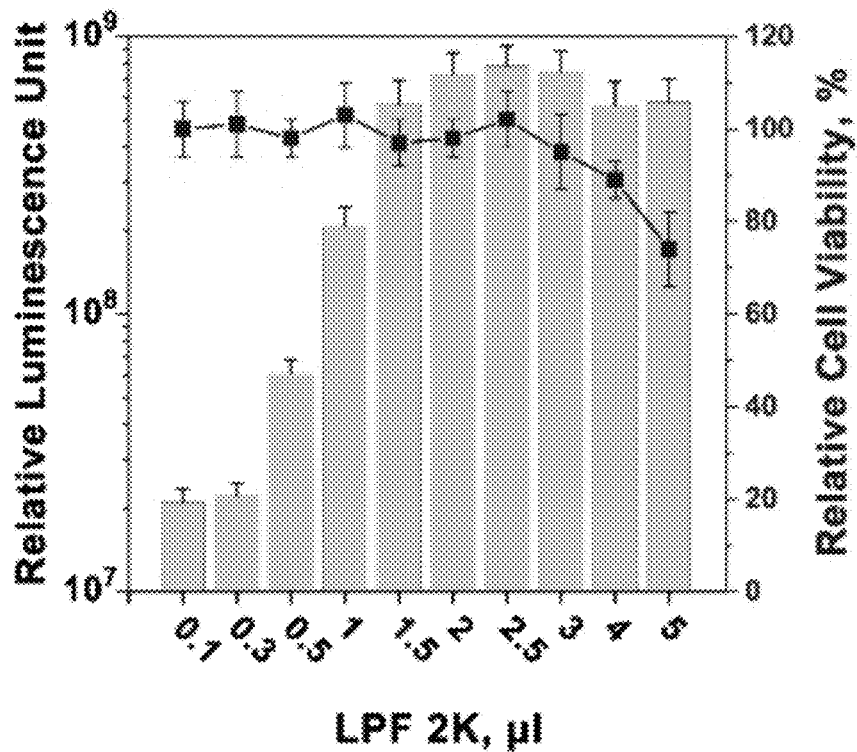
FIG. 10 is a graph showing the optimal ratio of T4 head particles to LPF2K concentration on delivery efficacy and cell viability according to one exemplary embodiment of the present invention.

Under optimal conditions (the complexation volume is 100 μl and the complexation time is 10 min), the luciferase activity of capsids with cationic lipid coat (808 through 820) is ~$10^5$-fold higher than the "naked" capsids (804) lacking the cationic lipid coat, and ~$10^2$-fold higher than the capsids that are cationic but lacked the lipid (806). The latter capsids (806) are prepared by displaying a cationic cell penetration peptide, HIV-TAT (NGYGRKKRRQRRRG)[55]. As shown in FIG. 8, no major differences are observed with various cationic lipids, although LPF2K and LPFRNAiMAX gave the best transduction efficiencies. Relatively low amounts of lipids were sufficient to coat the capsids and no significant cell toxicity is observed. FIG. 9 shows the optimal ratio of T4 head particles to LPF2K concentration on delivery efficacy, as indicated by luminescence activity, and cell viability. Luminescence activity (histogram) and cell viability assay (blue line) are performed at 48 h post-transduction. Quantification of the number of viable cells in culture is based on the determination of ATP present, which signaled the presence of metabolically active cells, as determined by luminescent cell viability assay. Percent viability is calculated in comparison with the untreated control. As shown in FIG. 9, the delivery efficacy increases with the ratio of T4 head particles to LPF2K concentration, while the cell viability remains at about 100% at all ratio of T4 head particles to LPF2K concentration tested. FIG. 10 shows the optimization of the LPF2K amount for complexing with $2\times10^{10}$ T4(Luci) (histogram) and relative cell viability (blue line).

As shown in FIG. 10, the complexing increases with the LPF2K amount, while the cell viability remains at about 100% when the LPF2K amount is no greater than 2.5 µl, but decrease with increasing LPF2K amount, when the LPF2K amount is greater than 2.5 µl.

Figure 11:
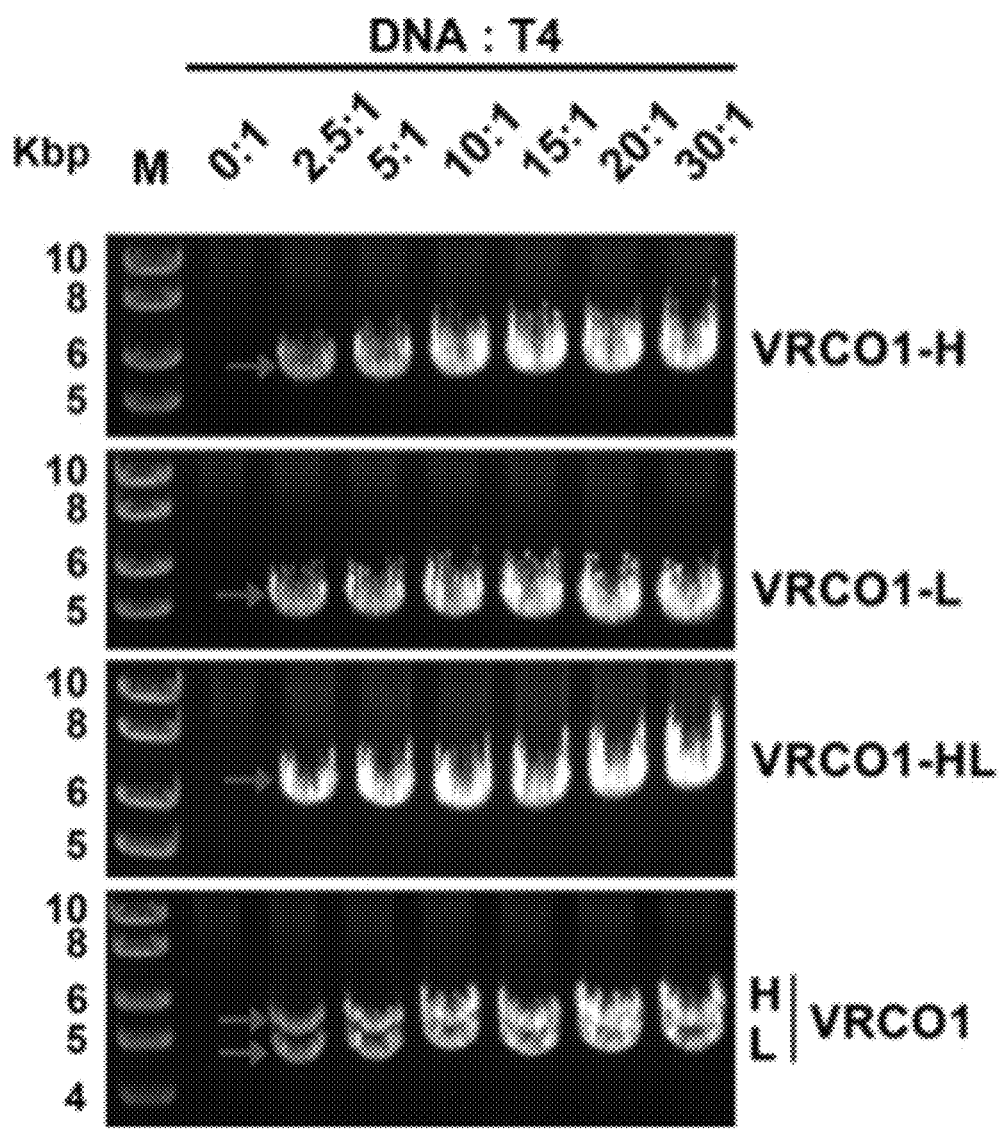
FIG. 11 is a graph showing the quantification of packaged VRC01 plasmid for T4-AVs at different DNA to T4 ratio according to one exemplary embodiment of the present invention.
Figure 12:
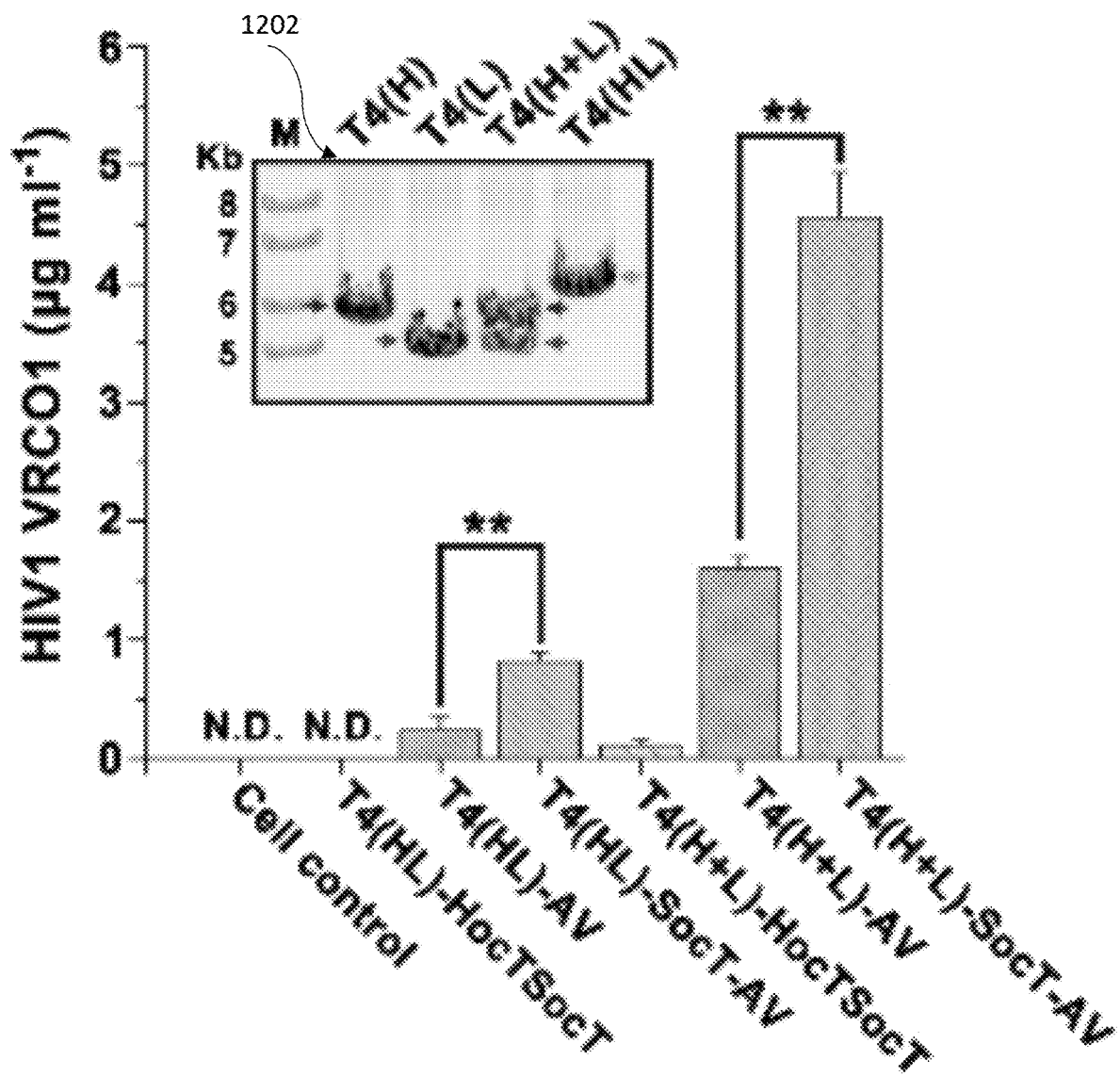
FIG. 12 is a graph showing the quantification of the amount of VRC01 antibody secreted by transduced cells according to one exemplary embodiment of the present invention.

In one embodiment, AVs packaged with two therapeutically relevant expression plasmids, the heavy (H) and light (L) chain plasmids of VRC01 antibody, a potent broadly neutralizing antibody against HIV-1[64], are assembled. Thus, these AVs can co-deliver more than one plasmid. FIG. 11 shows the quantification of packaged VRC01 plasmid for T4-AVs at different DNA to T4 ratio, as analyzed by agarose gel electrophoresis. The linearized DNAs are incubated with T4 at increasing DNA-to-capsid ratios as indicated at the top of the panels. As shown in FIG. 11, the DNAs packed and analyzed are VRC01 heavy chain along, VRC01 light chain alone, VRC01 heavy and light chains as one molecule and VRC01 heavy and light chains as separate molecules but packed in one T4-Avs particle. Maximum packaging capacity is reached at a ratio of 15-20:1. Therefore, an average of 10-12 molecules of H and L plasmids are packaged per capsid. FIG. 12 shows the quantification of the amount of VRCO1 antibody secreted by transduced cells. A HIV gp120 envelope protein-specific ELISA is conducted to quantify the amount of VRCO1 antibody secreted by 293 cells 48 h following T4-AV transduction. The inset (1202) shows the packaging of VRCO1 heavy chain H (blue arrow), light chain L (red arrow), H+L chains, and H–L single chain (green arrow). As shown in FIG. 12, these VRC01-AVs efficiently co-transduce and co-express the H and L chains, as evident from the secretion of functional immunoglobulin (Ig) molecules at high levels (~4.5 mg/liter). These levels are about 20-fold higher than when the H and L chains are delivered by cationic-only (TAT-displayed) AVs lacking the lipid coat. In FIG. 12, the amounts of VRCO1 antibody secreted by transduced cells infected by viral particles lacking the lipid coat are shown in columns labelled as "cell control", "T4(HL)-HocTSocT" and "T4(H+L)-HocTSocT", while those of cells transduced with AVs with the lipid coat are shown in columns labelled as "T4(HL)-AV", "T4(HL)-SocT-AV", "T4(H+L)-AV" and "T4(H+L)-SocT-AV". Naked particles lacking either the cationic or the lipophilic character produced very low levels of the antibody.

Figure 13:
FIG. 13 is a graph showing the quantification of packaged VRC01 and CH58 plasmids for T4-AVs at different DNA to T4 ratio according to one exemplary embodiment of the present invention.
Figure 14:
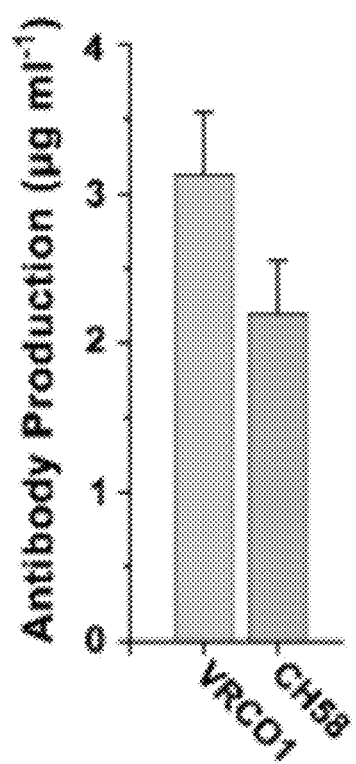
FIG. 14 is a graph showing the quantification of the amount of VRC01 and CH58 antibodies secreted by transduced cells according to one exemplary embodiment of the present invention.

In another embodiment, four plasmids containing two H and two L chains belonging to two different HIV-1 antibodies, VRC01 and CH58, are packed into the same capsid. FIG. 13 shows the quantification of packaged VRC01 and CH58 plasmids for T4-AVs at different DNA to T4 ratio, as analyzed by agarose gel electrophoresis. The linearized DNAs are incubated with T4 at increasing DNA-to-capsid ratios as indicated at the top of the panels. According to FIG. 13, an average of ~11 molecules, mixture of four different plasmids, are packaged in the same capsid. FIG. 14 shows the quantification of the amount of VRCO1 and CH58 antibodies secreted by transduced cells. ELISA titers of secreted VRCO1 and CH58 antibody production by the 293 cells following AV(VRCO1+CH58) transduction are determined. These AVs when co-transduced into 293 cells secreted both the VRC01 (~3 mg/liter) and CH58 (~2 mg/liter) antibodies, according to FIG. 14.

Figure 15:
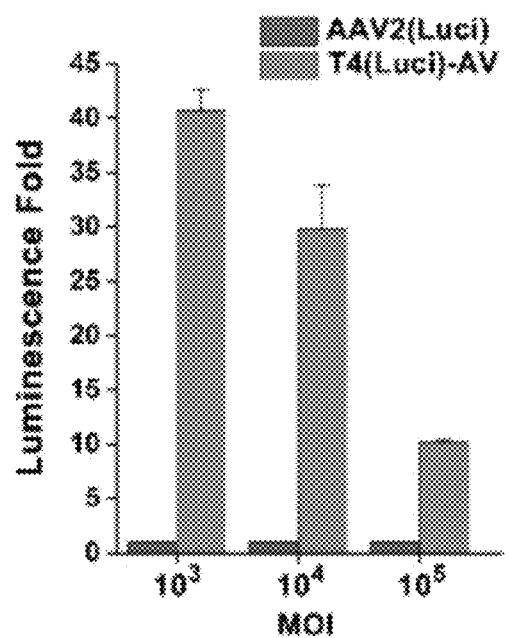
FIG. 15 is a graph showing the comparison of transduction efficiencies of T4-AVs and AAVs according to one exemplary embodiment of the present invention.

The above sets of data demonstrate that the cationic lipid-coated T4-AVs efficiently co-deliver and co-express multiple recombinant plasmids in human cells, as well as assemble functional Ig complexes. The efficiency of AV delivery is remarkably high, considering that it is a phage-based platform. FIG. 15 shows a head-to-head comparison of transduction efficiencies of T4-AVs and AAVs as determined by luciferase activity at the ratio of $10^3$, $10^4$, and $10^5$ nanoparticles per cell. According to FIG. 15, the T4-AVs gave ~10-40 fold greater expression of the luciferase reporter gene than that of AAV, one of the most efficient and widely used viral vectors for gene therapy[33]. This might be because the T4-AVs can deliver multiple copies of a genetic payload in a single transduction event, whereas AAV and other vectors such as lentiviruses are limited to delivering only one copy at a time.

Figure 16:
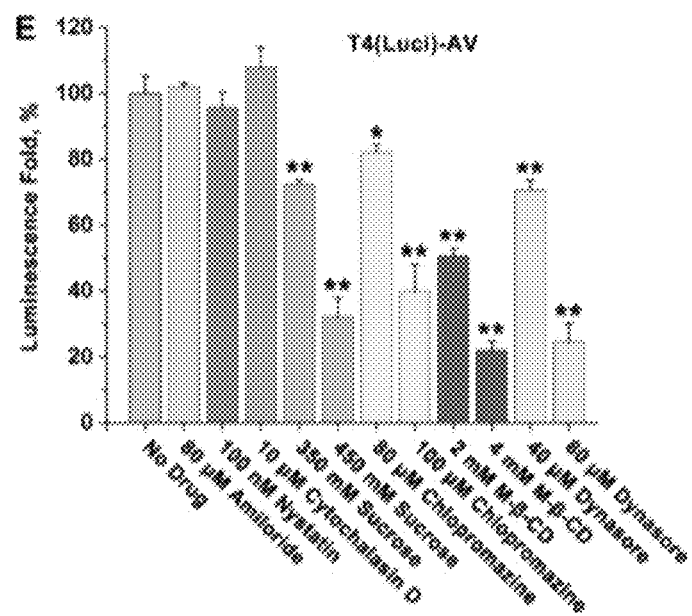
FIG. 16 is a graph showing the comparison of luciferase expression with the presence of different compounds according to one exemplary embodiment of the present invention.
Figure 17:
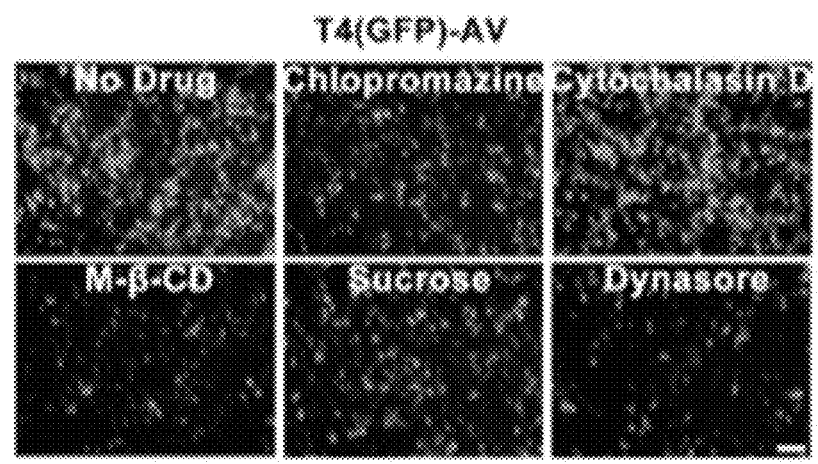
FIG. 17 is a graph showing the comparison of GFP expression with the presence of different compounds according to one exemplary embodiment of the present invention.
Figure 18:
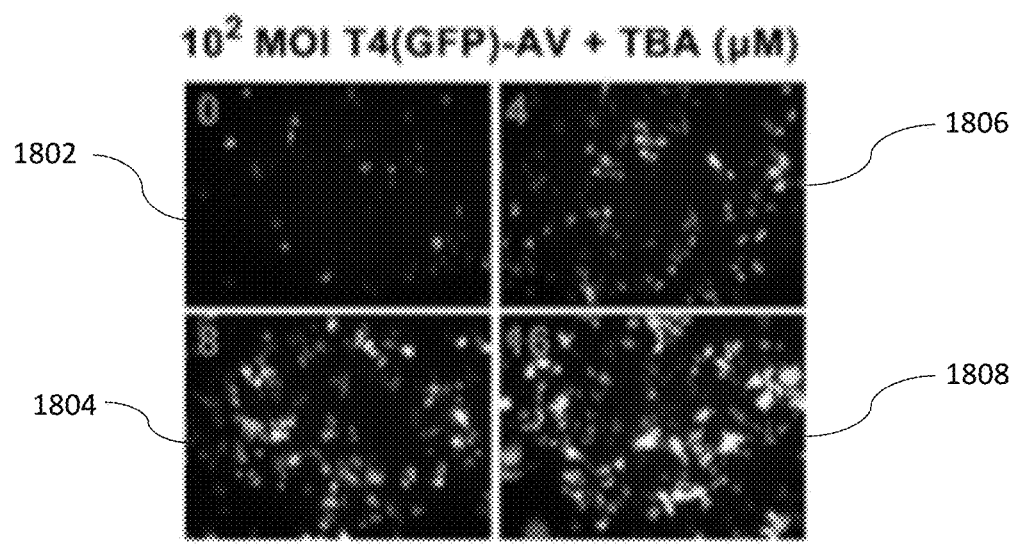
FIG. 18 is a graph showing the enhancement of T4-AV delivery with TBA treatment according to one exemplary embodiment of the present invention.

However, the mechanisms involved in entry, uncoating, and intracellular trafficking of T4-AVs are not completely understood. To understand the entry and intracellular trafficking pathways used by T4-AVs, cellular uptake of T4(Luci)-AVs is analyzed by treatment with various inhibitors. In one embodiment, cells are pretreated with various inhibitors for 30 min before exposure to T4(Luci)-AVs. FIG. 16 shows the comparison of luciferase expression with the presence of different compounds. Compounds such as sucrose and chlorpromazine, inhibitors of clathrin-mediated endocytosis, methyl-β-cyclodextrin (M-β-CD), a cholesterol-depleting agent, and dynasore, a dynamin-mediated endocytosis inhibitor, can cause profound reduction in AV delivery. Furthermore, the GFP expression with the presence of selective inhibitors is also compared, as shown in FIG. 17. the GFP expression reflects delivery efficacy. According to FIG. 17, the level of GFP expression with the presence of cytochalasin D is about the same as when do drug/inhibitor is added, while the presence of chlorpromazine, M-β-CD, sucrose, and dynasore reduces the level of GFP expression, which is consistent with the luciferase expression data shown in FIG. 16. This evidence suggests that the T4-AVs are internalized through dynamin- and clathrin-dependent endocytosis, in which plasma lipid raft also probably plays an important role[12]. The lipid coat apparently facilitated the escape of T4-AVs from the late endosome into the cytosol where uncoating and release of cargos occurred. Chloroquine, a compound known to enhance the endosomal escape of cationic T4-TAT[65], does not further enhance the already very efficient delivery by the cationic lipid-coated T4-AVs. Furthermore, Tubastatin A (TBA), a microtubule-binding agent that stabilizes microtubules and facilitates transport of DNA from the cytosol to nucleus[3] significantly can enhance the reporter signal of the AV-packaged DNA molecules. FIG. 18 shows the enhancement of reporter signal of the AV-packaged DNA molecules when the amount of TBA added is 4 µM (1806), 8 µM (1804) and 16 µM (1808), compared to when no TBA is added (1802).

Co-Delivery of Genes and Proteins by T4 Artificial Viruses

Figure 19:
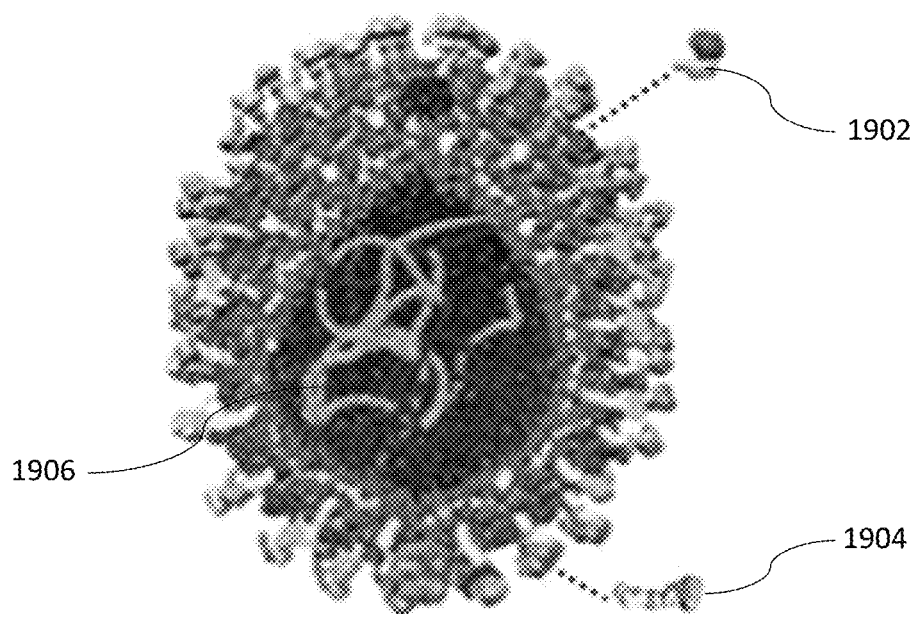
FIG. 19 is a schematic diagram showing the locations of protein and DNA cargos carried by T4-AVs according to one exemplary embodiment of the present invention.

In one embodiment, T4-AVs can co-deliver proteins along with genes. A series of AVs are assembled by displaying proteins fused to either Soc or Hoc. FIG. 19 shows the locations of Soc-fused (1902) and Hoc-fused protein (1904) and DNA (1906) cargos carried by T4-AVs. A series of proteins having different size, charge, oligomeric state, and function are incorporated, which are summarized in the table below.

| Displayed protein | MW (KDa) | Protein charge | Function | Copies/capsid |
|---|---|---|---|---|
| Cas9-Soc (SEQ ID NO: 16) | 169.2 | +25 | RNA-guided-DNA endonuclease | 550 |
| Cpf1-Soc (SEQ ID NO: 17) | 159.6 | +13 | | 450 |
| Cre-Soc (SEQ ID NO: 22) | 49.2 | +11 | DNA recombinase | 630 |

-continued

| Displayed protein | MW (KDa) | Protein charge | Function | Copies/capsid |
|---|---|---|---|---|
| Cre-Hoc (SEQ ID NO: 18) | 80.9 | +11 | | 95 |
| Soc-TAT | 25.8 | +8 | Cell penetrating | 750 |
| RGD-Hoc (SEQ ID NO: 19) | 45.5 | −1 | Cell adhesion motif | 85 |
| GFP-Soc | 35.5 | −8 | Fluorescent protein | 660 |
| β-Gal-Soc | 128.8 | −40 | Glycoside hydrolase | 320 |
| Soc-RGD | 10.1 | −1 | Cell adhesion motif | 710 |

Figure 20:
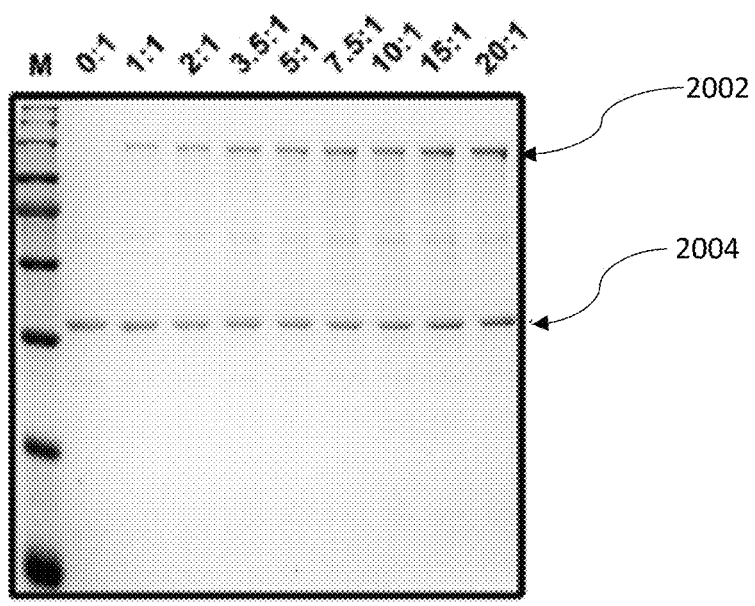
FIG. 20 is a graph showing the display of β-Gal-Soc on T4 capsids according to one exemplary embodiment of the present invention.
Figure 21:
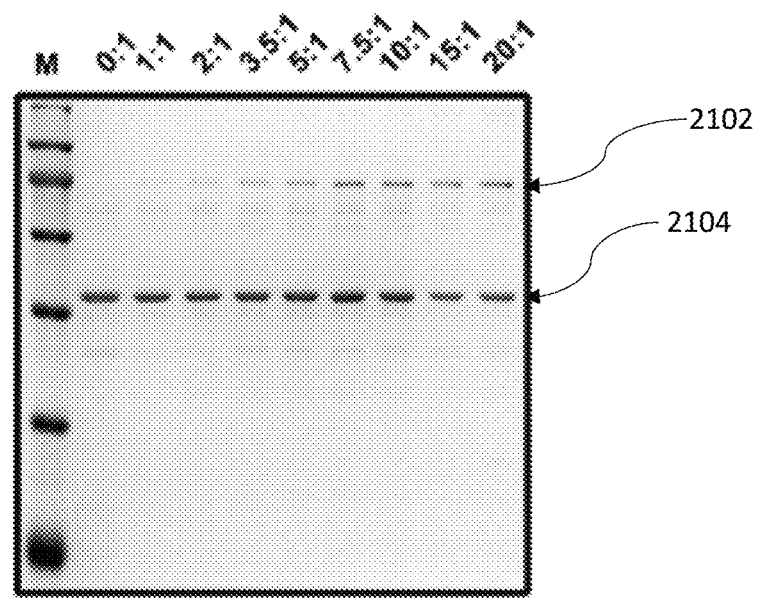
FIG. 21 is a graph showing the display of Cre-Hoc on T4 capsids according to one exemplary embodiment of the present invention.

In one embodiment, the display of Soc- and Hoc-fused proteins on T4 capsids is analyzed by gel electrophoresis. FIGS. 20 and 21 show binding patterns at different ratios that indicate that saturation reached at ~15-20:1 ratio, which is consistent with the previously reported data using many other proteins (not shown). FIG. 20 shows the position of β-Gal-Soc (2002) and the major capsid protein gp23* (2004), which is used as an internal control to determine the copy number of displayed β-Gal-Soc per capsid particle. FIG. 21 shows the position of Cre-Hoc (2102) and the major capsid protein gp23* (2104), which is used as an internal control to determine the copy number of displayed Cre-Hoc per capsid particle.

Figure 22:
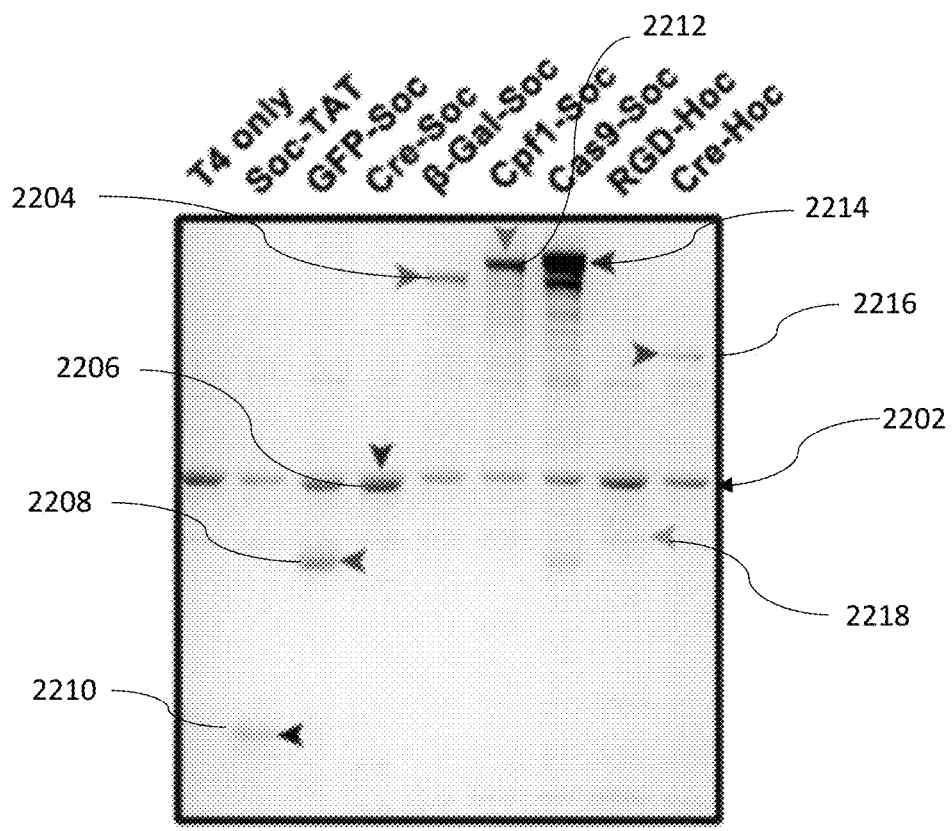
FIG. 22 is a graph showing the display of various Soc- and Hoc-fused proteins on T4 capsids according to one exemplary embodiment of the present invention.

Soc-TAT, GFP-Soc, Cre-Soc (SEQ ID NO: 22), β-Gal-Soc, Cpf1-Soc, Cas9-Soc (SEQ ID NO: 16), RGD-Hoc, and Cre-Hoc are overexpressed, purified, and incubated with purified T4 heads at increasing ratios of protein molecules to Soc- or Hoc-binding sites. FIG. 22 shows the positions of various displayed proteins, including Soc-TAT (2210), GFP-Soc (2208), Cre-Soc (2206), β-Gal-Soc (2204), Cpf1-Soc (2212), Cas9-Soc (2214), RGD-Hoc (2218), and Cre-Hoc (2216), and the major capsid protein gp23* (2202), which is used as an internal control to determine the copy number of displayed protein per capsid particle.

Figure 23:
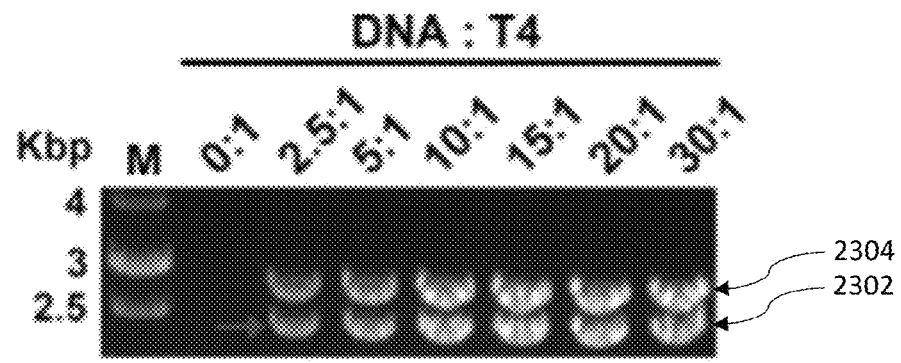
FIG. 23 is a graph showing the quantification of packaged mCherry reporter plasmid for T4-AVs at different DNA to T4 ratio according to one exemplary embodiment of the present invention.
Figure 24:
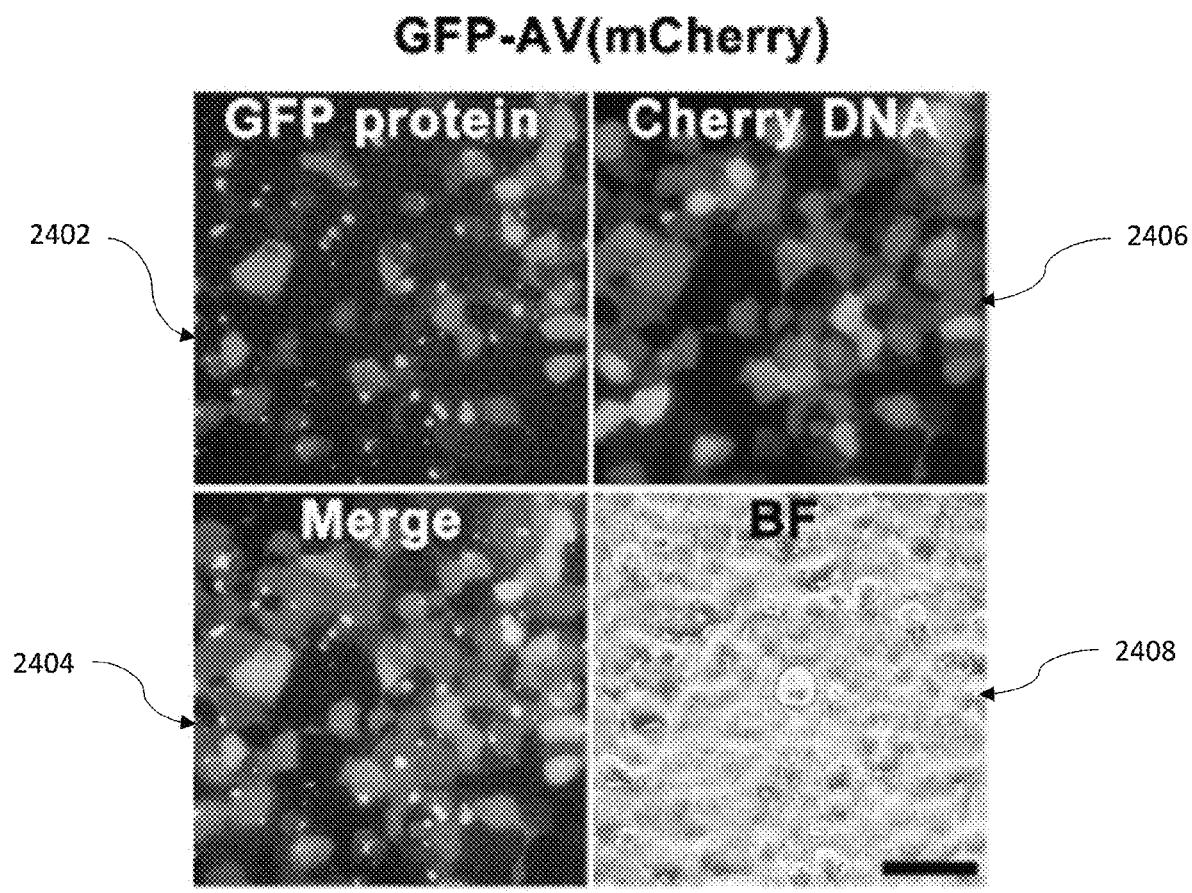
FIG. 24 is a graph showing the internalization of GFP protein and expression of mCherry DNA according to one exemplary embodiment of the present invention.
Figure 25:
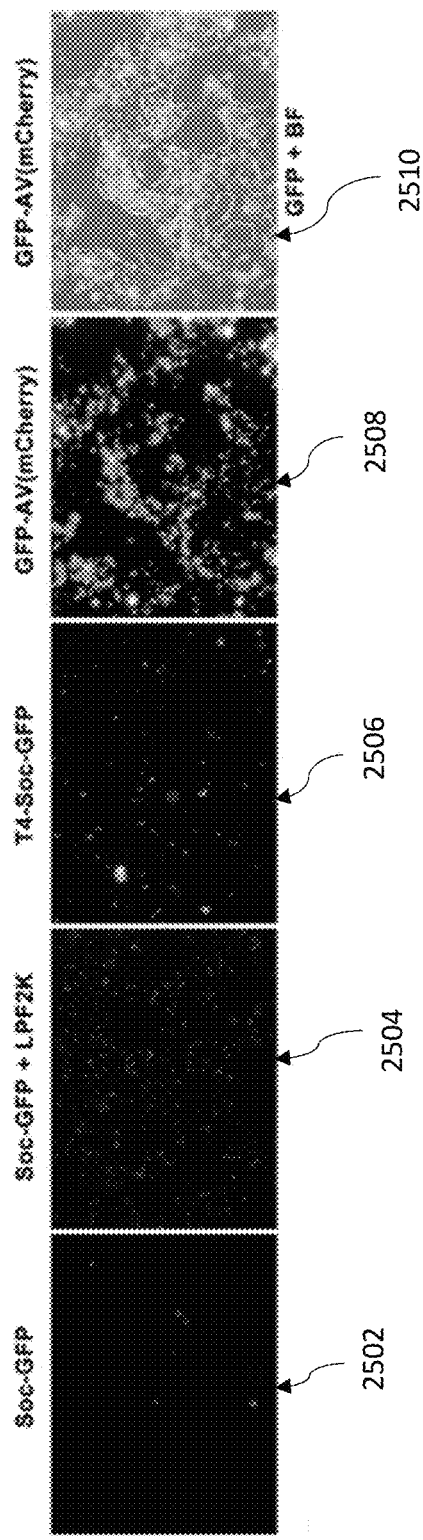
FIG. 25 is a graph showing the internalization of GFP protein at 3 h after treatment according to one exemplary embodiment of the present invention.
Figure 26:
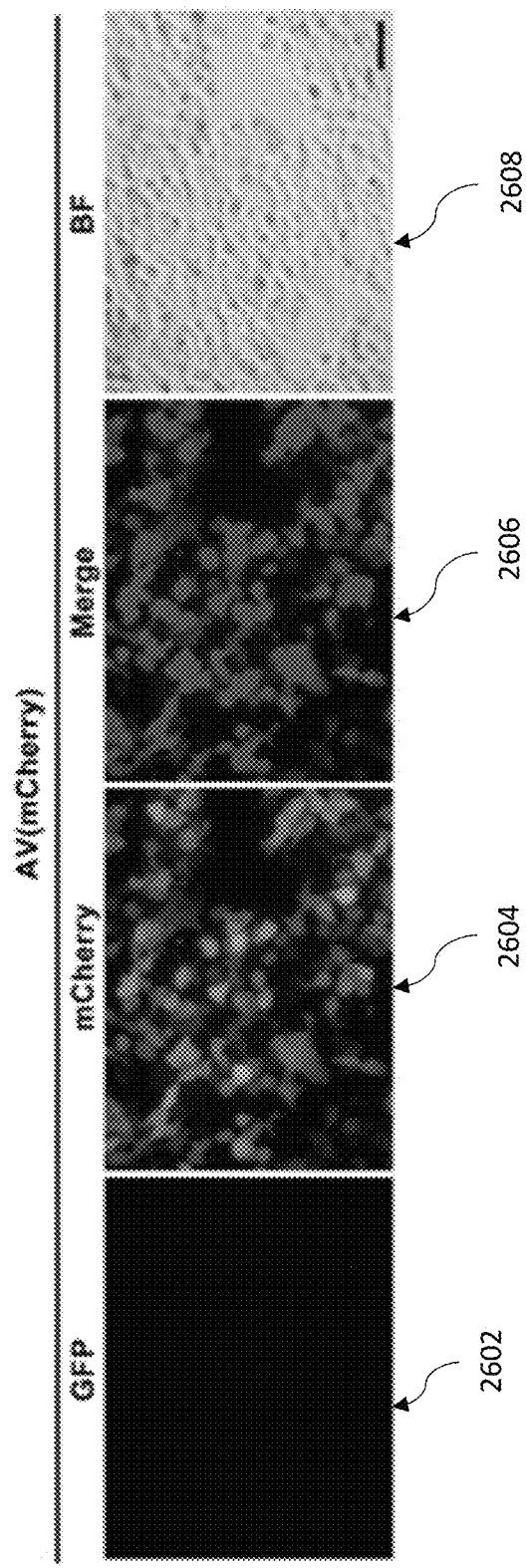
FIG. 26 is a graph showing the expression of mCherry DNA according to one exemplary embodiment of the present invention.

In one embodiment, all the AVs in the present disclosure efficiently co-delivered the displayed proteins as well as the packaged plasmids in a functional state. For instance, when exposed to 293 cells, the GFP-displayed AVs show strong green fluorescence, initially at the cell surface (~3 hr) and then throughout the cell (~20 hr). When the same AVs are also packaged with mCherry reporter plasmid, the cells in addition began showing red fluorescence at 6 hr and continued to intensify up to 48 hr, due to the expression of the delivered mCherry gene. FIG. 23 shows the quantification of packaged mCherry reporter plasmid (2302) for T4-AVs and the quantification of packaged backbone of plasmid pAAV-mCherry (2304) at different DNA to T4 ratio. The linearized DNAs are incubated with T4 at increasing DNA-to-capsid ratios as indicated at the top of the panels. Maximum packaging capacity reached at a ratio of 15-20:1. FIG. 24 shows the fluorescence of internalized GFP protein (2402) and expression of mCherry (2406) DNA in cells following delivery by T4(mCherry)-Soc-GFP-AVs. A merged view (2404) of both GFP and mCherry as well as a bright field (BF) view (2404) are also shown in FIG. 24. FIG. FIG. 25 shows representative fluorescent images of cells at 3 h after treatment with Soc-GFP (2502), Soc-GFP+LPF2K (simple mixture) (2504), T4-Soc-GFP (2506), or T4-Soc-GFP-AVs (2508). The right panel (2510) shows the merged image of GFP signal and bright field (BF), suggesting the displayed GFP protein efficiently attached to the cell surface at 3 h after AV transduction. FIG. 26 shows mCherry DNA delivery using T4(mCherry)-AVs where only mCherry expression is observed. In FIG. 26, GFP expression (control) (2602), expression (2604), merged view of GFP and mCherry (2606) as well as BF view (2608) are shown.

Figure 27:
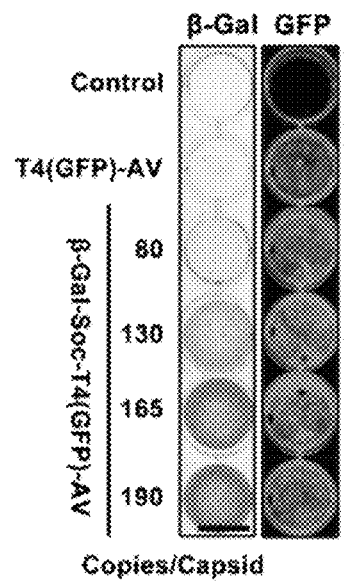
FIG. 27 is a graph showing β-galactosidase enzyme activity and GFP expression according to one exemplary embodiment of the present invention.
Figure 28:
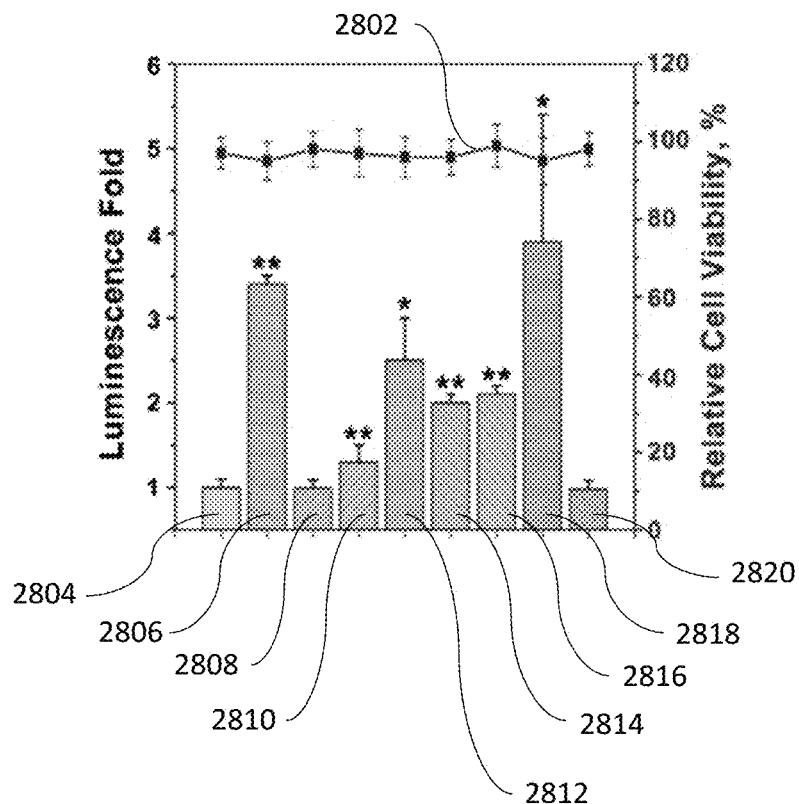
FIG. 28 is a graph showing comparison of T4-AV delivery using various displayed proteins according to one exemplary embodiment of the present invention.

In one embodiment, cells transduced with AVs displaying ~516 kDa tetrameric β-galactosidase (β-Gal) and packaged with Luci or GFP reporter plasmids, exhibit both the β-galactosidase activity and luciferase/GFP activity in a dose-dependent manner, as shown in FIGS. 27 and 28. FIG. 27 shows β-galactosidase enzyme activity and GFP expression examined following delivery by T4(GFP)-Soc-β-Gal-AVs at increasing copy numbers of displayed Soc-β-galactosidase. As shown in FIG. 27, the β-galactosidase enzyme activity and GFP expression increase with the increasing ratio of copies of β-galactosidase protein or GFP plasmid to T4 capsid.

Figure 29:
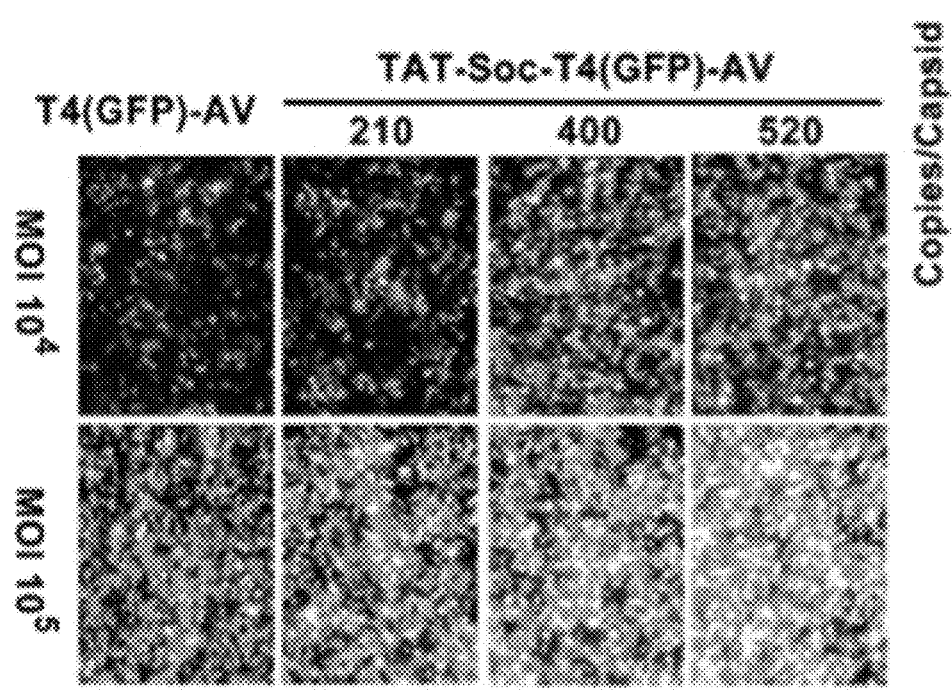
FIG. 29 is a graph showing transduction of TAT-displayed T4-AVs at different copy numbers of TAT per capsid and at different MOI according to one exemplary embodiment of the present invention.
Figure 30:
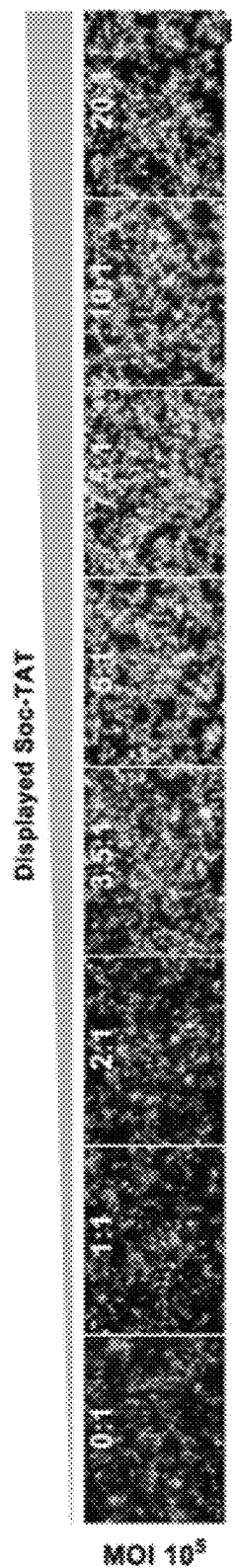
FIG. 30 is a graph showing increased delivery efficiency of T4(GFP)-AVs into 293 cells with Soc-TAT decoration according to one exemplary embodiment of the present invention.

Somewhat unexpectedly, as shown in FIG. 28, AVs with displayed proteins, including Soc-TAT (2806), GFP-Soc (2808), Cre-Soc (2810), β-Gal-Soc (2812), Cpf1-Soc (2814) (SEQ ID NO: 17), Cas9-Soc (2816) (SEQ ID NO: 16), RGD-Hoc (2818) (SEQ ID NO: 19), and Cre-Hoc (2820) (SEQ ID NO: 18), in general show enhanced transduction efficiency, as measured by the luciferase activity, when compared to control AVs (2804) having no displayed protein probably because the displayed protein molecules contributed additional charges that result in better lipid coating and/or cell binding. Consistent with this notion, more positively charged proteins such as TAT (2806), Cas9 (2816), and Cpf1 (2814) show greater enhancement, with the TAT-AVs having high copy number (520 Copies) and high positive charge of TAT showing the highest enhancement, ~3.5-fold. FIG. 29 shows representative fluorescence images depicting enhanced transduction of TAT-displayed T4-AVs at different copy numbers of TAT per capsid and at different ratios of T4-AV nanoparticles per cell. FIG. 30 shows Soc-TAT decoration increases the delivery efficiency of T4(GFP)-AVs into 293 cells. Soc-TAT molecules are displayed on T4(GFP) capsid at increasing ratios of Soc-TAT molecules to Soc binding sites (0:1to 20:1). As shown in FIG. 30, the delivery efficiency increases with the increasing ratios of Soc-TAT molecules to Soc binding sites. The resultant T4(GFP)-Soc-TAT-AVs are transduced into cells at a ratio of $10^5$ T4-AVs per cell. The GFP fluorescence is observed at 20 h post transduction.

The 9-aa disulphide-constrained RGD peptide (CDCRGDCFC) (2818 and 3104), a cell surface binding ligand, when fused to the tip of Hoc fiber showed even greater enhancement, compared to control AVs (T4(Luci)-AV) (2804 and 3102). The blue line (2802) in the top of FIG. 28 shows that cell viability of cells treated with T4-AV particles with various displayed proteins remains at about 100%.

Figure 31:
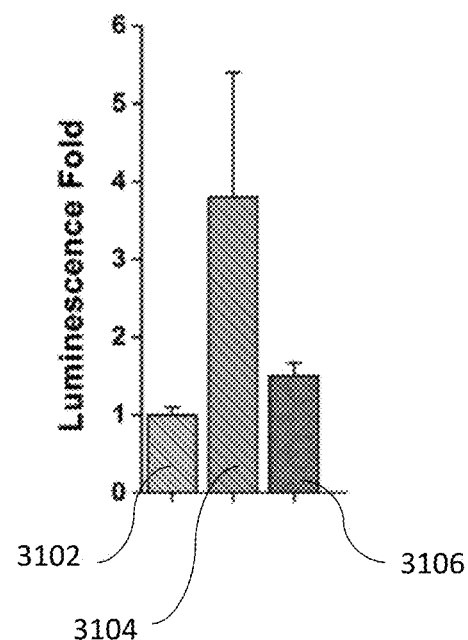
FIG. 31 is a graph showing enhanced transduction by T4-AVs displayed with integrin-binding RGD motif according to one exemplary embodiment of the present invention.

This tripeptide motif (RGD peptide) has been well-documented to bind to the abundantly present integrin molecules on human cells[8]. Furthermore, the luciferase activity of the Hoc-fused RGD (RGD-Hoc-T4(Luci)-AV) (3104) is ~5-fold higher than the Soc-fused RGD (RGD-Soc-T4(Luci)-AV) (3106), as shown in FIG. 31, even though the copy number of Soc-RGD is 8.3-fold greater than that of RGD-Hoc. It appears that the targeting ligand attached to the tip (N-terminus) of ~17 nm-long flexible Hoc fiber imparts much greater reach to capture the integrin receptor molecules than the Soc-fused RGD that is bound to the capsid wall.

Genome Editing Artificial Viruses

Ability to "program" AVs with combinations of genes and proteins can be used to perform complex molecular operations in human cells, which would open a vast array of therapeutic applications[7,62].

In one embodiment, a variety of genome editing AVs are assembled by incorporating all the editing molecules into the same AV in different configurations, summarized in the table below.

| | Payloads of genome editing T4-AVs | |
|---|---|---|
| | Packaged inside | Displayed outside |
| 1 | Cas9; gRNA; GFP | — |
| 2 | gRNA; GFP | Cas9 |
| 3 | GFP | Cas9-gRNA(RNP) |
| 4 | Cas9; gRNA; GFP | Cas9-gRNA(RNP) |
| 5 | Cas9; gRNA1; gRNA2 | RNP1; RNP2 |

In a preferred embodiment, AVs packaged with plasmids carrying expressible Cas9 and gRNA genes under the control of CMV and U6 promoters, respectively, are assembled. Cas9 sequence is codon-optimized and fused with the nuclear localization sequence (NLS) PKKKRKV at its N-terminus (NLS-Cas9). This allows the transport of cytosol-delivered Cas9 into the nucleus to carry out genome editing. The gRNA is targeted to the PPP1R12C locus on chromosome 19 of the human genome, also known as the AAVS1 safe harbor locus[10]. On average, each capsid is packaged with 7 molecules of the 8.3 Kbp plasmid containing both the expression cassettes.

In another embodiment, AVs are assembled by incorporating purified Cas9 as displayed protein fused to Soc (NLS-Cas9-Soc), while the gRNA is supplied as a packaged plasmid. The purified NLS-Cas9 (panel A of FIG. 32) and NLS-Cas9-Soc (panel B of FIG. 32) are obtained using size-exclusion chromatography and the purification of NLS-Cas9 and NLS-Cas9-Soc is confirmed by SDS-PAGE, as shown in FIG. 32.

Figure 32:
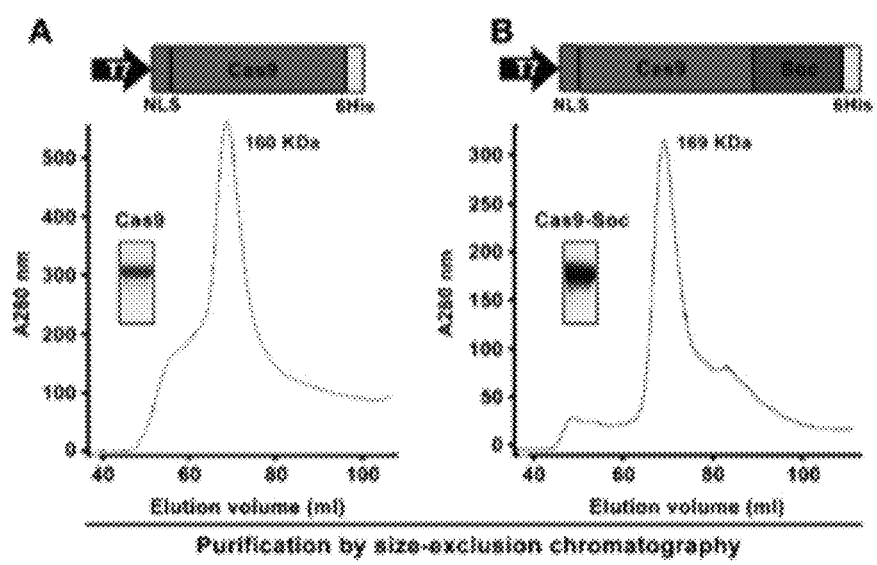
FIG. 32 is a schematic diagram showing expression and purification of NLS-Cas9 and NLS-Cas9-Soc according to one exemplary embodiment of the present invention.

FIG. 32 shows the expression cassette schematics and size-exclusion chromatography profiles of Cas9 and Cas9-Soc, respectively. Soc is fused to the C terminus of Cas9. Both Cas9 and Cas9-Soc contain an N-terminal SV40 nuclear localization signal (NLS) and a C-terminal His tag. The proteins are over-expressed in *E. coli* using the T7 promoter and purified by HisTrap affinity chromatography and size-exclusion chromatography. The purified Cas9 and Cas9-Soc exist as monomers, as evident from the molecular size determined using the respective elution volumes. The purified proteins are analyzed by SDS-PAGE as shown in the inserts.

Figure 33:
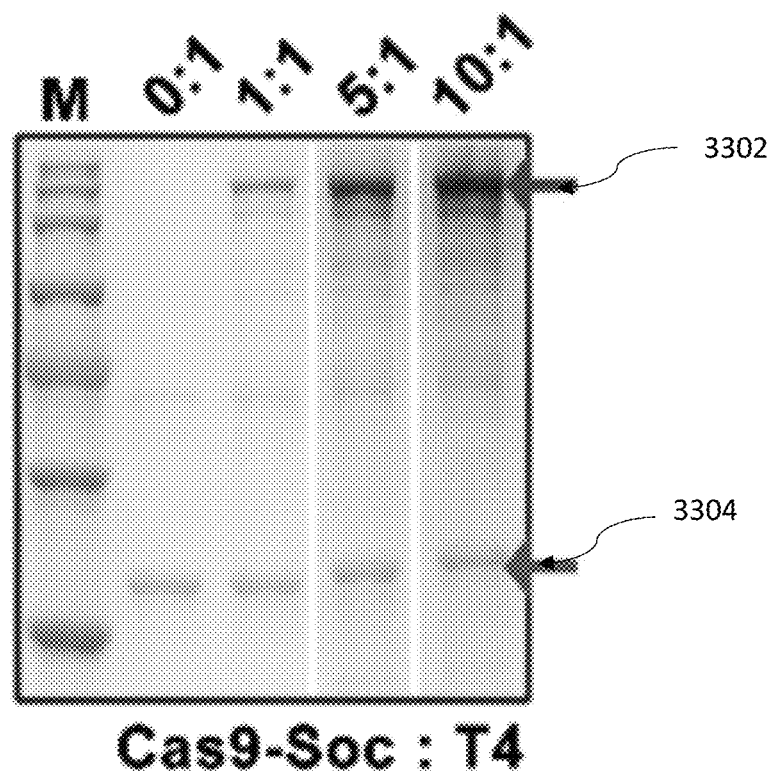
FIG. 33 is a graph showing the quantification of Cas9-Soc (SEQ ID NO: 16) displayed on T4 capsid according to one exemplary embodiment of the present invention.
Figure 34:
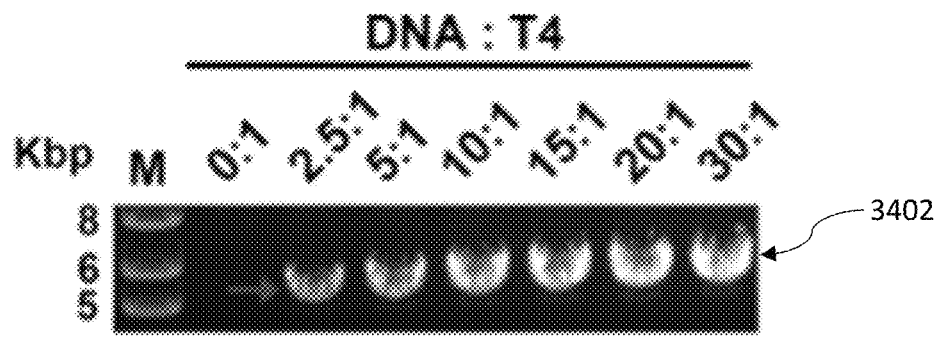
FIG. 34 is a graph showing the quantification of packaged gRNA for T4-AVs according to one exemplary embodiment of the present invention.

Up to about 550 molecules of Cas9 could be displayed on the surface when the assembly mixture contains Cas9 (3302) at a ratio of 10 molecules to one Soc binding site, as shown in FIGS. 33, and ~10 copies of gRNA plasmid (3402) are packaged inside the capsid, as shown in FIG. 34. FIG. 33 also shows the display of Cas9-Soc on T4 capsid at increasing ratios of Cas9-Soc molecules to Soc-binding sites. The positions of Cas9-Soc (3302) and gp23* (3304) bands on an SDS-gel are shown.

Figure 35:
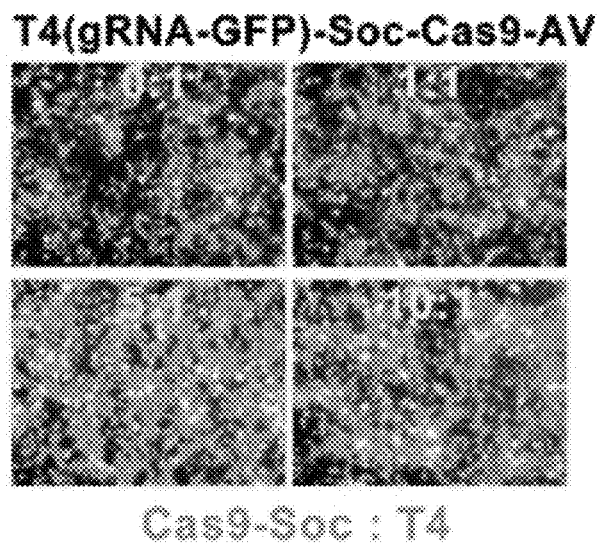
FIG. 35 is a microscopy image showing enhanced GFP reporter expression according to one exemplary embodiment of the present invention.

In another embodiment, a second GFP reporter plasmid is packaged into both these AVs to confirm that the AV transduction is at near 100% efficiency, a benchmark for all T4-AV studies in the present disclosure, as shown in FIG. 35. As shown in FIG. 35, fluorescence microscopy images show enhanced GFP reporter expression with increasing copy number of displayed Cas9.

Figure 36:
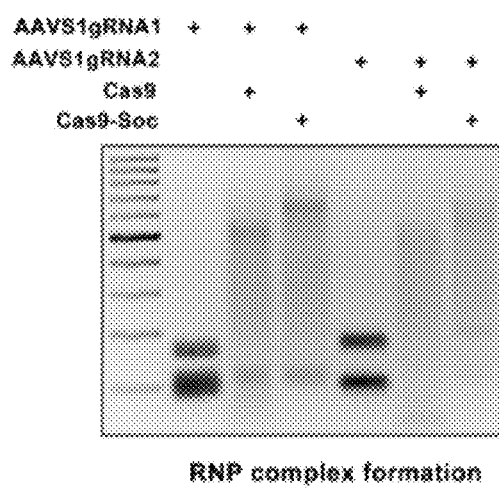
FIG. 36 is a graph showing the formation of Cas9-gRNA ribonucleoprotein (RNP) complexes according to one exemplary embodiment of the present invention.
Figure 37:
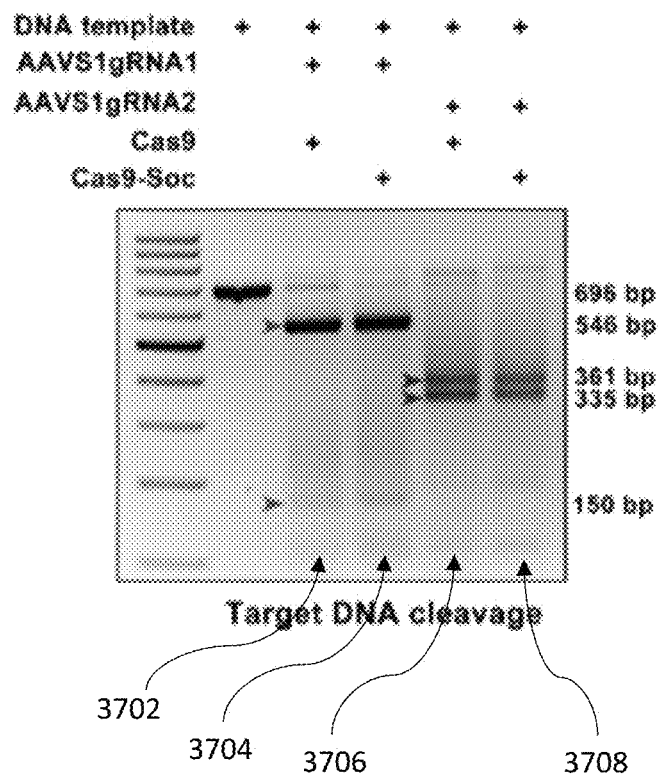
FIG. 37 is a graph showing the gRNA-directed cleavage of target DNA according to one exemplary embodiment of the present invention.
Figure 38:
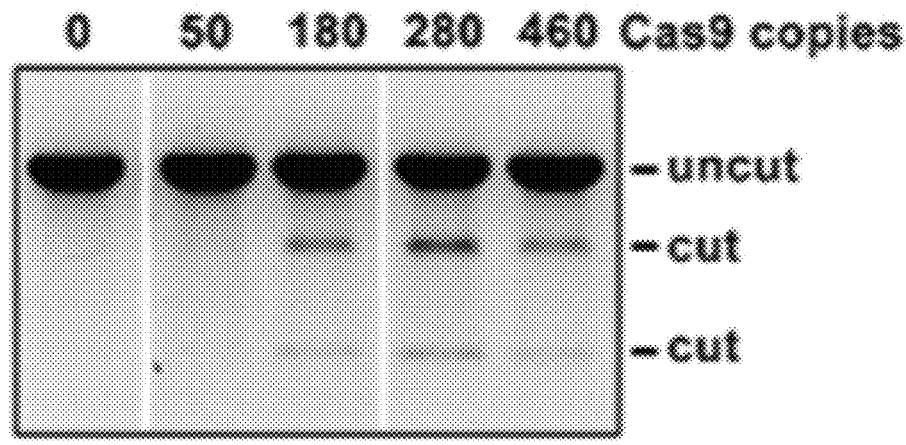
FIG. 38 is a graph showing the disruption of endogenous AAVS1 locus according to one exemplary embodiment of the present invention.
Figure 39:
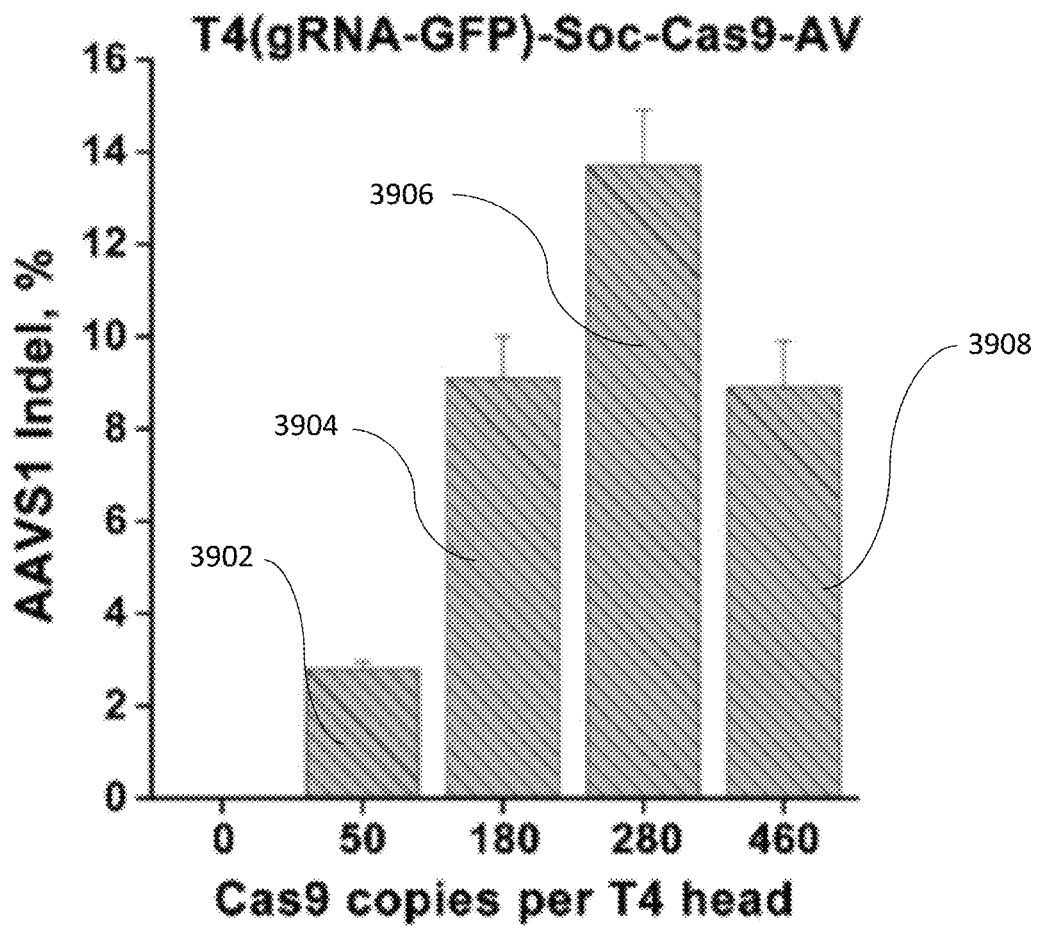
FIG. 39 is a graph showing the efficiency of genome editing according to one exemplary embodiment of the present invention.

Furthermore, a series of biochemical assays are performed to ensure that Cas9 and gRNAs exhibited full functionality, i.e., formation of Cas9-gRNA ribonucleoprotein (RNP) complexes and gRNA-directed cleavage of target DNA, as shown in FIGS. 36 and 37. The binding test of Cas9 and Cas9-Soc to AAVS1 gRNA1 or gRNA2, as determined by gel retardation assay. As shown in FIG. 37, Cas9 (3702 and 3706) and Cas9-Soc (3704 and 3708) showed comparable levels of DNA cleavage activity at the specific gRNA targeted sites. These AVs when transduced into 293 cells carry out genome editing by introducing double-stranded breaks at the targeted AAVS1 locus followed by repair by non-homologous end joining (NHEJ) which create short insertions and deletions (indels) at the target site, as determined by T7 Endonuclease I (T7EI) assay, as shown in FIG. 38, and confirmed by DNA sequencing (not shown). FIG. 38 shows the disruption of endogenous AAVS1 locus following AV-mediated delivery of Cas9 protein and gRNA-expressing plasmid DNA. Indel mutations are detected by the T7E1 assay three days after the transduction. FIG. 39 shows AAVS1 indel efficiency of T4-AVs displayed with various copy numbers of Cas9, including 50 copies (3902), 180 copies (3904), 280 copies (3906) and 460 copies (3908). The optimal efficiency of genome editing is ~12 to 15%, when the Cas9 copies per T4 capsid is about 280 (3906).

Figure 40:
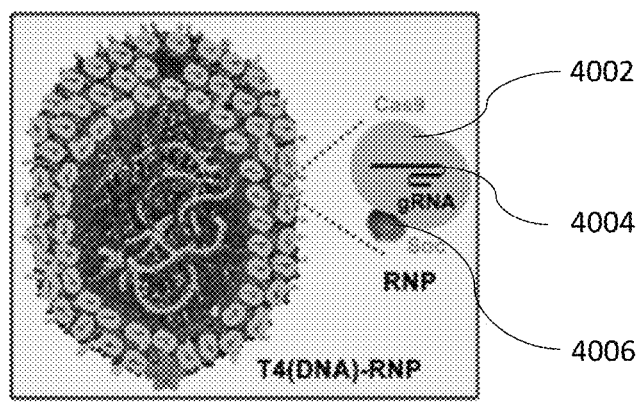
FIG. 40 is a schematic diagram showing genome editing AVs according to one exemplary embodiment of the present invention.
Figure 41:
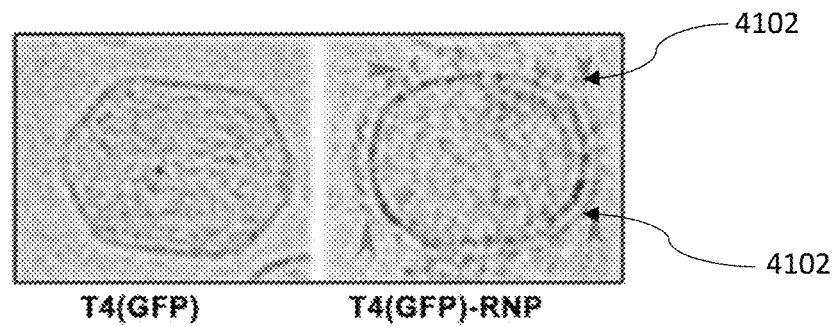
FIG. 41 is an EM photo showing the presence of genome editing complexes decorating the Capsid according to one exemplary embodiment of the present invention.
Figure 42:
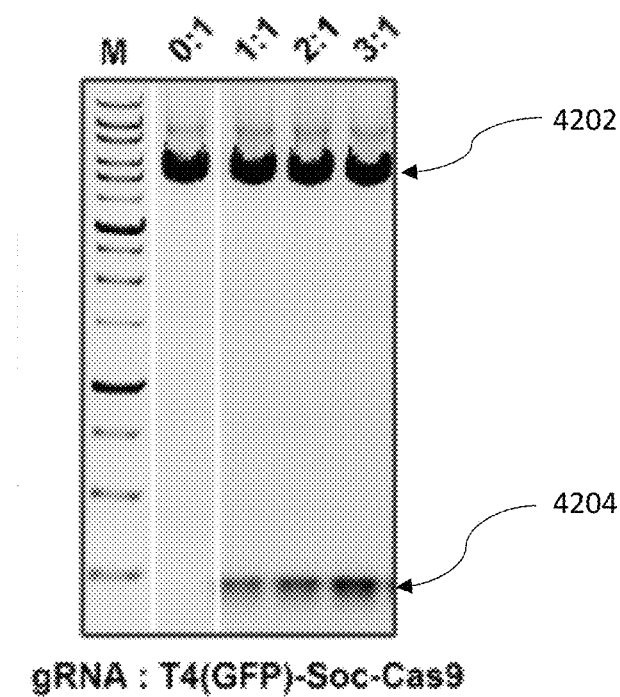
FIG. 42 is a graph showing the binding of gRNA to T4(GFP)-Soc-Cas9 capsids increases with increasing ratios of gRNA molecules to Soc binding sites according to one exemplary embodiment of the present invention.
Figure 43:
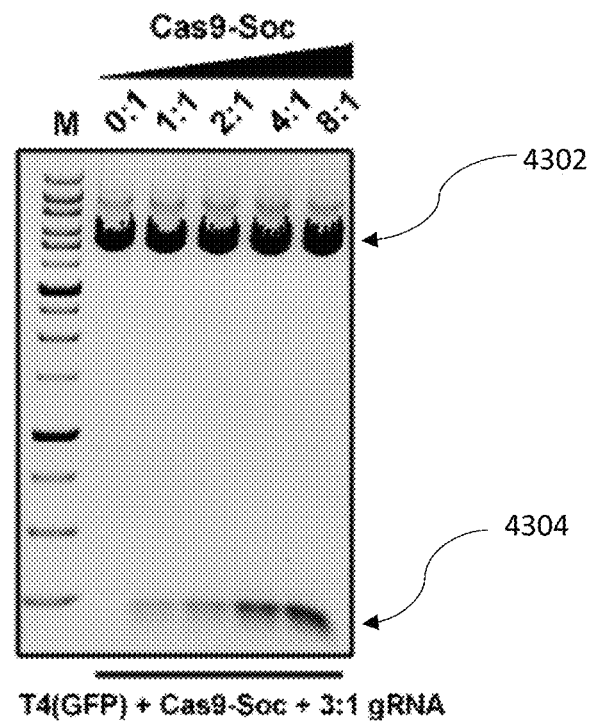
FIG. 43 is a graph showing the binding of gRNA to T4(GFP)-Soc-Cas9 increases by increasing the ratio of Cas9-Soc molecules to Soc binding sites according to one exemplary embodiment of the present invention.
Figure 44:
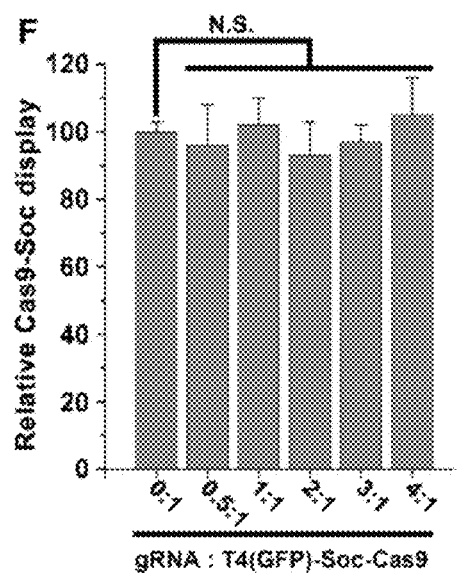
FIG. 44 is a graph showing the impact of binding of gRNA to T4(GFP)-Soc-Cas9 on the display of Cas9-Soc on T4 according to one exemplary embodiment of the present invention.

In another embodiment, AVs are assembled by incorporating Cas9 (4002) and gRNA (4004) fused to Soc (4006) as a pre-formed ribonucleoprotein (RNP) complex, as shown in FIG. 40. Negative EM showed the presence of genome editing complexes decorating the Capsid (4102), as shown in FIG. 41. About 280 copies of ~210 kDa Cas9-gRNA RNP complex are displayed on the capsid through Soc. As shown in FIG. 42, binding of gRNA (4204) to T4(GFP)-Soc-Cas9 capsids increases with increasing ratios of gRNA molecules to Soc binding sites, while the amount of GFP (4202) remains constant at all ratios. As shown in FIG. 43, binding of gRNA (4304) to T4(GFP)-Soc-Cas9 increases by increasing the ratio of Cas9-Soc molecules to Soc binding sites, while the amount of GFP (4302) remains constant at all ratios. FIG. 44 shows the binding of gRNA to T4(GFP)-Soc-Cas9 did not affect the display of Cas9-Soc on T4, as the relative Cas9-Soc display does not significantly (N.S.) change at all gRNA to T4(GFP)-Soc-Cas9 ratios.

In another embodiment, an additional ~7 molecules of Cas9-gRNA expression plasmid are packaged into the same AV.

Figure 45:
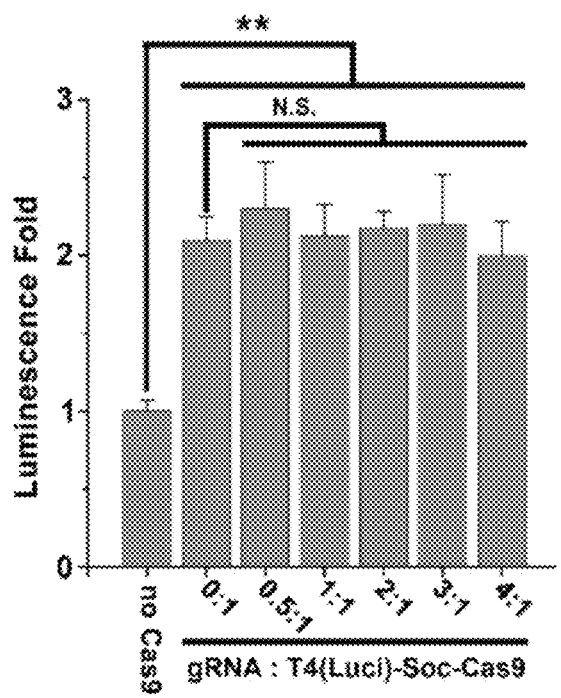
FIG. 45 is a graph showing the comparison of luciferase activity in cells treated with T4(Luci)-AVs or T4(Luci)-Soc-Cas9-gRNA-AVs at increasing gRNA binding ratio according to one exemplary embodiment of the present invention.
Figure 46:
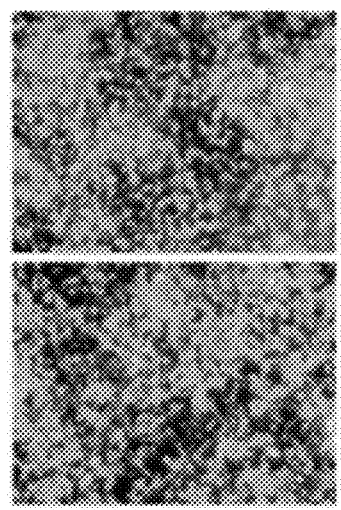
FIG. 46 is a graph showing representative fluorescence images of cells treated with T4(GFP)-Soc-Cas9-AVs and T4(GFP)-Soc-Cas9-gRNA-AVs according to one exemplary embodiment of the present invention.

In the above embodiments, either GFP or Luci reporter plasmids are also packaged to confirm near 100% transduction efficiency. FIG. 45 shows comparison of luciferase activity in cells treated with T4(Luci)-AVs or T4(Luci)-Soc-Cas9-gRNA-AVs at increasing gRNA binding ratio (0:1 to 4:1). The luciferase activity of T4(Luci)-Soc-Cas9-gRNA-AVs delivery is normalized to T4(Luci)-AVs and presented as the fold change. As shown in FIG. 45, T4(Luci)-Soc-Cas9-gRNA-AVs enhanced transduction efficiency, compared to T4(Luci)-AVs. FIG. 46 shows representative fluorescence images of cells treated with T4(GFP)-Soc-Cas9-AVs and T4(GFP)-Soc-Cas9-gRNA-AVs, which both show high transduction efficiency.

Figure 47:
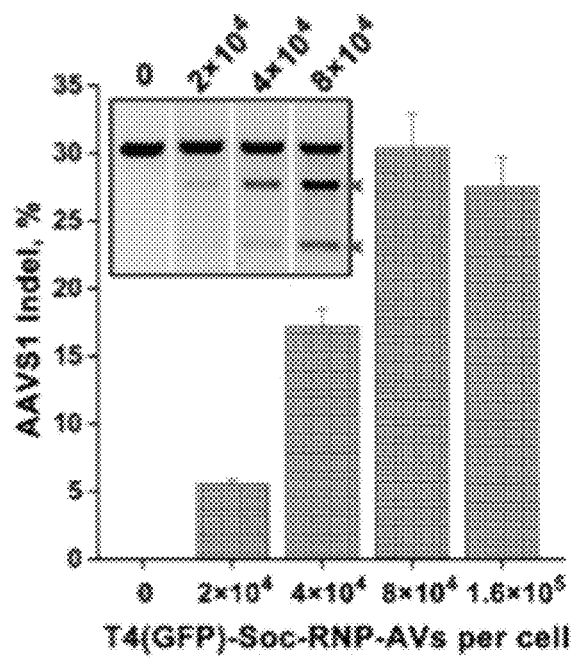
FIG. 47 is a graph showing the genome editing at the AAVS1 locus by RNP-AVs delivered at different ratios of AV nanoparticles to cells according to one exemplary embodiment of the present invention.
Figure 48:
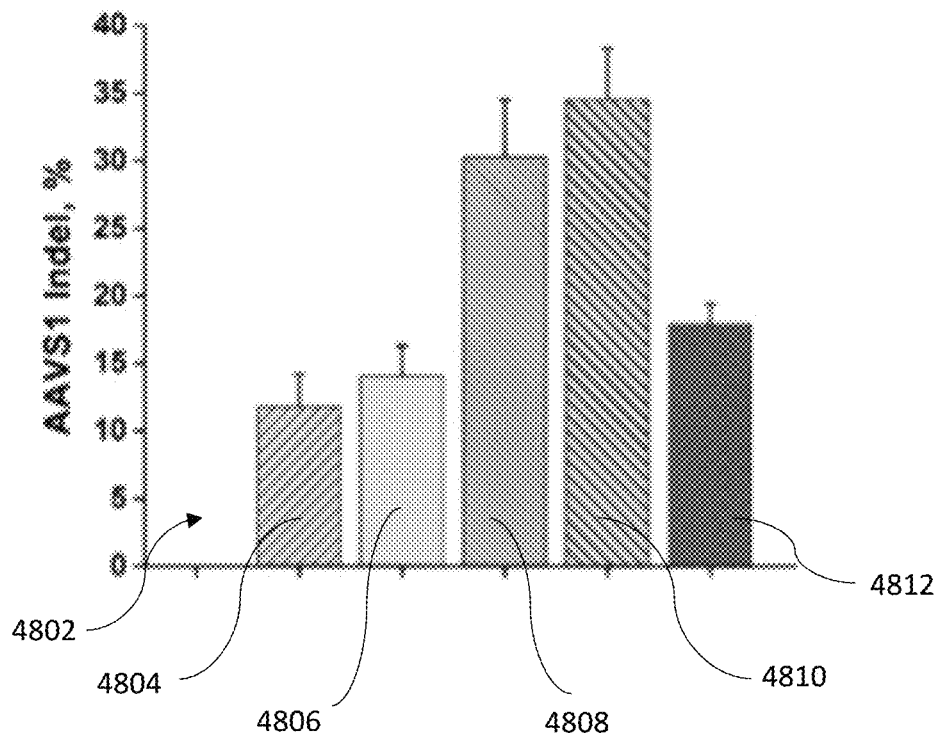
FIG. 48 is a graph showing the comparison of AAVS1 indel efficiencies using T4-AVs in different configurations according to one exemplary embodiment of the present invention.

In one embodiment, the AVs with soc-fused proteins give the best editing efficiencies, ~30-35% disruption and indels at the AAVS1 locus, about twice that obtained by lipofectamine transfection, as shown in FIGS. 47 and 48. FIG. 47 shows genome editing at the AAVS1 locus by RNP-AVs delivered at different ratios of AV nanoparticles to cells, as determined using T7E1 assay. FIG. 48 shows comparison of AAVS1 indel efficiencies using T4-AVs in different configurations, including T4-AV (4802), T4(Cas9-gRNA)-AV (4804), T4(gRNA-GFP)-Cas9-AV (4806), T4(GFP)-Soc-RNP-AV (4808), T4(Cas9-gRNA)-Soc-RNP-AV (4810), and Cas9-gRNA plasmid+Lip (4812). Empty T4-AVs and lipofectamine transfection (Lip) of Cas9-gRNA-plasmid are used as negative and positive controls, respectively.

Figure 49:
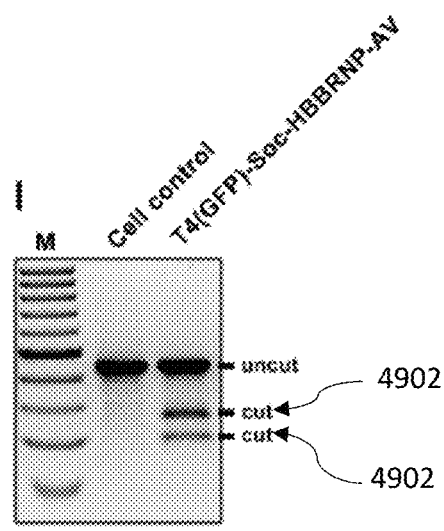
FIG. 49 is a graph showing HBB gene disruption mediated by T4(GFP)-Soc-Cas9-HBBgRNA-AVs according to one exemplary embodiment of the present invention.

In one embodiment, genome editing is performed at a therapeutically important site, by targeting the AVs to hemoglobin beta gene (HBB) on chromosome 11 of the human genome. AVs assembled with Cas9-HBB gRNA RNP complexes performed ~20-25% editing at this site, as shown in FIG. 49. In FIG. 49, T7E1 assay shows HBB gene disruption (4902) mediated by T4(GFP)-Soc-Cas9-HBBgRNA-AVs.

Figure 50:
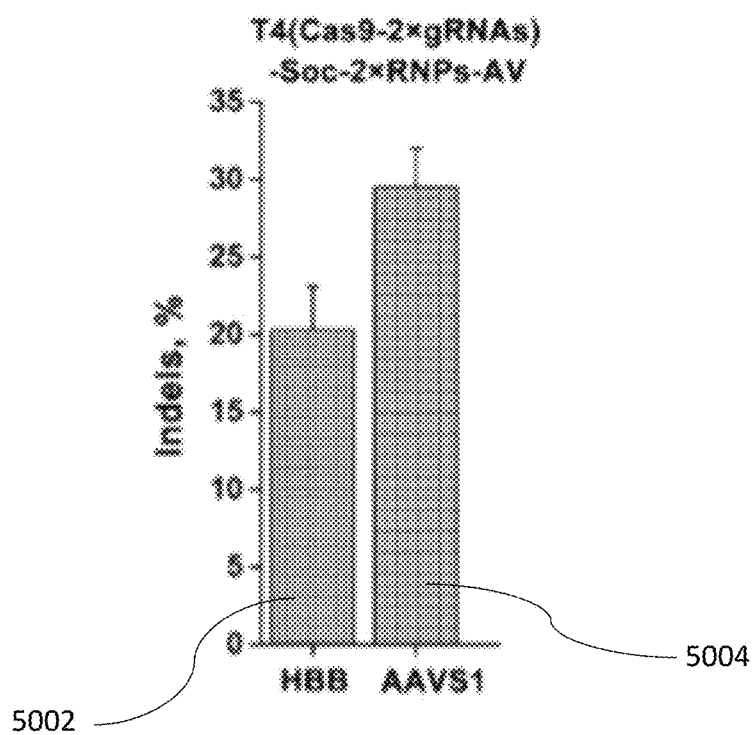
FIG. 50 is a graph showing simultaneous genome editing at two target sites on human genome by T4-AVs according to one exemplary embodiment of the present invention.

In another embodiment, simultaneous editing at more than one site on the human genome is achieved by displaying two gRNAs, one targeted to HBB and another to AAVS1, on the same AV, as shown in FIG. 50. These AVs also carried ~7 molecules of Cas9 and HBB/AAVS1gRNA expression plasmids. As shown in FIG. 50, these multiplex AVs successfully performed genome editing of the respective target sites, ~20% at the HBB site (5002) and ~30% at the AAVS1 site (5004).

Gene Recombination Artificial Viruses

Figure 51:
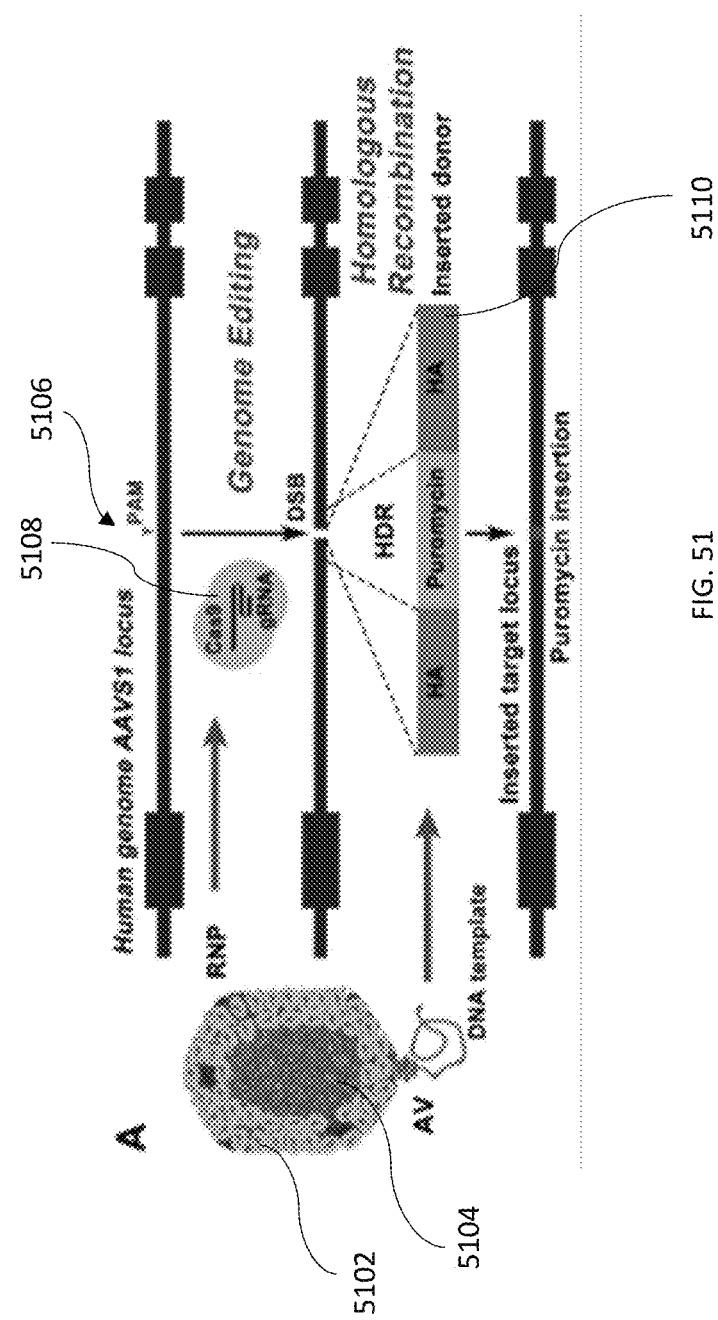
FIG. 51 is a schematic diagram showing the design of AV-mediated genome editing and homologous recombination at the AAVS1 locus according to one exemplary embodiment of the present invention.
Figure 52:
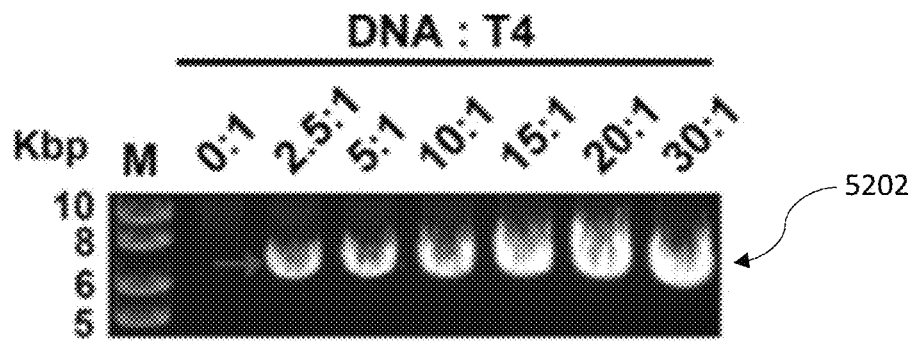
FIG. 52 is a graph showing the quantification of packaged puromycin plasmid DNA for T4-AVs according to one exemplary embodiment of the present invention.
Figure 53:
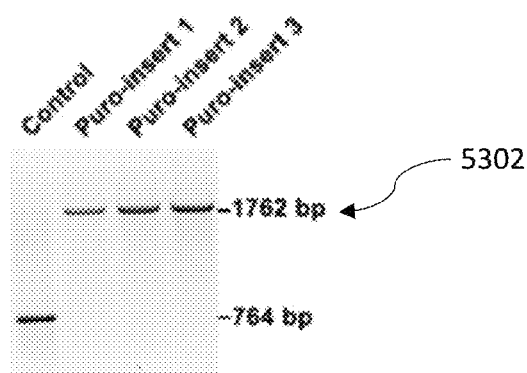
FIG. 53 is a graph showing the PCR assay on puromycin resistant single cell clones following transduction with T4(Puro-donor)-Soc-Cas9-gRNA-AVs according to one exemplary embodiment of the present invention.
Figure 54:
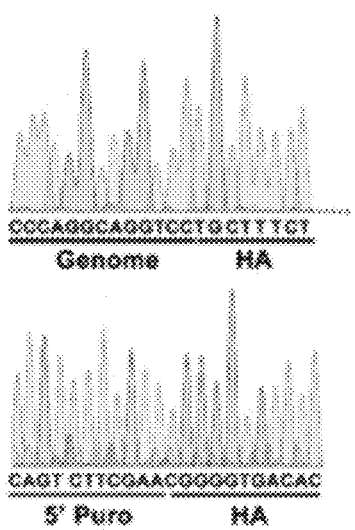
FIG. 54 is a graph showing DNA sequencing of the PCR amplicon confirming the presence of puromycin donor insertion at the target site in each of the clones according to one exemplary embodiment of the present invention.
Figure 55:
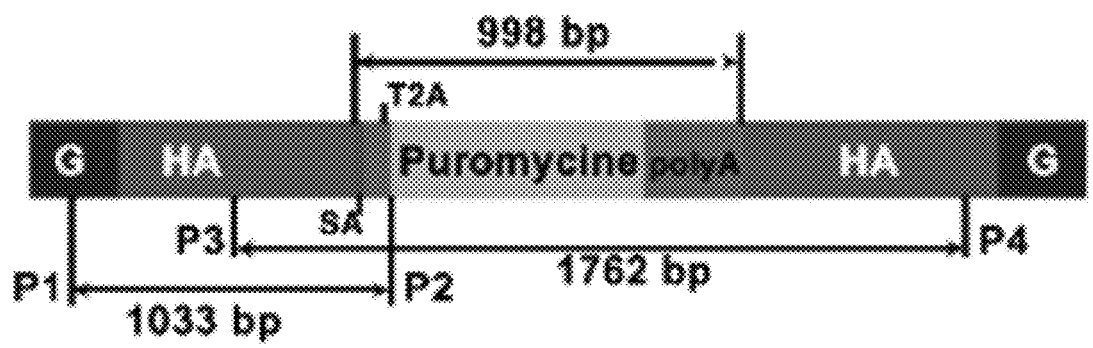
FIG. 55 is a schematic diagram showing the locations of PCR amplification primer sets for detecting targeted insertions according to one exemplary embodiment of the present invention.

In one embodiment, the T4-AVs can perform genome editing as well as gene recombination, homologous or site-specific, in the same cell. Previously, it was reported that Cas9-generated DNA breaks facilitate homologous recombination near the cleaved site[6,28]. In a preferred embodiment, AVs are assembled by displaying AAVS1-targeted Cas9-gRNA RNP complexes (5102) on capsid and a donor plasmid containing promoter-less puromycin resistant gene (Puro) (5104) packaged inside, as shown in FIG. 51. AV-mediated genome editing and homologous recombination at the AAVS1 locus (5106) is designed by delivering Cas9-gRNA RNP complex (displayed) (5108) and donor puromycin plasmid DNA (packaged) (5110). The donor plasmid also had ~800 bp homologous arms flanking the Cas9 cleavage site. FIG. 52 shows the quantification of packaged puromycin plasmid DNA (5202) for T4-AVs. Puromycin resistance will emerge if homologous recombination occurred following Cas9 cleavage, bringing the Puro gene under the control of an upstream AAVS1 promoter, as shown in FIG. 51. Indeed, puromycin resistance clones arise following transduction by these AVs, whereas control AVs lacking the RNP complex showed no puromycin resistance. PCR and DNA sequencing show that 15 out 15 isolated single cell clones exhibiting puromycin resistance contained Puro gene (5302) insertion precisely at the Cas9 cleavage site, as shown in FIGS. 53 and 54 (FIGS. S5A and S5B). In the PCR assay, primers corresponding to the flanking AAVS1 gene were used for PCR. Three representative clones are shown in FIG. 53, all depicting homozygous recombination at the target site. FIG. 55 shows the locations of PCR amplification primer sets (P1 and P2, P3 and P4) for detecting targeted insertions. The sequences of the primer sets are:

```
P1:
                                    (SEQ ID NO: 12)
CTGCCGTCTCTCTCCTGAGT

P2:
                                    (SEQ ID NO: 13)
GTGGGCTTGTACTCGGTCAT

P3:
                                    (SEQ ID NO: 14)
AAAACTGACGCACGGAGGAA

P4:
                                    (SEQ ID NO: 15)
GTGGATTCGGGTCACCTCTC
```

Figure 56:
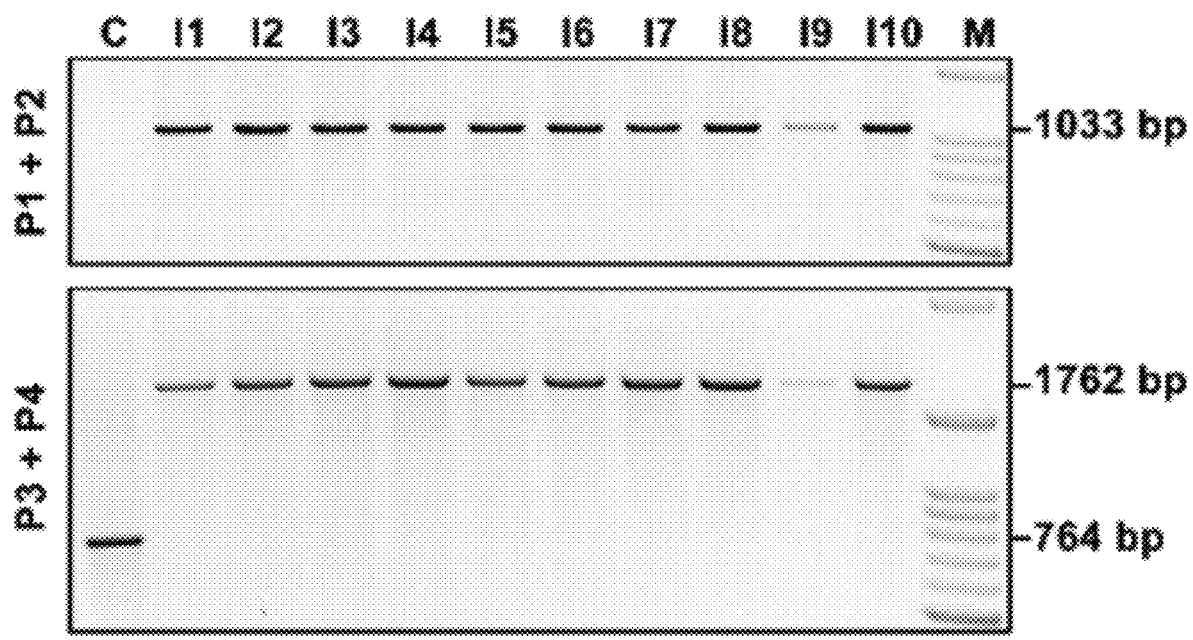
FIG. 56 is a graph showing the detection of amplified sequences according to one exemplary embodiment of the present invention.

In FIG. 55, SA is short for splice acceptor site; T2A is short for 2A cleavage peptide from *Thosea asigna* virus capsid protein. Using the primers schematic showed in FIG. 55, PCR assay of the AAVS1 gene is performed on the DNA isolated from single cell clones of T4(Puro-donor)-Soc-Cas9-gRNA-AVs treated cells. Ten representative single cell puromycin-resistant clones (I1 to I10) are analyzed using each primer set. The result of PCR assay is shown in FIG. 56, confirming the presence of the amplified sequences and, thus, the Puro gene.

Figure 57:
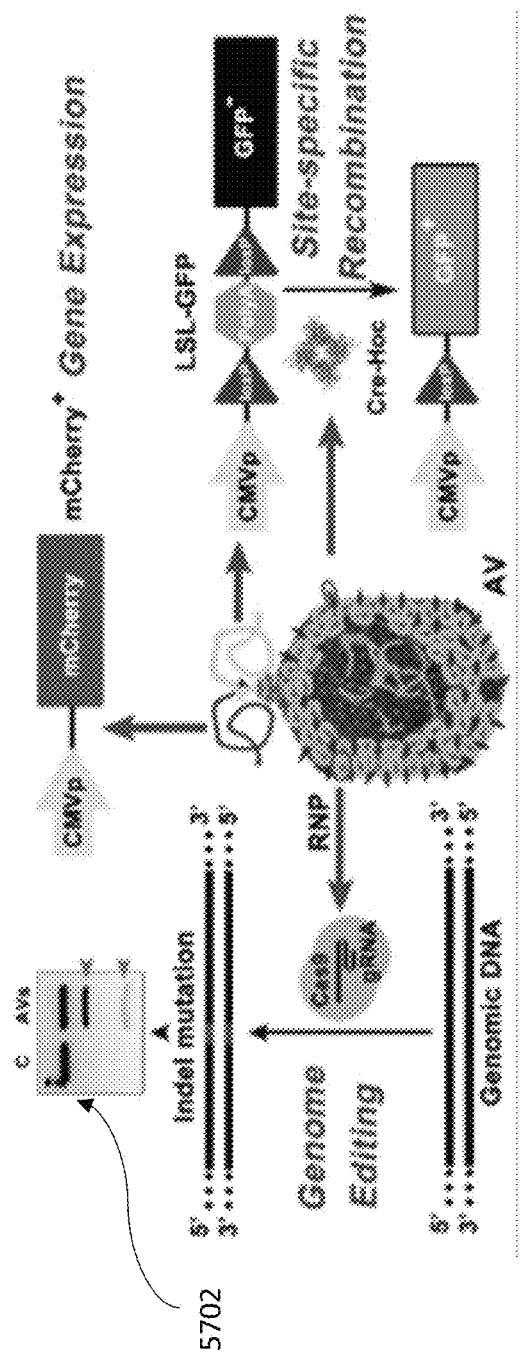
FIG. 57 is a schematic diagram showing the site-specific recombination by delivery of Cre-Hoc-T4(LSL-GFP+mCherry)-Soc-Cas9-gRNA-AVs according to one exemplary embodiment of the present invention.
Figure 58:
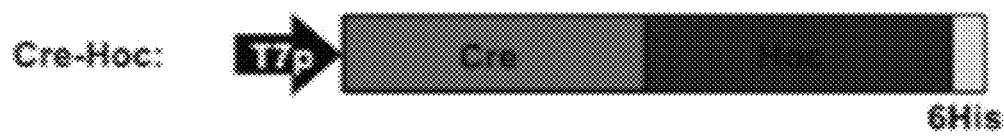
FIG. 58 is a schematic diagram showing the Cre-Hoc expression cassette according to one exemplary embodiment of the present invention.
Figure 59:
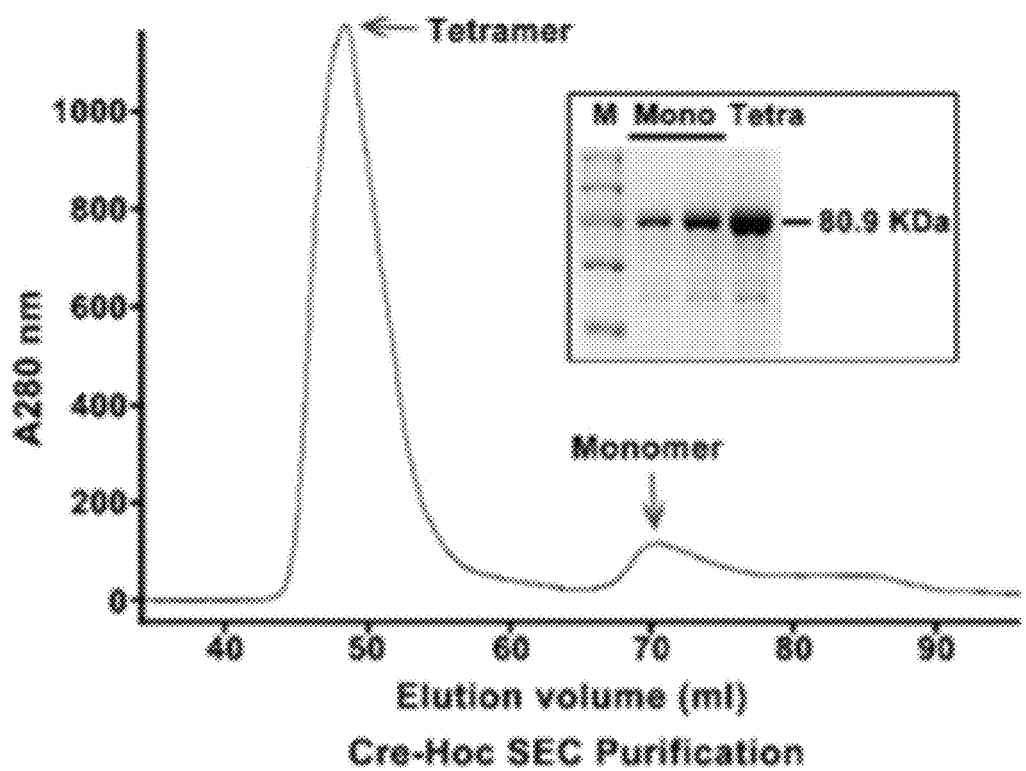
FIG. 59 is a graph showing the size-exclusion chromatography profile of Cre-Hoc protein according to one exemplary embodiment of the present invention.
Figure 60:
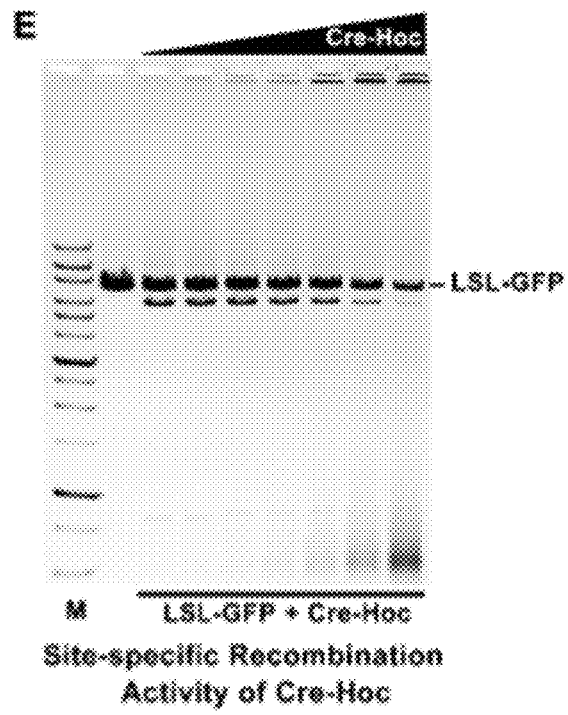
FIG. 60 is a graph showing the site-specific recombination activities of Cre-Hoc according to one exemplary embodiment of the present invention.

In one embodiment, AVs programmed with an even more complex set of payload molecules are assembled. The capsids are displayed with the site-specific recombinase Cre (with NLS at N-terminus) as Hoc fusion protein, and a plasmid containing CMV promoter-LoxP-polyA STOP-LoxP cassette upstream of the GFP reporter gene (LSL-GFP) is packaged inside the capsid, as shown in FIG. 57. T7E1 assay (5702) shown in the box indicates efficient and simultaneous genome editing by Cas9-gRNA RNP complex at an independent target site. The 34-bp LoxP sequences provide recombination sites for Cre. Successful site-specific recombination occurring between the LoxP sites splices out the polyA transcriptional STOP sequence and bring the GFP reporter under the control of the upstream CMV promoter, as shown in FIG. 57. FIG. 58 is a schematic of Cre-Hoc expression cassette. Hoc is fused to the C-terminus of Cre with a hexa-His tag and over-expressed in *E. coli* under the control of the T7 promoter. FIG. 59 shows the size-exclusion chromatography profile of Cre-Hoc protein. The red arrows indicate the eluted Cre-Hoc tetramer and monomer. The hatched box inside shows the SDS-PAGE analysis of Cre-Hoc tetramer and monomer. Both tetramer and monomer are active for phage display and site-specific recombination. Cre-Hoc recombinase catalyzes site-specific recombination of LSL-GFP DNA substrate which contains two loxP sites. The band pattern in FIG. 60 is consistent with what has been reported[30].

Figure 61:
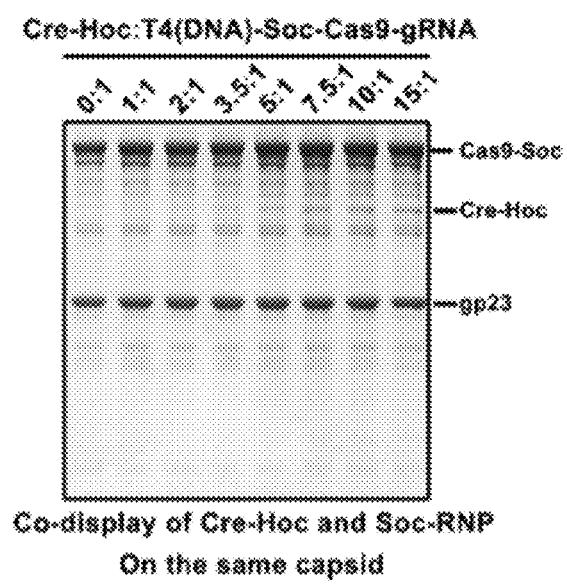
FIG. 61 is a graph showing co-display of Cas9-Soc and Cre-Hoc according to one exemplary embodiment of the present invention.
Figure 62:
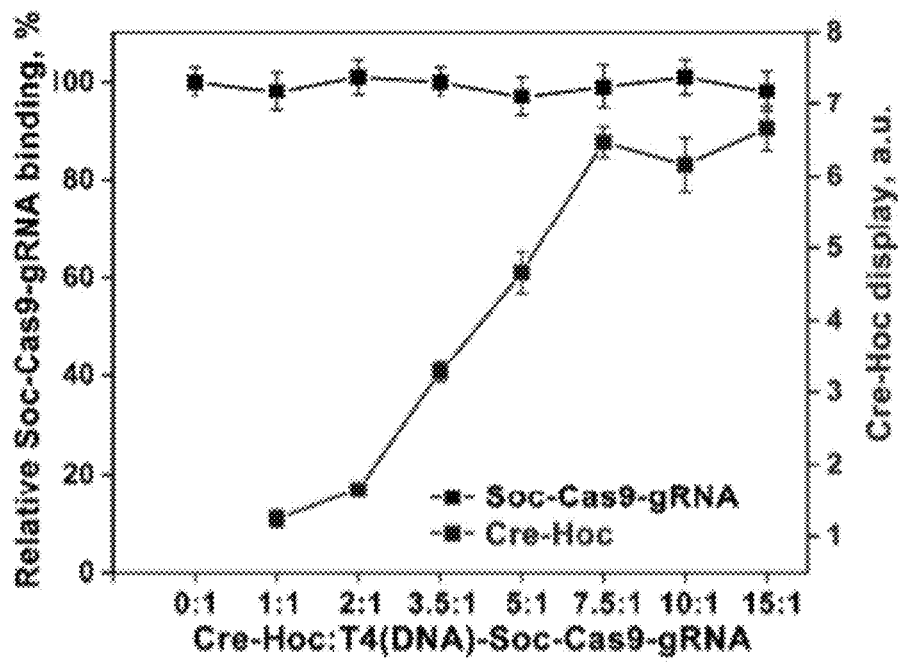
FIG. 62 is a graph showing the impact of Cre-Hoc binding on the binding of Cas9-gRNA RNP on the same capsid according to one exemplary embodiment of the present invention.

In another embodiment, these AVs also carried the Cas9-gRNA RNP complexes displayed on the surface and mCherry reporter plasmid molecules packaged inside, as shown in FIG. 57. FIG. 61 show co-display of Cas9-Soc (5:1, Cas9-Soc molecules to Soc binding sites) and Cre-Hoc at increasing ratios of Cre-Hoc molecules, as determined by SDS-PAGE analysis. FIG. 62 shows the impact of Cre-Hoc binding on the binding of Cas9-gRNA RNP on the same capsid. As shown in FIG. 62, both Cas9-gRNA RNP and Cre-Hoc bound to the same capsid and increasing Cre-Hoc display did not affect Cas9-gRNA RNP binding.

Figure 63:
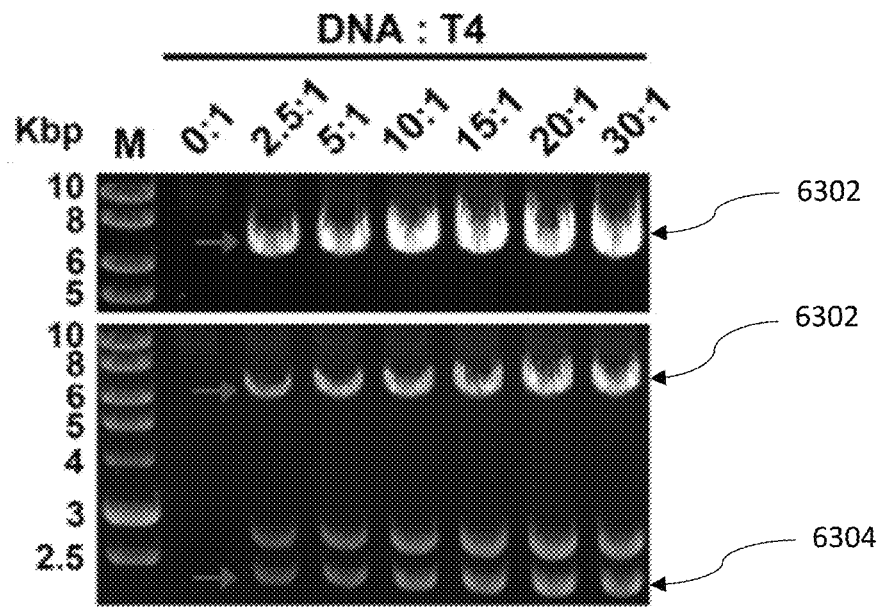
FIG. 63 is a graph showing the quantification of packaged LSL-GFP plasmid DNA for T4-AVs according to one exemplary embodiment of the present invention.

FIG. 63 shows the quantification of packaged LSL-GFP plasmid DNA (6302) and mCherry reporter plasmid (6304) for T4-AVs described in the above two embodiments. The linearized DNAs are incubated with T4 at increasing DNA-to-capsid ratios as indicated at the top of the panels. Maximum packaging capacity reached at a ratio of 15-20:1.

Figure 64:
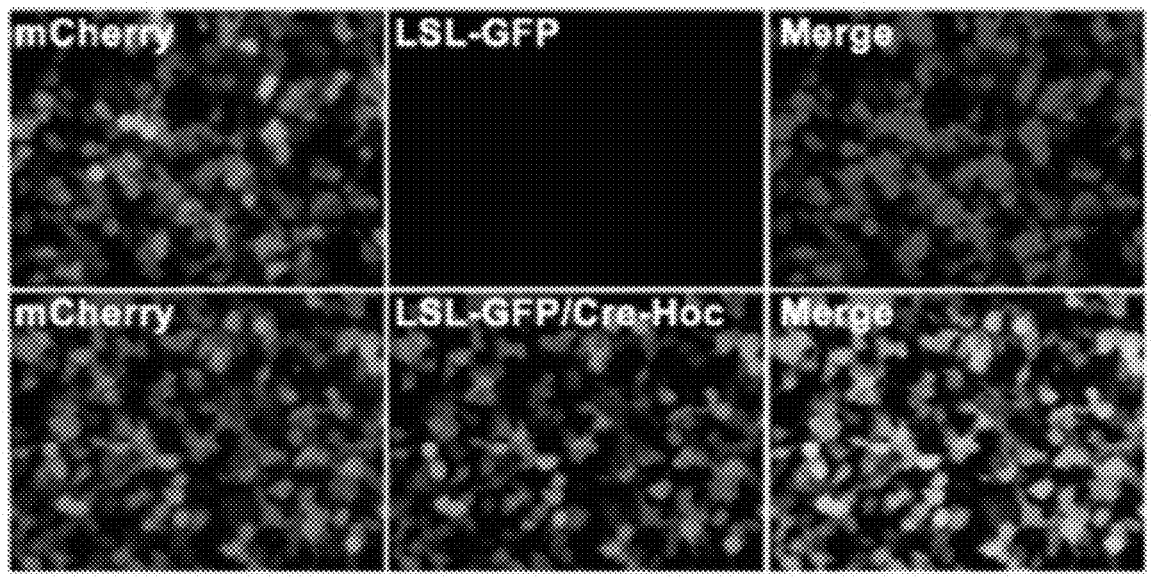
FIG. 64 is a graph showing the co-delivery and co-expression of LSL-GFP and mCherry DNAs according to one exemplary embodiment of the present invention.
Figure 65:
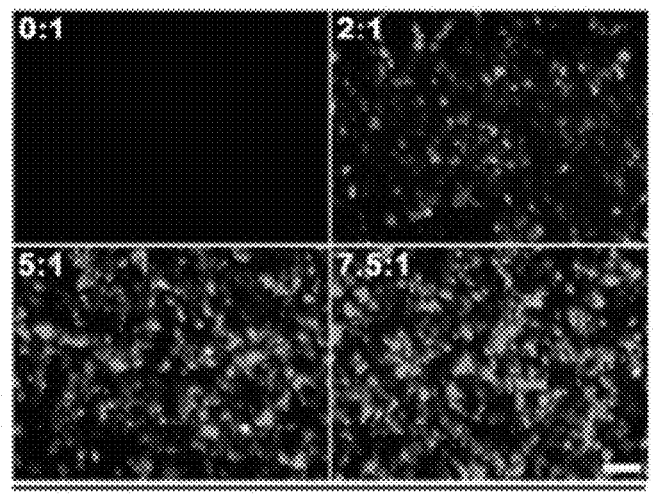
FIG. 65 is a graph showing the representative GFP expression images following transduction of 293 cells with Cre-Hoc-T4(LSL-GFP)-Soc-Cas9-gRNA-AVs at increasing Cre-Hoc display ratio according to one exemplary embodiment of the present invention.

Together, this constitutes a large payload; 50 molecules of Cre, 270 molecules of RNP complex, 6 molecules of GFP donor plasmid, and 5 molecules of mCherry reporter plasmid in the same AV. Remarkably, these AVs performed all the tasks they are programmed with. First, the RNPs carry out genome editing at the AAVS1 site to ~30% editing efficiency. Second, strong green fluorescence is observed in nearly 100% of 293 cells demonstrating efficient site-specific recombination by Cre, whereas control AVs lacking Cre showed no significant fluorescence, as shown in FIG. 64. LSL-GFP and mCherry DNAs are co-delivered and co-expressed in each cell, with the GFP expression occurring following recombination by co-delivered Cre protein, all through the same AV. FIG. 65 shows representative GFP expression images following transduction of 293 cells with Cre-Hoc-T4(LSL-GFP)-Soc-Cas9-gRNA-AVs at increasing Cre-Hoc display ratio. As shown in FIG. 65, the GFP expression increases with increasing Cre-Hoc display ratio. Third, the intensity and distribution of green fluorescence are comparable to that of mCherry fluorescence generated from the direct expression of a reporter gene that requires no recombination, as shown in the lower row in FIG. 64. This means that Cre, after AV entry and disassembly get re-located to the nucleus by virtue of its nuclear localization signal and perform LoxP recombination on the co-delivered and independently re-located GFP donor plasmid in nearly 100% of cells, which then lead to efficient transcription of GFP reporter from the upstream CMV promoter.

Figure 66:
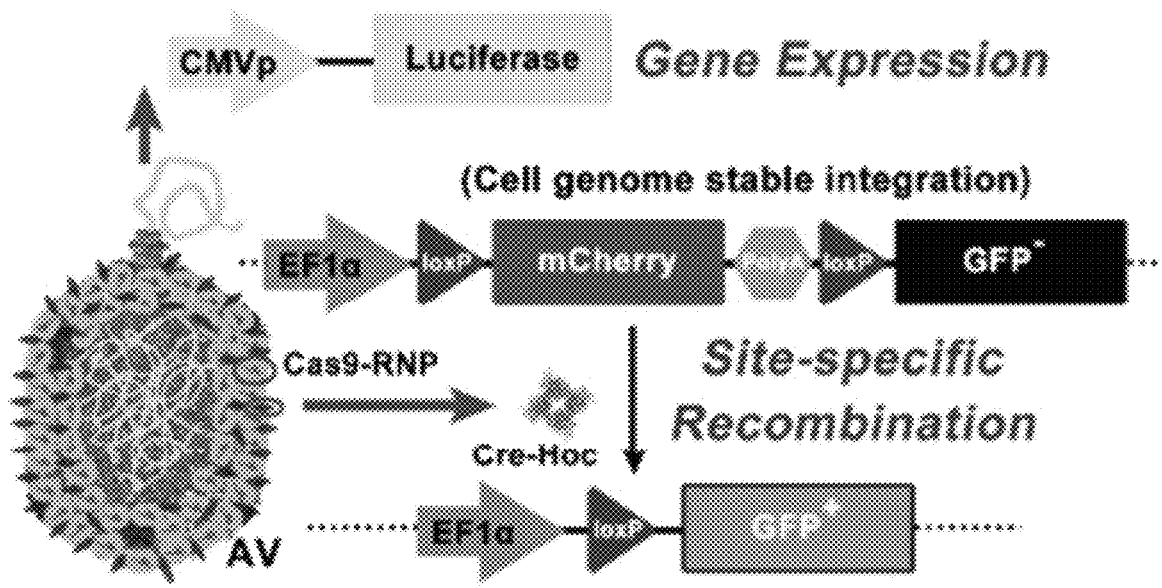
FIG. 66 is a schematic diagram showing the delivery of Cre-Hoc-T4(Luci)-Soc-Cas9-gRNA-AVs into Cre reporter cells according to one exemplary embodiment of the present invention.
Figure 67:
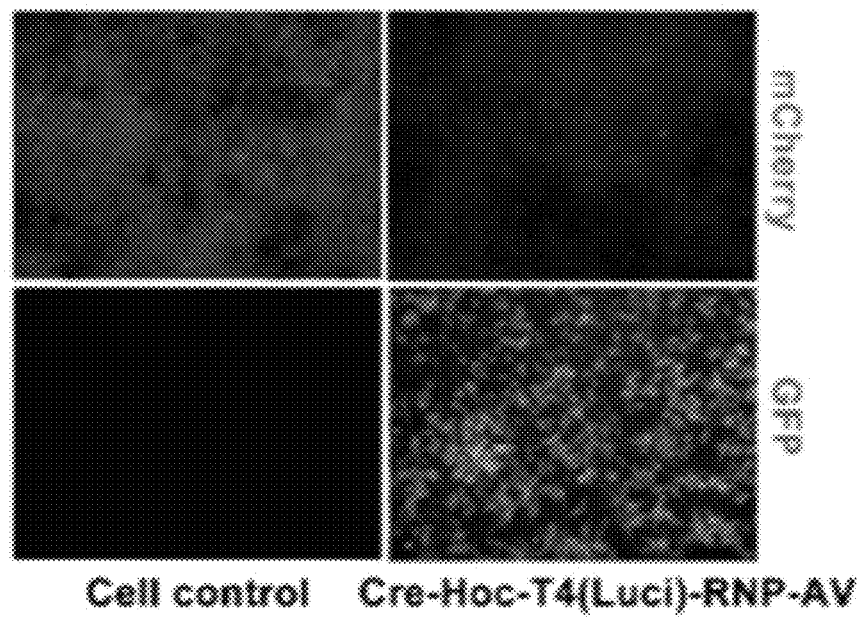
FIG. 67 is a graph showing the AVs mediated efficient site-specific recombination in Cre reporter cells according to one exemplary embodiment of the present invention.
Figure 68:
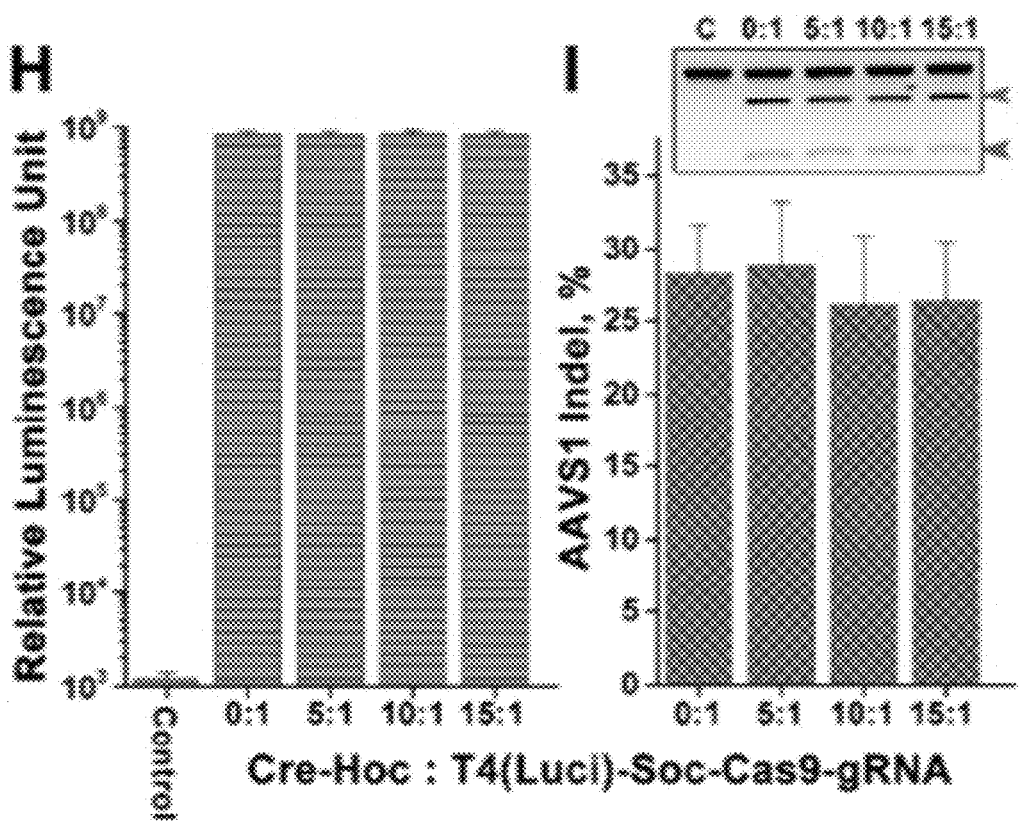
FIG. 68 is a graph showing the luciferase activity and AAVS1 indel frequencies of the cells treated with Cre-Hoc-T4(Luci)-RNP-AVs at increasing Cre-Hoc display ratios according to one exemplary embodiment of the present invention.

The high efficiency of site-specific recombination by T4-AVs is also verified by another approach. A stable 293 cell line is constructed by integrating a LoxP-mCherry-LoxP-polyA-STOP cassette upstream of promoterless GFP reporter gene. Then, AVs programmed with Cre, Cas9-gRNA RNPs, and Luci reporter plasmid are delivered into these cells that result in several genome modifications. The steps of verification are illustrated in FIG. 66, which is a schematic of Cre-Hoc-T4(Luci)-Soc-Cas9-gRNA-AVs delivery into Cre reporter cells. First, efficient Cre-mediated site-specific recombination occur, as evident by the cells showing strong red fluorescence but no green fluorescence at the start due to endogenous mCherry expression, which then turn into intensely green fluorescent, while the red fluorescence fades. This means that the transcriptionally active mCherry gene is spliced out by intramolecular recombination between the flanking LoxP sites by the AV-delivered Cre, in turn activating GFP reporter expression which now come under the control of an upstream promoter, as shown in FIG. 67. Second, the AVs co-delivered the Luci reporter gene which is expressed at high efficiency at all Cre-Hoc to T4(Luci)-Soc-Cas9-gRNA ratios, as shown in the left panel of FIG. 68. Third, these AVs also carried out efficient genome editing at another targeted site on the human genome, as evident from ~30% gene disruption at the AAVS1 locus, as shown in the left panel of FIG. 68.

RNA Delivering Artificial Viruses

In another embodiment, this system is adapted for general RNA delivery including siRNAs, in light of strong interaction observed between Cas9 and gRNA and efficient delivery of the resultant RNP complexes by T4-AVs, as described in the above embodiments. siRNAs are ~20-25 bp double-stranded oligonucleotides that target mRNA(s) having the same sequence for degradation instead of translation. Such siRNA-mediated gene silencing mechanism has been extensively used for treatment of various genetic and infectious diseases[13].

Figure 69:
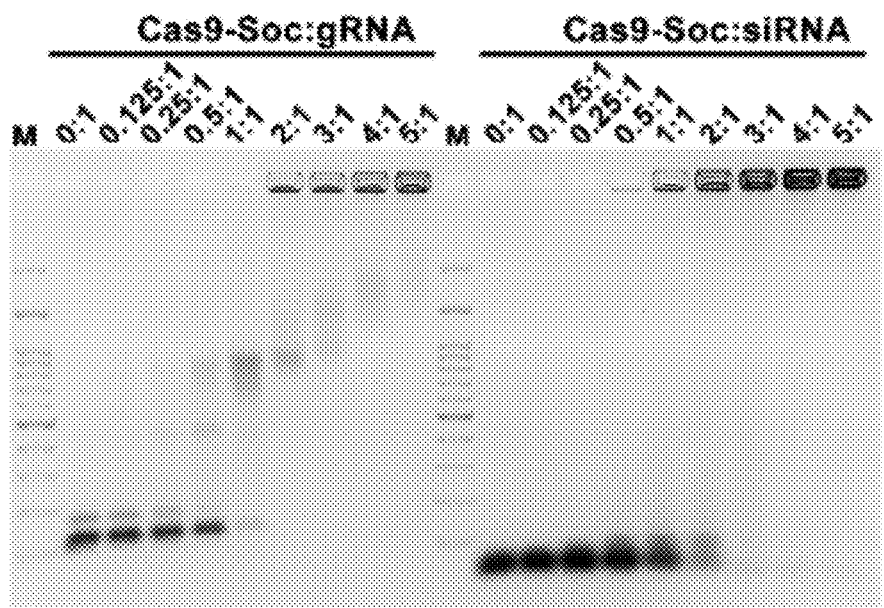
FIG. 69 is a graph showing the stoichiometry of gRNA/siRNA:Cas9-Soc binding according to one exemplary embodiment of the present invention.

Cas9 efficiently binds to siRNA. In vitro gel retardation experiments show that gRNA can replace bound siRNA in the Cas9-siRNA complex. FIG. 69 shows the result of an electrophoretic mobility shift assay, determining the gRNA/siRNA:Cas9-Soc binding stoichiometry. In the electrophoretic mobility shift assay, a constant amount of gRNA or siRNA is mixed with various molar ratios (0:1 to 5:1) of Cas9-Soc molecules for 1 h at room temperature and then analyzed by agarose gel electrophoresis. The gRNA/siRNA-Cas9-Soc complexes remained in the loading well. With the increasing ratios of Cas9-Soc to gRNA/siRNA, the amount of gRNA/siRNA-Cas9-Soc complexes remained in the loading well increases.

Figure 70:
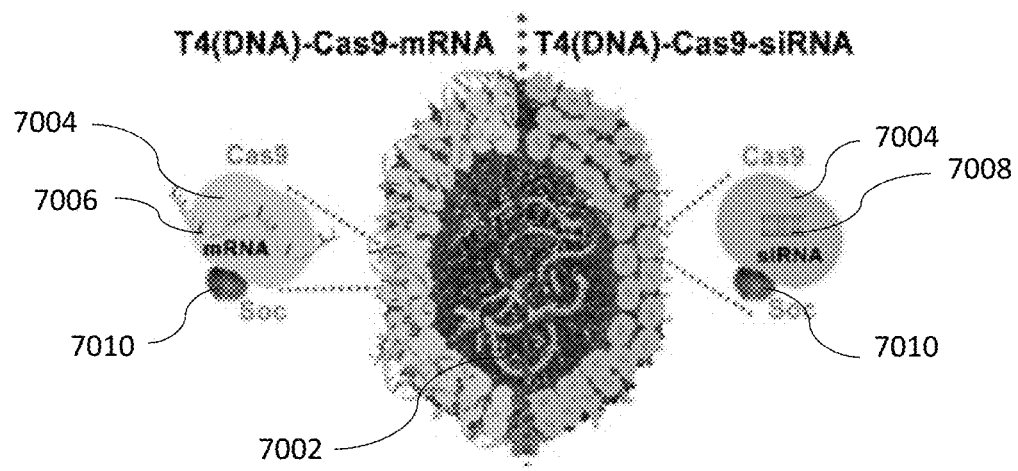
FIG. 70 is a schematic diagram showing the T4-AVs carrying siRNA and mRNA payloads according to one exemplary embodiment of the present invention.
Figure 71:
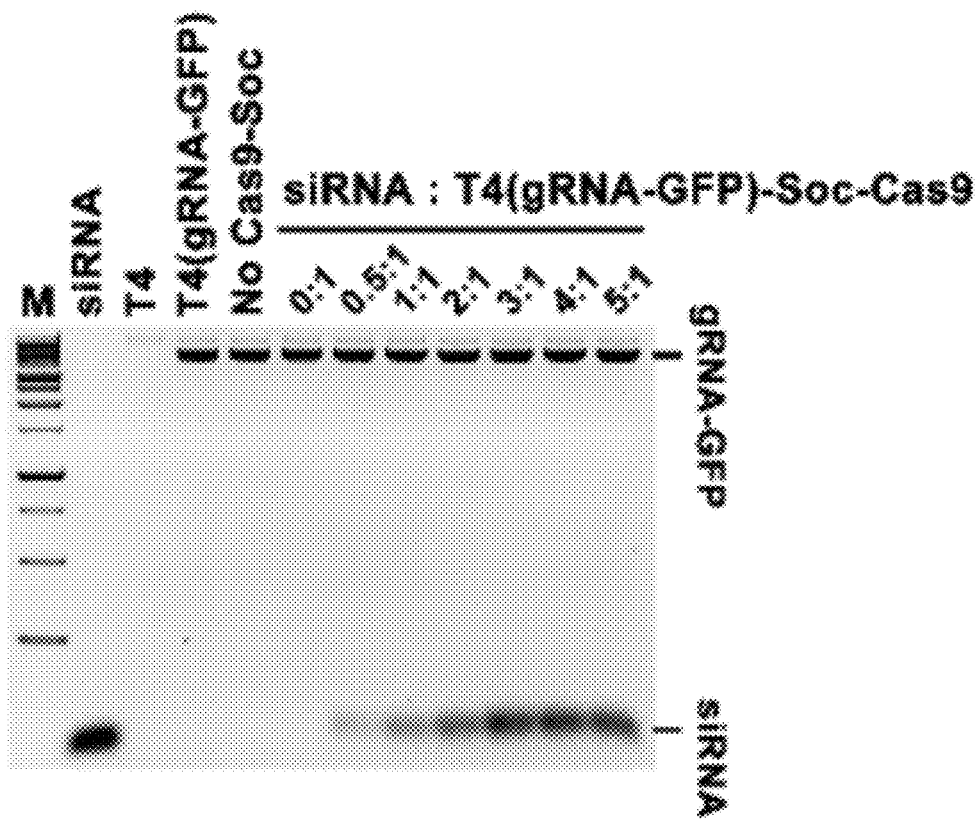
FIG. 71 is a graph showing the binding of siRNA to the T4(gRNA-GFP)-Soc-Cas9 capsids at increasing ratios of siRNA molecules to Soc binding sites according to one exemplary embodiment of the present invention.

In one embodiment, the T4-AVs are decorated with Cas9-siRNA RNP and/or Cas9-mRNA RNP complexes. In a preferred embodiment, the T4-AVs are decorated with ~280 Cas9-siRNA RNP complexes. The configurations of T4-AVs carrying siRNA and mRNA payloads are summarized in the table below. FIG. 70 is a schematic of T4-AVs carrying siRNA and mRNA payloads, with DNA (7002) packaged in T4 and RNP complexes, containing Cas9 (7004), mRNA (7006) or siRNA (7008) and Soc (7010), displayed outside. The binding of siRNA to the T4(gRNA-GFP)-Soc-Cas9 capsids increases with the increasing ratios of siRNA molecules to Soc binding sites, as shown in FIG. 71.

| Payloads of RNA T4-AVs | |
|---|---|
| Packaged inside | Displayed outside |
| gRNA; GFP/Luci | Cas9-siRNA1 |
| gRNA; GFP/Luci | Cas9-siRNA1&2 |
| gRNA; mCherry/Luci | Cas9-mRNA |

Figure 72:
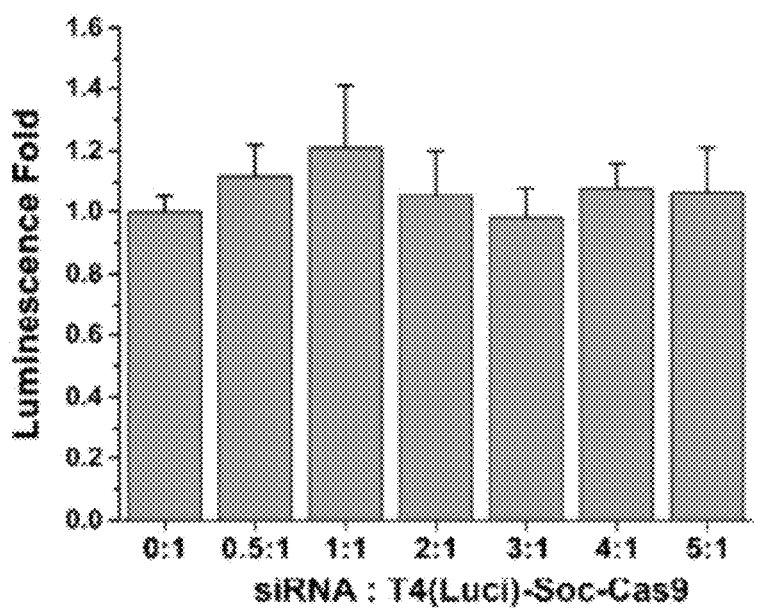
FIG. 72 is a graph showing the effect of siRNA:T4(Luci)-Soc-Cas9 ratios on the AV delivery efficiency according to one exemplary embodiment of the present invention.
Figure 73:
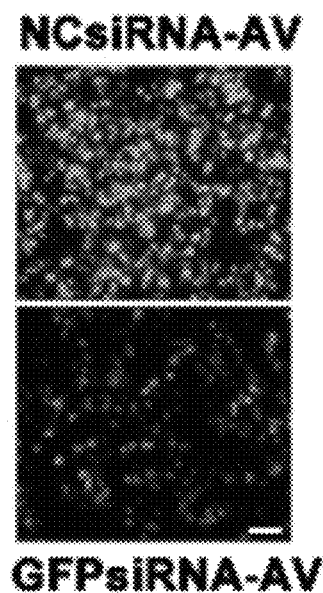
FIG. 73 is a graph showing the silencing of GFP expression in 293 cells treated with GFPsiRNA-AVs according to one exemplary embodiment of the present invention.
Figure 74:
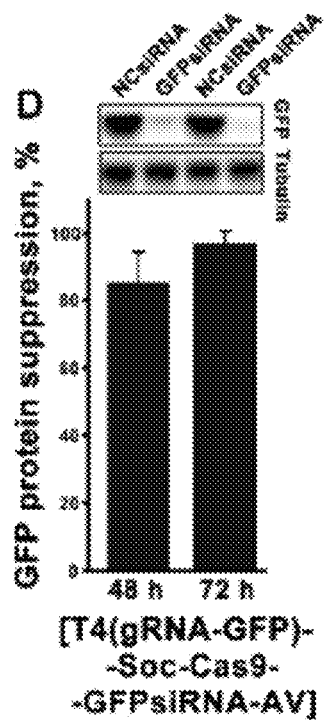
FIG. 74 is a graph showing the quantification of GFP protein levels by GFPsiRNA-AVs at 48 and 72 h post-transduction according to one exemplary embodiment of the present invention.
Figure 75:
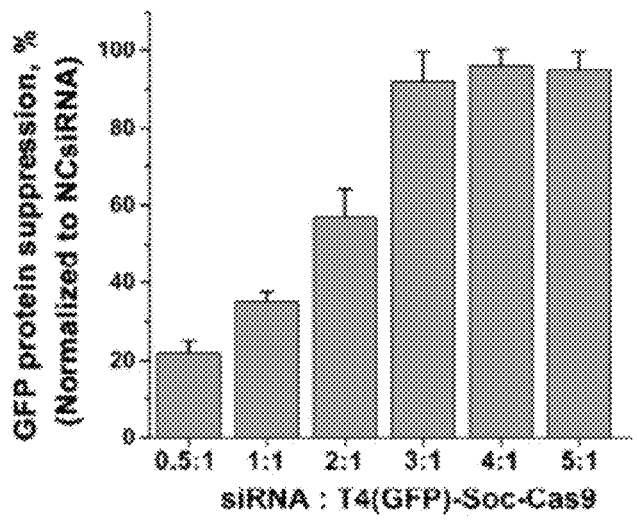
FIG. 75 is a graph showing the effect of the displayed siRNA amount on the efficiency of GFP gene silencing according to one exemplary embodiment of the present invention.

In one embodiment, when exposed to 293 cells, these AVs, which also contain the packaged GFP or Luci reporter plasmids, efficiently delivered siRNA molecules and silenced GFP expression, while the control AVs delivering a nonspecific control siRNA (NCsiRNA) had no effect, as shown in FIG. 73. FIG. 72 shows that the siRNA:T4(Luci)-Soc-Cas9 ratios have no effect on the AV delivery efficiency. Luciferase expression of T4(Luci)-Soc-Cas9-siRNA-AVs delivery is compared to control transduction with T4(Luci)-Soc-Cas9-AVs (lacking siRNA) and presented as the fold change. In FIG. 74, western blotting quantification shows suppression of GFP protein levels by GFPsiRNA-AVs at 48 and 72 h post-transduction. Remarkably, up to ~90% silencing is achieved in 48 hrs and near 100% silencing in 72 hrs by the T4-AVs, as shown in FIG. 74. The GFP suppression percentage is quantified in FIG. 75, which shows the GFP suppression percentage increases with the increase ration of siRNA to T4(GFP)-Soc-Cas9. Also shown in FIG. 75, the GFP suppression percentage reaches close to 100% at the ration of siRNA to T4(GFP)-Soc-Cas9 of 3:1.

Figure 76:
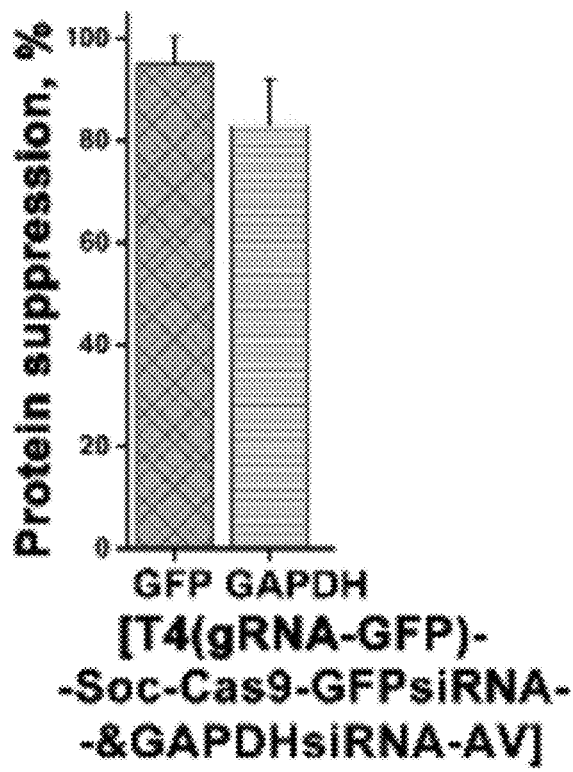
FIG. 76 is a graph showing simultaneous gene silencing at two sites by incorporating two siRNAs into the same AV according to one exemplary embodiment of the present invention.

In one embodiment, two siRNAs silencing different mRNAs could be simultaneously delivered. In a preferred embodiment, one of the two siRNAs into the same AV target to GFP gene and the other to the housekeeping gene GAPDH. AVs carrying GFP-siRNA and GAPDH-siRNA knock down the expression of both these genes by ~95% and 80%, respectively, as shown in FIG. 76.

Figure 77:
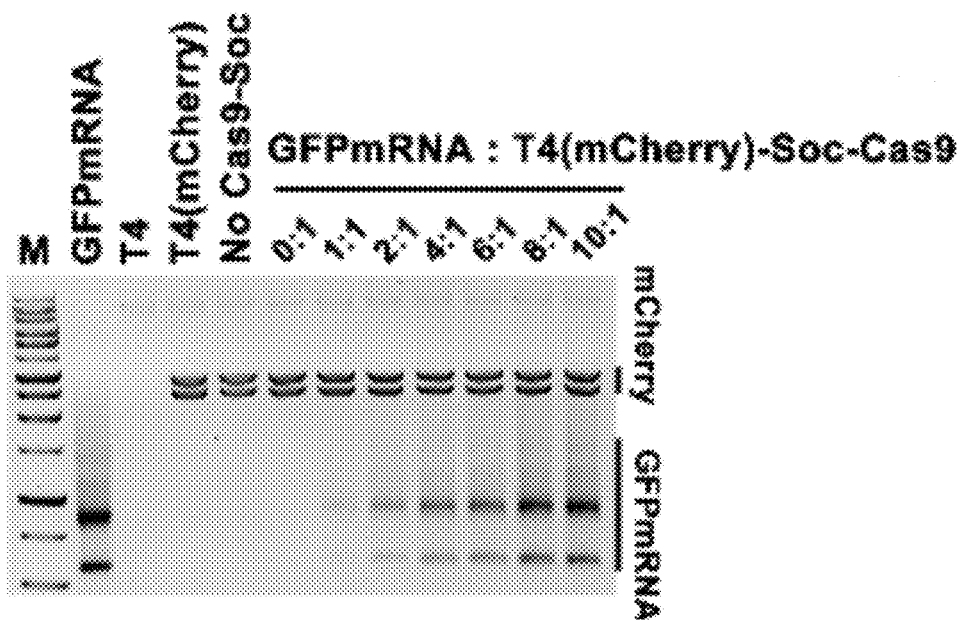
FIG. 77 is a graph showing the loading of GFPmRNA on T4(mCherry)-Soc-Cas9 capsids at increasing ratios of mRNA molecules to Soc binding sites according to one exemplary embodiment of the present invention.
Figure 78:
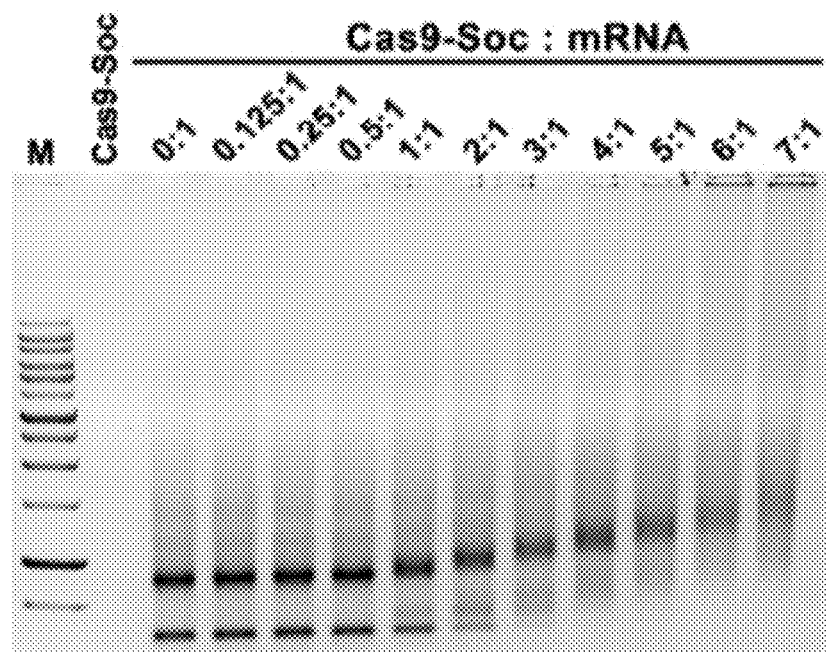
FIG. 78 is a graph showing the binding of mRNA to Cas9-Soc protein at increasing ratios of Cas9-Soc molecules to mRNA according to one exemplary embodiment of the present invention.

Delivery of much longer mRNA molecules would further expand the footprint of RNA-AVs to high-level expression of genes for therapeutic applications[46]. In one embodiment, the siRNA of the above AVs is replaced with mRNA by simply mixing the in vitro transcribed 996-nt GFP mRNA with Cas9-T4 capsids. The Cas9-mRNA complexes are formed efficiently, reaching saturation at ~8:1 ratio of mRNA to Cas9 molecules, as shown in FIG. 77, while no significant mRNA binding is evident with the control capsids lacking Cas9. FIG. 77 shows the loading of GFPmRNA on T4(mCherry)-Soc-Cas9 capsids at increasing ratios of mRNA molecules to Soc binding sites, which remains the same after the ratios of mRNA molecules to Soc binding sites reaches 8:1. This result is confirmed by an electrophoretic mobility shift assay showing the binding of mRNA to Cas9-Soc protein at increasing ratios of Cas9-Soc molecules to mRNA (0:1 to 7:1), as shown in FIG. 78. Each AV carried a payload of ~55 molecules of mRNA. The lower copy number of mRNA when compared to siRNA is probably because the much longer mRNA titrated several molecules of Cas9.

Figure 79:
FIG. 79 is a graph showing co-localization of gene expression of AV-packaged mCherry plasmid DNA and AV-displayed GFP mRNA in the same cell. according to one exemplary embodiment of the present invention.
Figure 80:
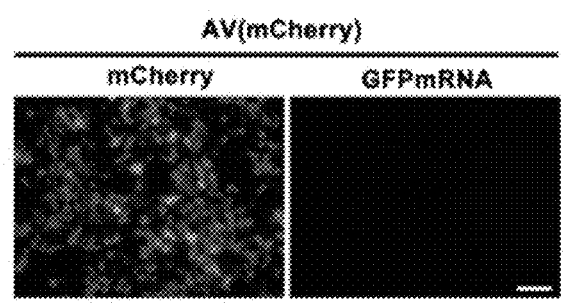
FIG. 80 is a graph showing the delivery and expression of AV(mCherry) as a control according to one exemplary embodiment of the present invention.
Figure 81:
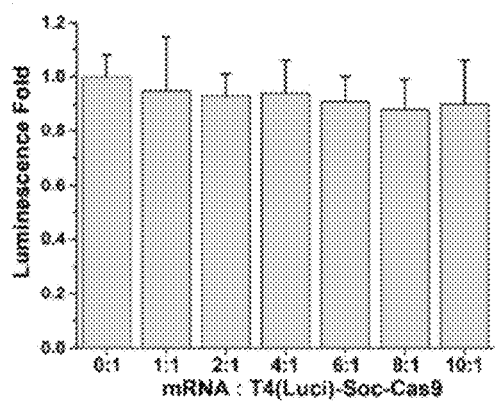
FIG. 81 is a graph showing the impact of the amount of displayed mRNA on the co-delivery efficiency of T4(Luci)-Soc-Cas9-mRNA-AVs according to one exemplary embodiment of the present invention.

In one embodiment, the GFPmRNA-AVs described in the above embodiment upon transduction into 293 cells express strong green fluorescence in the cells, and the fluorescence is evenly distributed throughout the cell and merges with the red fluorescence generated by co-delivery of mCherry reporter gene packaged in the same AV, as shown in FIG. 79. On the other hand, control (mCherry)AVs lacking the Cas9-mRNA complex showed only red fluorescence, as shown in FIG. 80. Additionally, expression of packaged Luci reporter suggested that mRNA display does not affect the AVs' efficient transduction, as shown in FIG. 81. Luciferase expression is compared with the control AVs lacking mRNA display and presented as the fold change.

Figure 82:
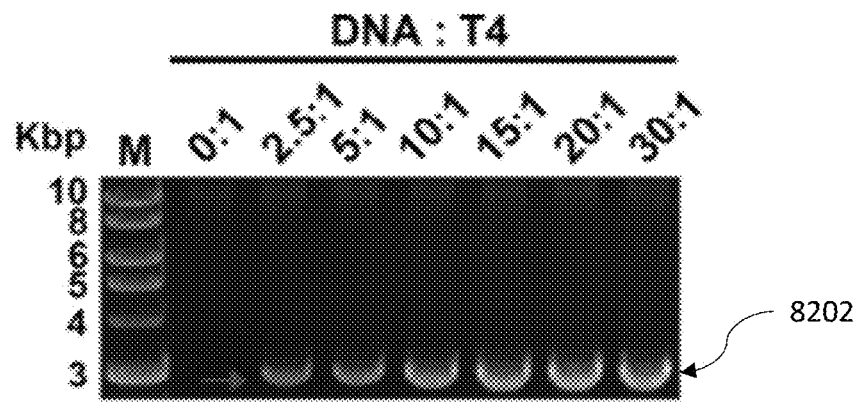
FIG. 82 is a graph showing the quantification of packaged gRNA expression plasmid for various T4-AVs according to one exemplary embodiment of the present invention.

In another embodiment, another gRNA expression plasmid is packaged into the above AVs, to further enhance the utility of the RNA-AVs. FIG. 82 shows the quantification of packaged gRNA expression plasmid (AAVS1 gRNA) (8202). With this configuration, upon delivery, the displayed Cas9 can first deliver siRNA or mRNA into the cytosol and then, by virtue of the fused NLS sequence, it can re-locate to the nucleus and form a genome editing complex with the gRNA expressed from the co-delivered plasmid. Cas9 then can perform a second function, genome editing at the target site.

Figure 83:
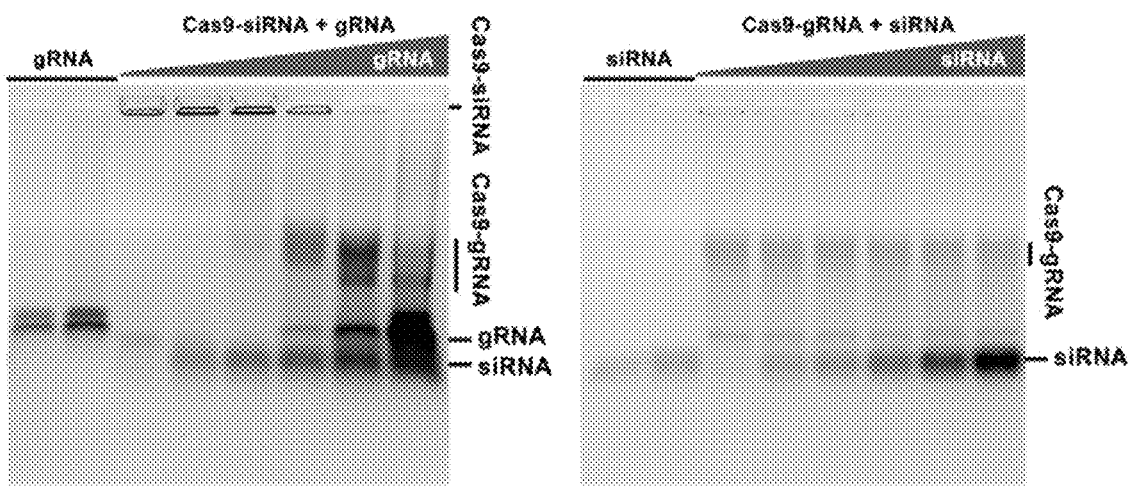
FIG. 83 is a graph showing the replacement of bound siRNA in the Cas9-siRNA complex by gRNA according to one exemplary embodiment of the present invention.
Figure 84:
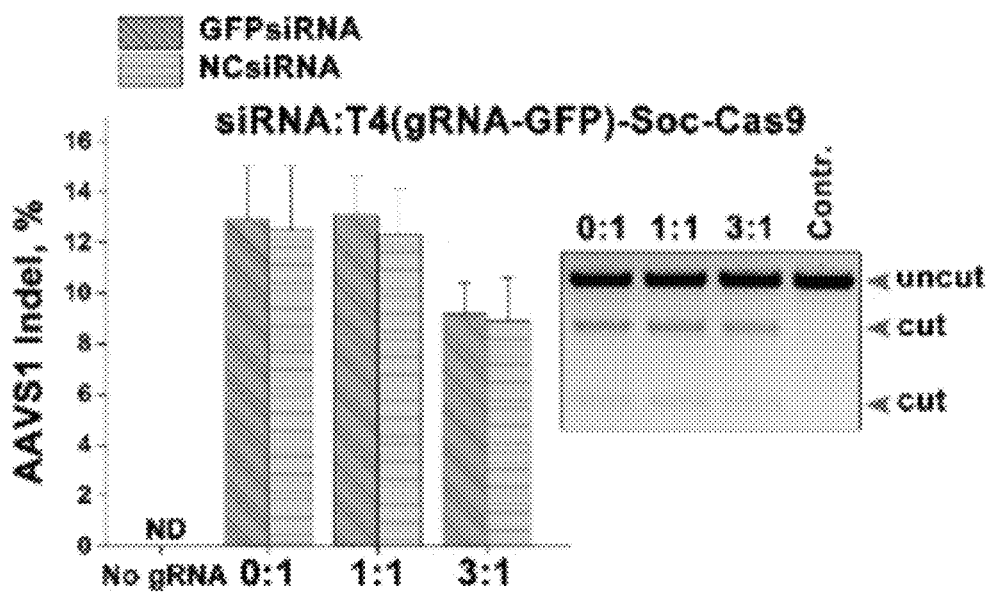
FIG. 84 is a graph showing the quantification of AAVS1 indel frequencies of cells treated with T4(AAVS1gRNA-GFP)-Soc-Cas9-siRNA-AVs at increasing ratios of siRNA molecules to soc binding sites according to one exemplary embodiment of the present invention.
Figure 85:
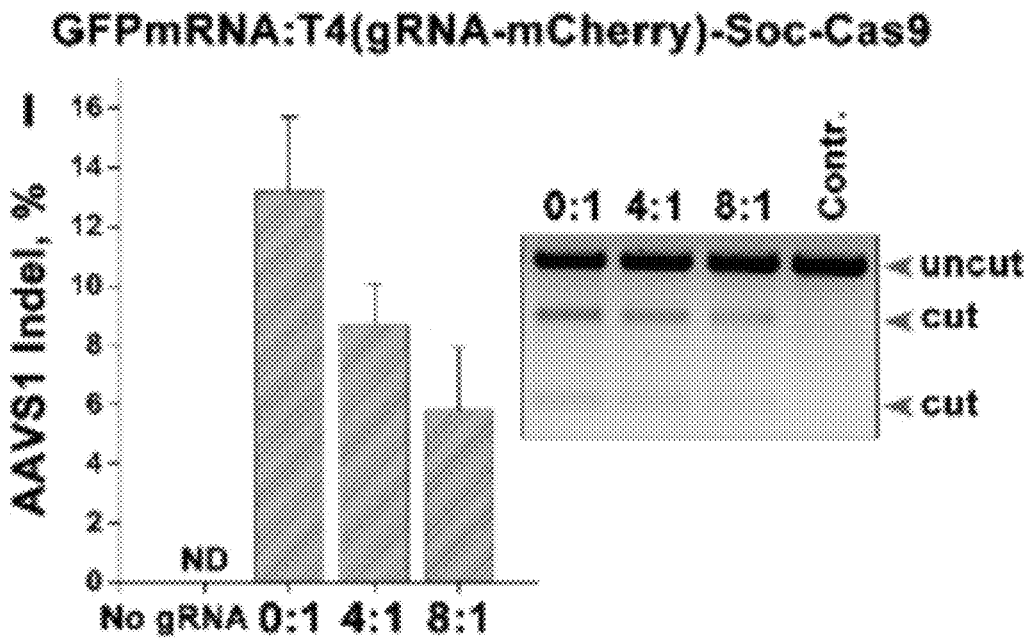
FIG. 85 is a graph showing the genome editing at AAVS1 locus by T4(AAVS1gRNA-mCherry)-Soc-Cas9-GFPmRNA-AVs at increasing ratios of mRNA molecules to capsid-displayed Cas9 according to one exemplary embodiment of the present invention.

Control in vitro experiments show that gRNA can replace bound siRNA in the Cas9-siRNA complex as shown in the left panel of FIG. 83, whereas the reverse, siRNA replacement of gRNA in the Cas9-gRNA complex, does not occur, as shown in the right panel of FIG. 83. In one embodiment, the AVs are programmed with displayed Cas9-siRNA or Cas9-mRNA complexes and packaged inside the gRNA and mCherry reporter plasmids, by taking advantage of these differential affinities of Cas9 to siRNA and gRNA. In one embodiment, upon transduction into 293 cells, these AVs perform GFP gene silencing or GFP mRNA expression, genome editing at AAVS1, and mCherry expression in the same cell, as shown in FIGS. 84 and 85. FIG. 84 shows Quantification of AAVS1 indel frequencies of cells treated with T4(AAVS1gRNA-GFP)-Soc-Cas9-siRNA-AVs at increasing ratios of siRNA molecules to soc binding sites. The box on the right shows AAVS1 gene disruption using the T7E1 assay. FIG. 85 shows the quantification of genome editing at AAVS1 locus by T4(AAVS1gRNA-mCherry)-Soc-Cas9-GFPmRNA-AVs at increasing ratios of mRNA molecules to capsid-displayed Cas9.

Maximizing the Programmability of T4 Artificial Viruses

A CRISPR strategy[53] that allows filling of the interior capsid space with proteins in addition to DNAs has been developed, to further amplify the programmability of T4-AVs. This would not only increase the cargo capacity but also impart a novel property to T4-AVs, ability to assemble DNA-protein complexes in situ within the nano-capsid compartment that could, after delivery, guide the transport of DNA cargo to the nucleus. Such a guided transport system (GTS) could be adapted in future for guiding the cargos to appropriate intracellular destinations.

During phage T4 morphogenesis[67] the major capsid protein gp23 assembles around a scaffolding core formed by a cluster of proteins including three nonessential histone-like "internal proteins"; IPI, IPII, and IPIII. Following assembly, most of the scaffold proteins are degraded to small peptides, which then leave the capsid creating space for genome encapsidation. The IPs, however, are cleaved only once, next to a ~10 amino acid N-terminal capsid targeting sequence (CTS). While the CTS leaves the capsid, the highly basic IPs, ~1,000 molecules in total, remain inside the capsid and protect the genome after the DNA-protein complex is injected into the host E. coli during phage infection. Previous studies showed that when the C-terminal portion of the IPs is replaced with foreign proteins, the N-terminal CTS targets the foreign proteins to the core, which after CTS removal remain in the capsid space[32].

Figure 86:
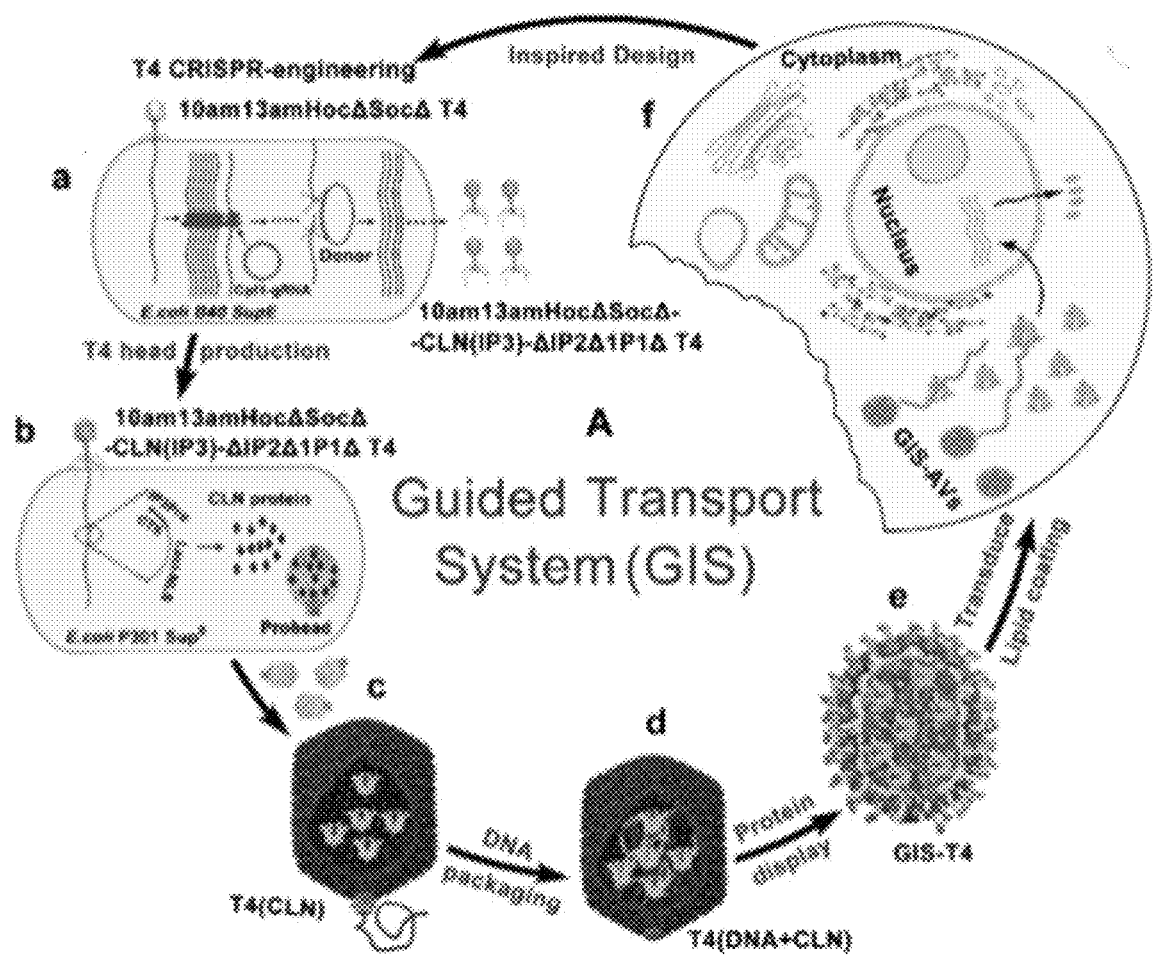
FIG. 86 is a schematic diagram showing the programmable guided transport system (GIS) using CRISPR-engineered T4-AVsaccording to one exemplary embodiment of the present invention.
Figure 87:
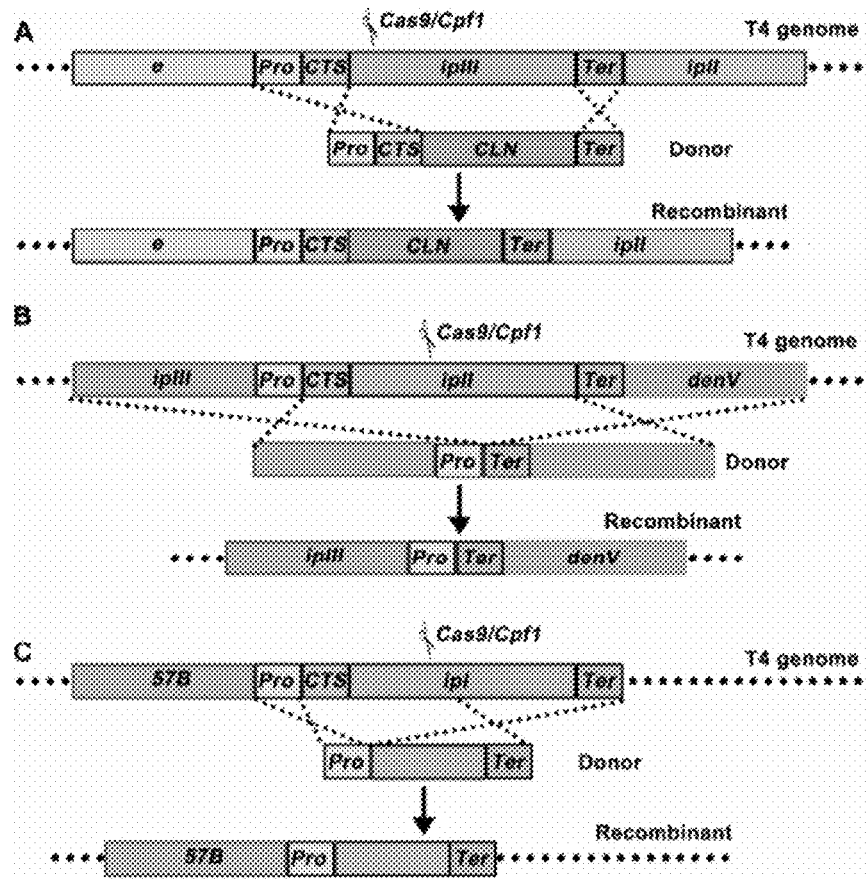
FIG. 87 is a schematic diagram showing the CRISPR-mediated CLN gene insertion according to one exemplary embodiment of the present invention.
Figure 88:
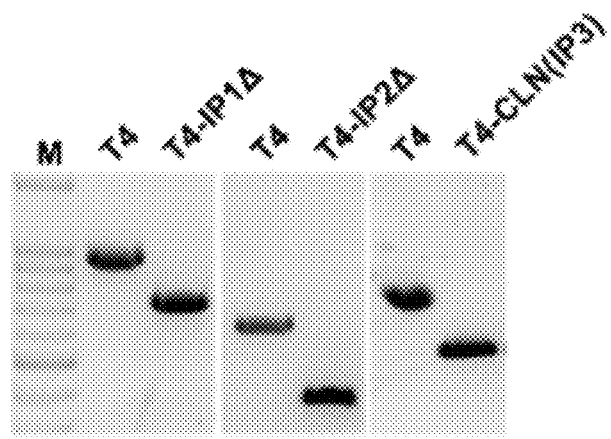
FIG. 88 is a graph showing the CRISPR-mediated T4 genome editing according to one exemplary embodiment of the present invention.
Figure 89:
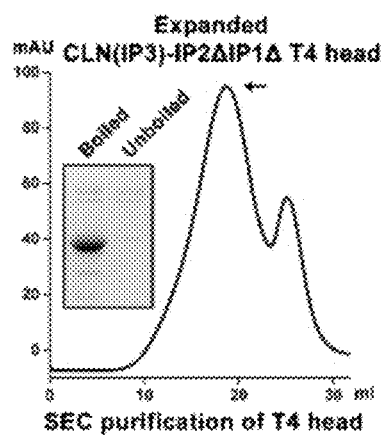
FIG. 89 is a graph showing the size-exclusion chromatography profile according to one exemplary embodiment of the present invention.
Figure 90:
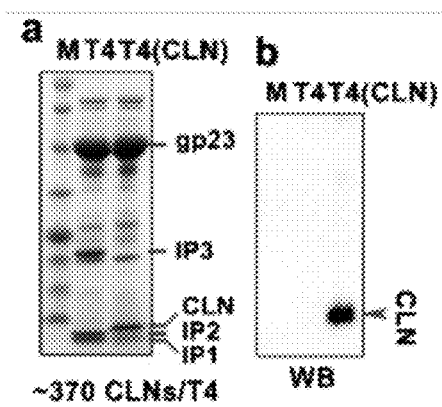
FIG. 90 is a graph showing the expression of head-packaged CLN protein according to one exemplary embodiment of the present invention.
Figure 91:
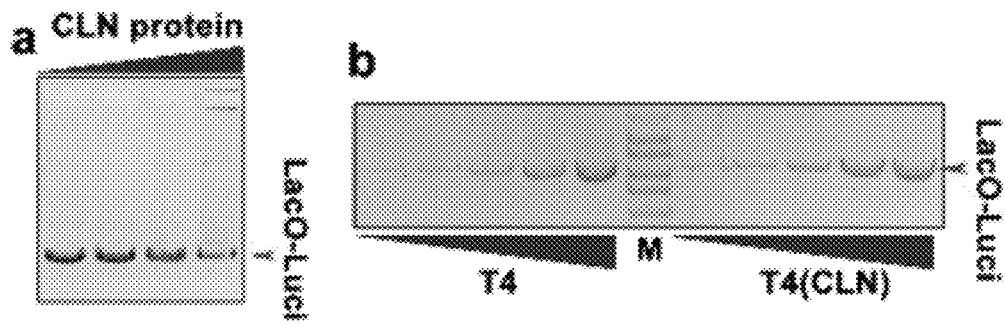
FIG. 91 is a graph showing functional characterizations of CLN protein and T4(CLN) heads according to one exemplary embodiment of the present invention.

In one embodiment, a CRISPR strategy is developed, by which LacI repressor protein molecules are packaged inside the capsid, which can then form complexes with the packaged DNA containing an engineered lac operator sequence (LacO) in trans. An "acceptor" phage is first generated by deleting ipI and ipII genes and this phage is used to infect E. coli containing two plasmids; a spacer plasmid that expresses Cas9 or Cpf1 and CRISPR RNA corresponding to a protospacer sequence in the deleted region of the acceptor phage, and a second donor plasmid containing the LacI repressor gene fused to CTS sequence at the N-terminus and NLS sequence at the C-terminus (CTS-LacI-NLS or CLN) (SEQ ID NO: 20) flanked by ~200 bp homologous arms (FIG. S7A). FIG. 86 is a schematic depicting the programmable guided transport system (GIS) using CRISPR-engineered T4-AVs: a. engineering of CTS-LacI-NLS (CLN) mutant phage by CRISPR genome editing. b. preparation of CLN-packaged T4 heads in E. coli. c. CLN-packaged T4 head. d. CLN-DNA complexes formed in the CLN head following in vitro DNA packaging. e. GIS-T4 with Soc- and/or Hoc-displayed proteins. f. following delivery, the CLN-DNA complexes are guided to the nucleus by the NLS signal. Cleavage within the protospacer sequence of the acceptor phage genome by Cas9/Cpf1 editing complex followed by recombination between the cleaved ends and the homologous arms of donor plasmid transfer the CLN gene into phage genome by replacing the ipIII gene of the acceptor phage, as shown in FIG. 87. Panel A of FIG. 87 is a schematic of CRISPR-mediated CLN gene insertion (ipIII replacement); panel B of of FIG. 87 shows ipII gene deletion; and panel C of of FIG. 87 shows ipI gene (partial) deletion. The rescued recombinant phage thus is devoid of all three IPs but contained the CLN gene in their place. Empty capsids prepared from this CLN mutant phage (10 am.13 am.hoc⁻.soc⁻.CLN) contained ~370 molecules of CLN protein inside the shell and show comparable in vitro DNA packaging efficiencies as the wild-type capsids. Successive rounds of CRISPR-mediated T4 genome editing to create the mutant phages is confirmed by PCR, as shown in FIG. 88. Size-exclusion chromatography profile of T4(CLN) heads is shown in FIG. 89. The arrow indicates the peak fraction of the packaging-competent T4(CLN) heads. The boiled and un-boiled T4 samples on SDS-PAGE demonstrate that the CLN-packaged T4 heads are expanded and behave similarly as the WT (wildtype) T4 heads. The head-packaged CLN protein is confirmed by SDS-PAGE (panel a of FIG. 90) and Western blotting (panel b of FIG. 90) and quantify its copy number. (E) Results of functional characterizations of CLN protein and T4(CLN) heads is shown in FIG. 91. Panel a of FIG. 91 shows the binding of CLN protein to LacO-containing plasmid DNA used for in vitro DNA packaging; in vitro DNA packaging in panel b of FIG. 91 shows that the mutant CLN heads exhibit comparable activity as the WT heads.

Figure 92:
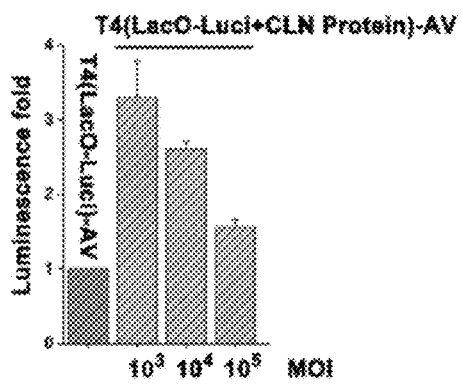
FIG. 92 is a graph showing enhanced laco-luciferase DNA delivery by T4(CLN)-GIS-AVs at different ratios of AVs to cells according to one exemplary embodiment of the present invention.
Figure 93:
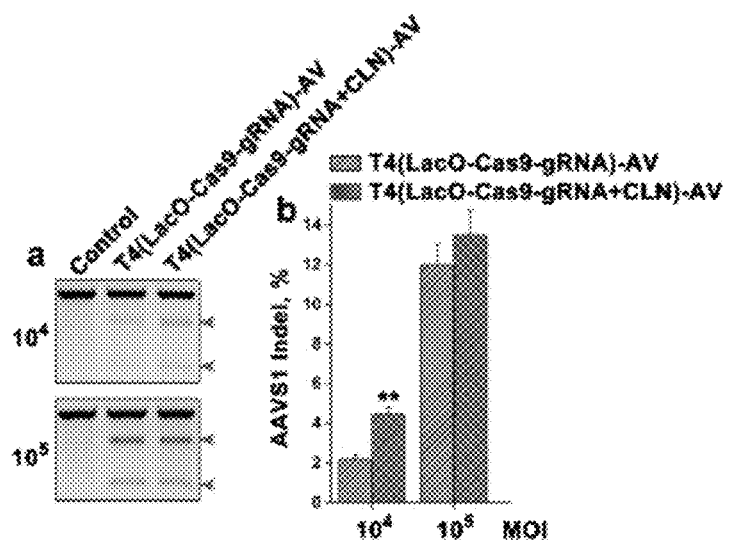
FIG. 93 is a graph showing enhanced genome editing by T4(CLN)-GIS-AVs according to one exemplary embodiment of the present invention.

In one embodiment, the LacO sequence is inserted into the Luci or Cas9-gRNA plasmid and packaged into the CLN capsids. The packaged LacI repressor and LacO-DNA then form DNA-protein complexes as seen in in-vitro gel retardation experiments, as shown in FIG. 91. These AVs upon transduction into human cells showed enhanced expression of luciferase up to ~3.5 fold, as shown in FIG. 92 and Cas9-mediated genome editing by ~2 fold at the MOI of $10^4$, as shown in FIG. 93, presumably through enhanced transport of DNA-LacI complex to the nucleus due to the presence of NLS signal in LacI repressor. Panel a of FIG. 93 shows T7E1 assay result, while panel b of FIG. 93 shows frequency of AAVS1 indels, suggesting that T4(CLN)-GIS-AVs enhance genome editing. The luciferase or gene disruption enhancement is most significant, when the ratio of T4 particles to 293 cells is low, ~$10^3$:1 or ~$10^4$:1, but not at a high ~$10^5$:1 ratio. This is probably because the delivery of more copies of DNA at a high ratio compensated for the enhanced CLN-mediated transport at low copy numbers.

In one embodiment, genes for Cre recombinase are inserted into phage genome using the same strategy. In another embodiment, reporter genes for GFP and β-galactosidase packaging, which could be generally useful for viral genome engineering, are inserted. All these proteins are successfully packaged into T4 capsids, although the copy number varied.

Figure 94:
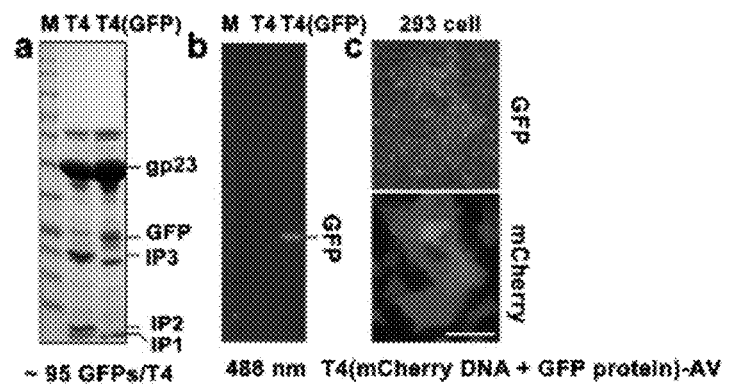
FIG. 94 is a graph showing biochemical characterization of GFP-packaged AVs according to one exemplary embodiment of the present invention.
Figure 95:
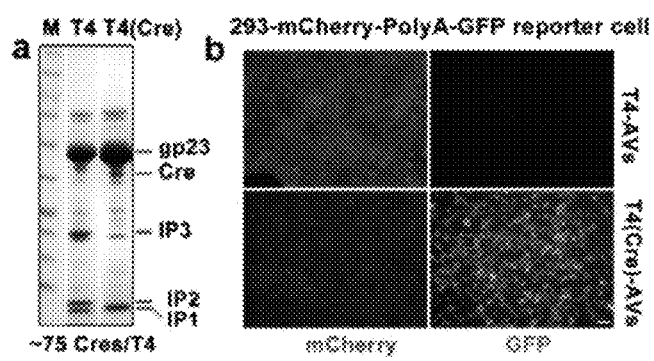
FIG. 95 is a graph showing biochemical characterization of Cre-packaged AVs according to one exemplary embodiment of the present invention.
Figure 96:
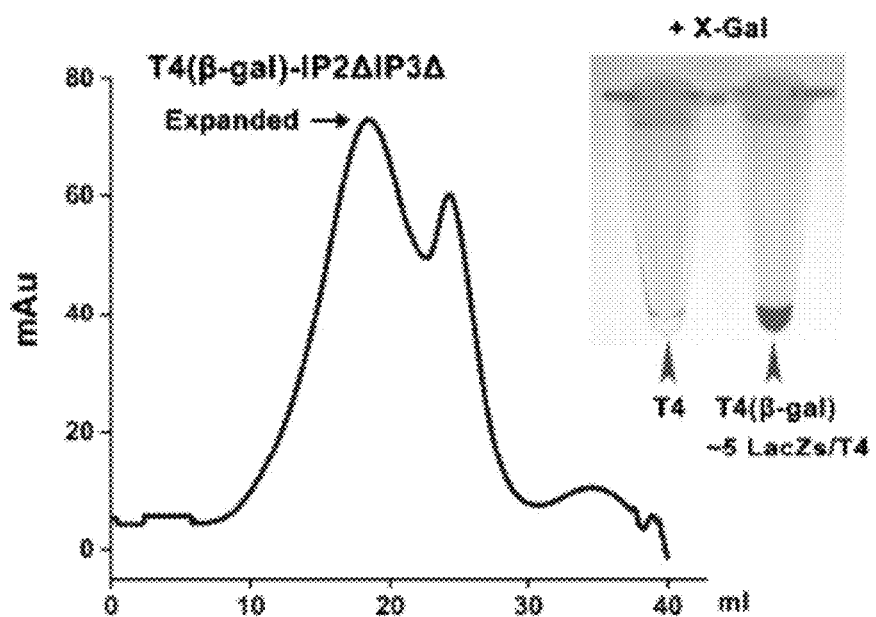
FIG. 96 is a graph showing the formation of functional β-galactosidase tetramers according to one exemplary embodiment of the present invention.
Figure 97:
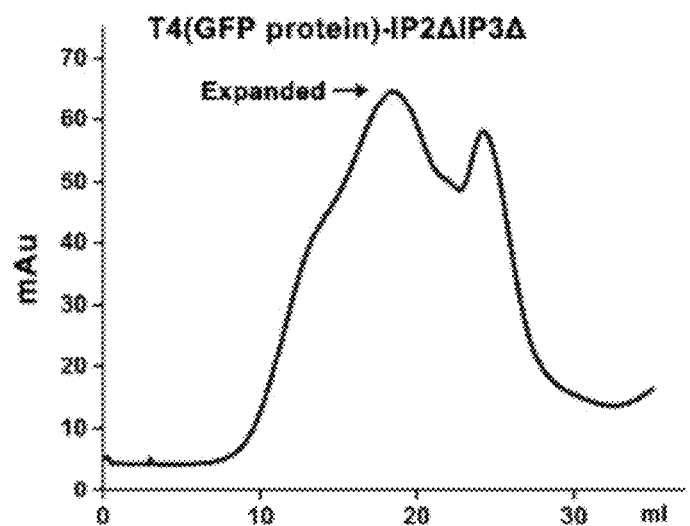
FIG. 97 is a graph showing size-exclusion chromatography profile of T4(GFP) capsid according to one exemplary embodiment of the present invention.
Figure 98:
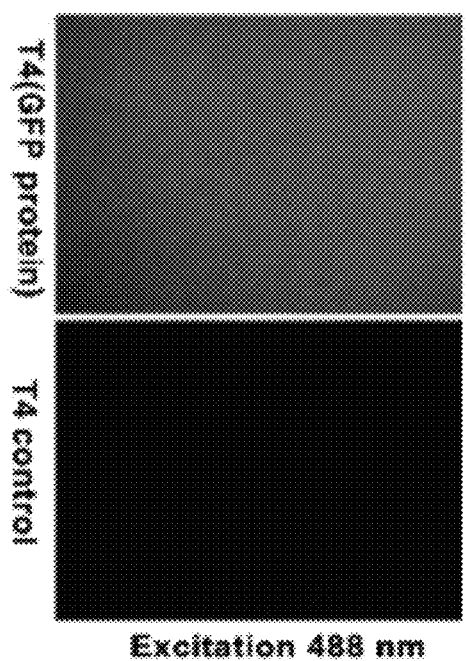
FIG. 98 is a graph showing fluorescence images of "Green fluorescence phage" according to one exemplary embodiment of the present invention.

Variations in size and structure of protein might affect their incorporation into the scaffolding core. FIG. 94 shows the biochemical characterization of GFP-packaged AVs. GFP protein packaging is confirmed by SDS-PAGE (panel a of FIGS. 94) and 488 nm excitation (panel b of FIG. 94). FIG. 95 shows the biochemical characterization of Cre-packaged AVs. Cre-heads is confirmed by SDS-PAGE (panel a of FIG. 95). However, all the packaged proteins retain their biological function; for instance, the packaged β-galactosidase oligomerize into functional tetramers and produce "blue phage" by exhibiting the glucoside hydrolase activity, as shown in FIG. 96. The left panel of FIG. 96 shows a size-exclusion chromatography profile of T4(β-gal) head. The arrow points to the peak fractions of eluted expanded T4(β-gal) capsids. In the right panel, the observation of "Blue phage" shows successful packaging of functional tetrameric β-galactosidase enzyme molecules and appearance of the blue color of the cleaved X-Gal substrate. Similarly, AVs packaged with GFP protein and mCherry plasmid DNA exhibit both green and red fluorescence, the former from delivered protein ("green fluorescence phage") and the latter from delivered DNA, as shown in panel c of FIG. 94. The successful delivery of protein by green fluorescence phage is also confirmed by size-exclusion chromatography profile of T4(GFP) capsid, as shown in FIG. 97, and fluorescence images (FIG. 98) of T4(GFP) and control T4 capsids at 488 nm excitation showing the successful packaging of functional GFP in T4(GFP) capsids. The arrow in FIG. 97 points to the peak fractions of eluted expanded T4(GFP) capsids. Finally, AVs containing packaged Cre recombinase carry out efficient recombination between the LoxP sites of LoxP-mCherry-LoxP-polyA-STOP-GFP cassette to near 100% efficiency resulting in splicing out of the mCherry gene, which in turn allow expression of the GFP gene from an upstream promoter of the spliced product, as shown in panel b of FIG. 95. Therefore, the GTS strategy could be generally applied to DNA binding proteins that could carry out other genome modifications.

Ability to assemble artificial viruses that can be directed to perform defined molecular operations in human cells remained as the holy grail of medicine[20,29,48]. The present disclosure describes the proof of such a concept. A sequential assembly-line approach to build artificial viruses in the test tube is described, using the purified and well-characterized structural components of bacteriophage T4, each engineered to perform a specific task(s) in a human cell. These include: binding and entry into cells, intracellular trafficking, nuclear localization, and genome remodeling[2, 37]. In addition to creating enormous engineering space, this assembly-line approach allows mixing and matching of the components in desired combinations to generate varieties of artificial viruses endowed with specific therapeutic capabilities. Such a custom-buildable, "plug-and-play" artificial virus platform does not exist today, and several features distinguish it from other viral or synthetic delivery platforms currently available.

One of the features of the T4-AV platform is its ability to incorporate many types of therapeutic biomolecules including proteins, DNAs, RNAs, and their complexes in different compartments of the nanoparticle structure. These molecules, upon delivery into a human cell, faithfully execute their function(s) either independently or through interactions with each other. This has been demonstrated across a wide spectrum of molecules; proteins ranging from 27 kDa GFP to 516 kDa tetrameric β-galactosidase enzyme, nucleic acids ranging from large double-stranded plasmid DNAs to small single-stranded gRNAs, and preformed complexes including protein-protein, RNA-protein, and DNA-protein complexes in the present disclosure. Furthermore, analogous to natural viruses, functional circuits formed between delivered molecules upon AV "infection" that can also be tunable by adjusting the copy numbers of the cargo molecules, providing numerous options to create AVs with therapeutic capability.

The T4-AVs consistently generated signal to near 100% efficiency in the model cell line HEK293, as measured either by the expression of a reporter gene (e.g., Luci, GFP, mCherry) or by the activity of a delivered protein (e.g., GFP, β-Gal, Cre). A critical component of the AVs that contributed to high efficiency is the lipid coat, which is created by taking advantage of the highly anionic character of the T4 capsid. Off-the-shelf cationic lipids spontaneously bound to T4 capsid generating a lipophilic and cationic surface that is complementary to the anionic surface of human cells19, 23, 58, 66. Without this coat, the transduction efficiency is poor, as proven by the above embodiments. Even the AVs that are cationic but lacking the lipid coat showed a 100-fold lower signal. Furthermore, the lipid coat does not impair the display of Soc- and Hoc-fused protein molecules. On the other hand, these molecules, particularly the positively charged ones, further accentuate the T4-AV transduction efficiency.

The T4 artificial viruses described in the present disclosure breaks through four major barriers that currently exist for the delivery of biomolecules into human cells. First, the T4-AVs, unlike other delivery platforms, can efficiently deliver multiple copies of multiple and relatively large DNA molecules into cells in a single transduction event. This has been amply demonstrated using a series of plasmids containing reporter genes, antibody genes, and genome editing genes. This is possible not only because of the large cargo capacity of T4 but also because of the promiscuous nature of T4's packaging machinery that exhibits no sequence dependence[43, 50, 56, 63]. Consequently, the reporter signal as measured by luciferase activity is one of the highest reported, even higher than AAV transduction which can deliver only one reporter molecule per transduction event.

The second barrier that the T4-AVs breaks through is the all-in-one delivery. As demonstrated throughout our studies, the T4-AVs efficiently deliver complex cargos consisting of combinations of DNAs, proteins, RNAs, and their complexes. This is essential for many genome remodeling applications including genome editing and gene recombination that require co-delivery of multiple biomolecules, which is either currently not possible, or very difficult, with other delivery platforms[36, 62]. For example, for genome editing, AVs in different all-in-one configurations are assembled, carrying Cas9 nuclease and gRNAs either as functional RNA-protein complexes displayed outside and/or as expressible genes packaged inside. Similarly, for gene recombination, a variety of AVs are assembled that co-deliver the site-specific recombinase Cre and the donor plasmid.

The third barrier that the T4-AVs breaks through is multiplex delivery. T4-AVs are assembled by incorporating cargo molecules not only to target multiple sites (e.g., multiple gRNAs and siRNAs) but also to perform different molecular operations in the human genome. In one combination, three different operations; genome editing, gene expression, and site-specific recombination are performed by incorporating Cas9 and gRNA as RNPs, GFP or Luci genes as packaged plasmids, and Cre recombinase and donor plasmid as displayed and packaged molecules, respectively. In another combination, gene silencing, gene expression, and genome editing are performed by incorporating siRNAs, mRNA, Cas9, and gRNAs into the same artificial virus.

The fourth barrier that the T4-AVs breaks through is programmability, ability to carry out a set of instructions and also modify function upon entry into human cells. Many examples cited above demonstrate the execution of a set of instructions that each AV is programmed with. Modification of the functional behavior upon entry has also been demonstrated by the repurposing of Cas9 function. By taking advantage of the in vitro observation that Cas9 can bind to both single-stranded gRNA and double-stranded siRNA, and that the gRNA can dislodge bound siRNA due to its higher affinity for Cas9, AVs are assembled by displaying Cas9-siRNA complex and packaging gRNA expression plasmid. Upon entry, these AVs deliver siRNA into the cytosol that result in gene silencing while the same Cas9 then switch function to genome editing in the nucleus by binding to gRNA expressed from the co-delivered plasmid.

The programmability of T4-AVs is further enhanced by CRISPR engineering, which allow the incorporation of hundreds of protein molecules inside the phage capsid[32, 53]. Importantly, this created another avenue to generate additional functional circuits inside the packaged head that would lend itself to guiding intracellular trafficking and/or more effective genome modifications. These have been demonstrated using model proteins such as LacI and Cre. By pre-packaging LacI protein inside the capsid, it allows the formation of DNA-protein complexes between LacI protein and LacO-containing DNA arriving into the capsid in trans through in vitro DNA packaging. Once delivered, the engineered LacI with its nuclear localization signal then guide the DNA to nucleus as evident from enhanced reporter gene expression. Similarly, capsid-packaged NLS-Cre recombinase leads to near 100% efficiency of site-specific recombination in the human genome.

In conclusion, a new category of viral nanomaterial, phage-based artificial viruses, that can be custom-assembled in the test tube using an assembly-line approach is created. These artificial viruses possess similar architecture as natural viruses and go through similar pathways for entry, disassembly, and intracellular trafficking, although the exact mechanisms are not known and require further investigation[37, 48]. Importantly, however, from technology perspective, virtually unlimited varieties of AVs can be assembled using this approach that can faithfully execute functions each is programmed with and make precise alterations in genome and cellular metabolism. The systematic studies described in the present disclosure thus provide the necessary foundation to optimize payloads and create artificial viruses for efficient delivery into primary human cells that would lend itself for ex vivo cellular therapies such as stem cell and CAR T-cell therapies as well as in vivo therapies. These studies are in progress. With features such as large cargo capacity, ability to incorporate diverse cargos, programmability, customizability, and all-in-one delivery, this T4-AV platform established a powerful proof of concept for potential future applications to restore the health of defective human cells and ultimately the human body.

Having described the many embodiments of the present disclosure in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

Recombinant Protein Expression and Purification

Recombinant proteins (with the exception of Cas9 and Cpf1) were expressed by transforming the pET28b expressing plasmid in *Escherichia coli* (*E. coli*) BL21 (DE3) RIPL cells by the heat-shock method. The transformed cells were grown to an OD600 of 0.5 at 37° C. in Moores medium (20 g of tryptone, 15 g of yeast extract, 8 g of NaCl, 2 g of dextrose, 2 g of $Na_2HPO_4$, and 1 g of $KH_2PO_4$ dissolved in 1 L of Milli-Q® water) containing 50 µg/ml kanamycin and 25 µg/ml chloramphenicol, and protein expression was induced by 1 mM isopropyl β-d-1-thiogalactopyranoside (IPTG) at 30° C. for 3 h. After induction, cells were harvested by centrifugation, and the pellets are suspended in binding buffer (50 mM Tris-HCl, 300 mM NaCl and 20 mM imidazole, pH 8.0) containing proteinase inhibitor cocktail (Roche®, USA) and benzonase nuclease (Millipore Sigma®). The cell suspension was lysed by French press (Aminco®), and the soluble fraction was isolated from cellular debris by centrifugation at 34,000×g for 30 min. The lysate was filtered through 0.22-micron filters (Millipore®, Stericup®) and applied to a pre-equilibrated (binding buffer) HisTrapHP column (AKTA-Prime®, GE® Healthcare) and washed with binding buffer. The His-tagged protein was then eluted with a 20-500 mM linear imidazole gradient. The peak fractions were further purified by size exclusion chromatography using the Hi-Load 16/60 Superdex-200 (prep-grade) gel filtration column (GE® Healthcare) in GF buffer (20 mM Tris-HCl and 100 mM NaCl, pH 8.0) according to the manufacturer's instructions. The fractions containing the desired protein were pooled and concentrated by AmiconUltra-4 centrifugal filtration (10 kDa cut-off; Millipore®), flash-frozen in liquid nitrogen and stored at −80° C. All the column operations are performed at 4° C. Gel filtration molecular size standards were chromatographed on the same column to calculate the approximate size of the purified protein.

For Cas9-Soc or Cpf1-Soc purification, the recombinant SpCas9 or LbCpf1 used in this study was fused to Soc at the C-terminus and to nuclear localization signal peptide at the N-terminus. The protein also has a C-terminal hexa-histidine tag. Briefly, RIPL cells were cultured at 37° C. until OD600=0.6 and incubated at 20° C. for 40 min, then induced with 1 mM IPTG. After 20 h, the cells were collected and resuspended in 50 ml of binding buffer (50 mM Tris-HCl, 300 mM NaCl, 20 mM imidazole, and 5 mM Tris (2-carboxyethyl) phosphine (TCEP; Soltec Ventures), pH 8.0) containing proteinase inhibitor cocktail (Roche®, USA) and benzonase nuclease (Millipore Sigma®). The Cas9-Soc or Cpf1-Soc proteins were then purified by HisTrapHP and Superdex-200 columns as described above.

Example 2

T4 CRISPR Engineering

T4 phage engineering was performed according to a previously described procedure[53]. *E. coli* strains P301 (sup$^0$) and B40 (sup$^1$) were used in the experiments described below. The 10-amber 13-amber hoc-del soc-del T4 phage was propagated on *E. coli* B40 as described previously[63]. CRISPR-Cas9 or Cpf1 plasmids with specific spacer(s) were constructed by cloning spacer sequences into the streptomycin-resistant plasmid DS-SPCas (Addgene® No. 48645) (SEQ ID No. 21). The spacer sequences are shown below:

```
AAVS1-Cas9-gRNA1:
                        (SEQ ID NO: 2)
GTCCCCTCCACCCCACAGTG

AAVS1-Cas9-gRNA2:
                        (SEQ ID NO: 3)
GGGGCCACTAGGGACAGGAT

HBB-Cas9-gRNA:
                        (SEQ ID NO: 4)
AGTCTGCCGTTACTGCCCTG ipIII-Cas9-gRNA:
                        (SEQ ID NO: 5)
GGCCTTTACTACAGAAGCTT ipI-Cpf1-gRNA1:
                        (SEQ ID NO: 6)
TTCAGCAGGAGAGATAACGATTG ipI-Cpf1-gRNA2:
                        (SEQ ID NO: 7)
TACCATTACCGAAGCTACTCTTA ipII-Cpf1-gRNA1:
                        (SEQ ID NO: 8)
CTTCTAAGTTCGGCATGTCTATG ipII-Cpf1-gRNA2:
                        (SEQ ID NO: 9)
TTACGGTCTTTATCGGGCAA ipIII-Cpf1-gRNA1:
                        (SEQ ID NO: 10)
AAGTCGGAAGCCTTTGTAGCTAA ipIII-Cpf1-gRNA2:
                        (SEQ ID NO: 11)
TGCTTGGCAAATTCAAGACCTGC
```

The homologous donor plasmids were constructed by cloning the donor DNA into the pET28b vector. The CRISPR-Cas9/Cpf1 and donor plasmids are co-transformed into a suppressor containing *E. coli* B40 (sup$^1$), and then the positive clones are selected by streptomycin and kanamycin antibiotics. The cells transformed with either the CRISPR plasmid or the donor plasmid are used as controls. The cells were infected with WT or 10-amber 13-amber hoc-del soc-del T4 phages. The engineered genome of the progeny plaques was amplified and sequenced to confirm the insertion or deletion.

Example 3

T4 Heads Purification

The 10-amber 13-amber hoc-del soc-del T4 heads or protein-packaged GIS-T4 were isolated according to previously described protocols[63]. Briefly, *E. coli* P301 (sup-) cells infected with mutant phages (500 ml of culture) were lysed in 40 ml of Pi-Mg buffer (26 mM Na$_2$HPO$_4$, 68 mM NaCl, 22 mM KH$_2$PO$_4$, and 1 mM MgSO$_4$, pH 7.5) supplemented with 10 µg/ml DNase I and 1 ml of chloroform, followed by incubation at 37° C. for 30 min to digest the DNA. After two rounds of low-speed (6,000×g for 10 min) and high-speed (35,000×g for 45 min) centrifugation, the pellet is resuspended in 200 µl of Tris·Mg buffer (10 mM Tris-HCl, 50 mM NaCl, and 5 mM MgCl$_2$, pH 7.5), followed by CsCl density gradient centrifugation. The extracted T4 heads were dialyzed overnight against Tris·Mg buffer and further purified by DEAE-Sepharose chromatography. The peak capsid fractions were concentrated and stored at −80° C. The number of particles were determined by quantification of the major capsid protein gp23* in comparison with the known amounts of phage T4, using SDS-PAGE and laser densitometry.

Example 4

DNA Packaging Assays

In vitro DNA packaging assays were performed according to a previously described procedure[24]. The purified full-length gp17 (~3 µM), the linearized DNA in packaging buffer (30 mM Tris-HCl, 100 mM NaCl, 3 mM MgCl$_2$, and 1 mM ATP, pH 7.5), and the purified T4 heads (~2×10$^{10}$ particles) were sequentially added to constitute a 20 µl reaction mixture. The mixture was incubated at 37° C. for 45 min, followed by the addition of benzonase nuclease and incubation at 37° C. for 30 min to remove excess unpackaged DNA. The packaged nuclease-resistant DNAs were released by treatment with 0.5 µg/µl proteinase K (Fermentas®), 50 mM ethylenediaminetetraacetic acid (EDTA), and 0.2% SDS for 30 min at 65° C. The packaged DNA was analyzed using 1% (wt/vol) agarose gel electrophoresis. The amount of packaged DNA was quantified by Quantity One software (Bio-Rad®). The packaging efficiency was defined as the average number of DNA molecules packaged in one T4 head.

Example 5

Protein and RNA Display on the T4 Head

Protein display on the T4 head is performed according to the basic protocols described previously[27]. Briefly, after packaging linearized DNA as above, Soc- and/or Hoc-fusion proteins were added to the packaging mixture at different ratios and incubated at 4° C. for 1 h. The mixtures were sedimented by centrifugation at 30,000×g for 1 h, and unbound proteins in the supernatants were removed. After washing twice with PBS, the pellets were resuspended in PBS for SDS-PAGE analysis or Opti-MEM for cell transduction. After Coomassie Blue R250 (Bio-Rad®) staining and destaining, the protein bands on SDS-PAGE gels were quantified by laser densitometry (PDSI, GE® Healthcare). The densities of Hoc, Soc, and gp23* bands in each lane were quantified independently, and the copy numbers of bound Hoc or Soc fusion molecules per T4 were calculated using gp23* band in each lane as the internal control (930 copies per T4 capsid). For gRNA/siRNA/mRNA display, T4 heads displayed with Hoc or Soc fusion protein molecules was resuspended in RNAase-free PBS buffer, and then incubated with RNA at 4° C. for 1 h. The T4-RNP complexes were sedimented by centrifugation at 30,000×g for 1 h, and unbound RNAs in the supernatants were removed. After washing twice with PBS, the pellets were resuspended in Opti-MEM for transduction. To quantify the binding of RNA, the T4-RNP complex was treated with 0.5 µg/µl proteinase K (Fermentas®), 50 mM ethylenediaminetetraacetic acid (EDTA), and 0.2% SDS for 30 min at 65° C. to release the packaged DNA and displayed RNA, followed by agarose gel electrophoresis.

Example 6

T4-AV Assembly

The DNA-packaged and/or protein-displayed T4 nanoparticles as above were diluted in 50 µl of Opti-MEM and mixed gently. Meanwhile, 50 µl Opti-MEM medium was added to a separate sterile tube, followed by addition of an appropriate amount of cationic lipids such as lipofectamine 2000, lipofectamine 3000, lipofectamine RNAiMAX, lipofectamine LTX, lipofectamine stem, and ExpiFectamine® 293 (EXPI) (Thermo Scientific®). After 5 min incubation, the T4 particles were added, gently mixed, and incubated for 20 minutes at room temperature without shaking to allow the formation of T4-AVs. The total volume of the mixture is 100 µl.

Example 7

Cell Culture

HEK293 cells were cultured in Dulbecco's Modified Eagle's Medium (DMEM, Gibco®) supplemented with 10% fetal bovine serum (FBS, Invitrogen®), 1× HEPES (Gibco®), and 1% antibiotics (Gibco®) (complete DMEM). Cells were maintained in a humidified atmosphere at 37° C. and 5% $CO_2$ and grown until ~80-90% confluent. Cells were then dissociated from adherent surfaces using 0.05% trypsin/EDTA (Gibco®) and passaged at a subcultivation ratio of 1:5.

Example 8

Cell Transduction

One day prior to transduction, HEK293 cells were transferred to 24-well plates at $2\times10^5$ cells per well in complete DMEM. On the day of transduction, the cells were incubated with T4-AVs in antibiotic-free Opti-MEM for 6 h. Thereafter, Opti-MEM was removed and replaced with complete DMEM. The cells were further incubated at 37° C. for an additional 48 h for further analysis. GFP/mCherry transgene expression was observed by fluorescence microscopy (Carl Zeiss®) at 48 h post-transduction, and the average fluorescence intensities were quantified by ImageJ software. The nucleus was counterstained with Hoechst 33342 (Thermo Scientific®) at 37° C. for 20 min.

Example 9

Quantification of Luciferase Activity

To analyze luciferase gene delivery into cells by T4-AVs, luciferase activity was measured with the Luciferase Assay System (Promega®, USA) according to manufacturer's recommended protocol. Briefly, growth medium was removed, and cells were rinsed with PBS buffer. After removing the wash buffer, 150 µl of passive lysis buffer was added to each well, followed by gentle shaking at room temperature for 20 min. Twenty microliters of the cell lysate were then transferred to a 96-well white opaque plate and mixed with 80 µl of Luciferase Assay Reagent, and the luminescence signal was recorded by the Glomax Multi Detection System (Promega®). Triplicate measurements were applied to each group.

Example 10

Beta Galactosidase (β-gal) Transduction

The activity of the Soc-β-gal enzyme delivered by T4-AVs into cells was determined by staining with X-Gal using the β-Galactosidase Staining kit (Sigma®). The representative staining images were captured by ChemiDoc Imaging System (Bio-Rad®).

Example 11

Effect of Endocytosis Inhibitors

Cells were seeded in 24-well plates at $2\times10^5$ cells per well in complete DMEM. After 24 h, the cells were pre-incubated in antibiotic-free Opti-MEM for 30 min, with several inhibitors such as sucrose/chlorpromazine for clathrin-mediated endocytosis, methyl-β-cyclodextrin (M-β-CD) for lipid raft, dynasore for dynamin-mediated endocytosis, amiloride for macropinocytosis, nystatin for caveolin-mediated endocytosis, and cytochalasin D for actin cytoskeleton rearrangement. The cells were then exposed to T4-AVs packaged with luciferase or GFP reporter gene for another 6 h in the presence of the inhibitors. Thereafter, Opti-MEM was removed and replaced with complete DMEM. The cells were further incubated at 37° C. for an additional 48 h for luciferase or GFP signal analysis.

Example 12

Cell Proliferation Assay

Cell viability was determined using the CellTiter-Glo® Luminescent Cell Viability Assay Kit (Promega®) after transfection for 48 h following the manufacturer's protocol. Briefly, an equal volume of CellTiter-Glo® Reagent was added to the cell culture in each well. The mixture was horizontally shaken for 2 min to induce cell lysis and then incubated at room temperature for 10 min to stabilize the luminescence signal, which was then recorded by the Glomax® Multi Detection System (Promega®). The viability of the untreated cell group was normalized to 100%, and triplicate measurements were applied to each sample.

Example 13

Western Blotting Analyses

Briefly, the transduced cells were resuspended in loading buffer and boiled for 10 min, separated by 12% SDS-PAGE, and then transferred to nitrocellulose membranes (Bio-Rad®). Blocking was performed in 5% BSA/PBS-T buffer (PBS with 0.05% Tween-20, pH 7.4) at room temperature for 1 h with gentle shaking. Blots were then washed three times with PBS-T. Primary anti-GFP, anti-tubulin, or anti-His6 antibodies were added to the blots and incubated overnight at 4° C. in PBS with 5% BSA. After washing with PBS-T three times, a secondary goat anti-mouse HRP-conjugated antibody (Invitrogen®) was applied at a 1:10,000 dilution in 5% BSA/PBS-T for 1 h at room temperature, followed by rinsing three times with PBS-T. Signals were visualized with an enhanced chemiluminescence substrate

Example 14

Genomic DNA Extraction and T7EI Assay for Genome Modification

HEK293 cells were transfected with various genome editing AVs as described in the present disclosure. Cells were incubated at 37° C. for 72 h post-transduction. Genomic DNA was purified using the GeneJET™ Genomic DNA Purification kit (Thermo Scientific®) following the manufacturer's instructions. Briefly, cells were resuspended in a lysis solution/Proteinase K and incubated at 56° C. for 10 min, followed by the treatment with RNAase A at room temperature for 10 min. GeneJET™ column was used to absorb genomic DNA and washed with wash buffer. Genomic DNA was eluted with elution buffer and stored at −20° C. Genomic region surrounding the AAVS1 or HBB target site was amplified, and PCR products were purified using Qiagen® Mini kit (Qiagen®) following the manufacturer's protocol. A total of 400 ng or 200 ng of the purified PCR products were mixed with 2 µl 10× NEB® buffer 2 (NEB®) and nuclease-free water to a final volume of 20 µl, and annealed to enable heteroduplex formation using the following incubations: 95° C. for 10 min, 95° C. to 85° C. ramping at −2° C./s, 85° C. to 25° C. at −0.1° C./s, and 4° C. for hold. T7 Endonuclease I was then added to the annealed PCR product and incubated at 37° C. for 30 min. T7EI digestion product was analyzed on 1.5% (wt/vol) agarose gel. Gels were imaged with a GelDoc® gel imaging system (Bio-Rad®) and quantification was based on relative band intensities using ImageJ software. The estimated gene modification was calculated using the following formula: indel (%)=100×(1−(1−fraction cleaved)$^{1/2}$)$^{36}$.

Example 15

AAVS1 gRNA In Vitro Synthesis

A DNA template (SEQ ID NO: 1) containing the T7 promoter, the gRNA target and the gRNA scaffold sequences for Cas9 was amplified by PCR with Phusion High-Fidelity PCR Master Mix (Thermo Scientific®). The T7-gRNA PCR fragment was gel-purified and used as a template for in vitro transcription using the HiScribe T7 High Yield RNA Synthesis Kit (NEB®). T7 transcription was performed overnight, and then RNA was purified using the MEGAclear Transcription Clean-Up Kit (Thermo Scientific®). The gRNA was eluted with RNase-free water, analyzed by agarose gel electrophoresis, quantified with Nanodrop® 2000 (Thermo Scientific®), and stored at −80° C.

Example 16

In Vitro CRISPR RNP Binding and Cleavage Assay

To test the binding of Cas9 or Cas9-Soc to gRNA/siRNA/mRNA, the purified protein and RNA at different ratios were incubated at room temperature for 1 h, and then analyzed by agarose gel electrophoresis. The genomic region surrounding the AAVS1 target site was amplified by PCR with Hot-Start DNA Polymerases (Thermo Scientific®), purified by Qiagen® Mini kit (Qiagen®), and used as the substrate for Cas9 cleavage assay. In a reaction volume of 20 µl containing NEB® buffer 3 (100 mM NaCl, 50 mM Tris-HCl, 10 mM MgCl$_2$, and 1 mM DTT, pH 7.9) and PCR product (300 ng), purified Cas9 or Cas9-Soc (50 nM) and AAVS1gRNA (50 nM) were added. After incubation for 1 h at 37° C., the DNA was analyzed by 1.5% (wt/vol) agarose gel electrophoresis.

Example 17

In Vitro Cre-Hoc Recombination Assay

LSL-GFP plasmid was used as the substrate for testing Cre-Hoc recombination in vitro. In a reaction volume of 50 µl containing recombination buffer (33 mM NaCl, 50 mM Tris-HCl, and 10 mM MgCl$_2$, pH 7.5) and LSL-GFP plasmid, increasing amounts of purified Cre-Hoc protein were added. After incubation at 37° C. for 30 min and then at 70° C. for 10 minutes, the DNA was analyzed by 0.8% (wt/vol) agarose gel electrophoresis.

Example 18

Enzyme-Linked Immunosorbent Assay (ELISA) for VRCO1 Antibody and CH58 Antibody Quantification HEK293 cells were transduced with AVs packaged with the linearized plasmids expressing the heavy chain and light chain of VRC01 and/or CH58. After culturing for 3 days, cell culture supernatants were harvested and analyzed for the concentration of antibody by ELISA. ELISA plates (Evergreen Scientific®, 96-well) were coated with 0.1 µg of HIV-1JRFL gp140 envelope protein per well in coating buffer (0.05 M sodium carbonate-sodium bicarbonate, pH 9.6) overnight at 4° C. After washing three times with PBS buffer (pH 7.4), the plates were blocked with PBS-3% BSA buffer for 1 h at 37° C. Known quantities of purified VRCO1 or CH58 monoclonal antibodies in five-fold serial dilution were added to triplicate wells to generate a standard curve, with a starting concentration of 2000 ng mL$^{-1}$. The concentrations of VRCO1 or CH58 in cell culture medium were determined using a 5-fold dilution series in PBS-1% BSA. The diluted samples were added to each well, and the plates were incubated at 37° C. for 1 h and washed five times with PBS-T buffer (PBS with 0.05% Tween-20, pH 7.4). The secondary goat anti-human IgG-HRP antibody was then added to each well at a 1:5000 dilution and incubated for 1 h at 37° C., followed by washing five times with PBS-T buffer. Next, the TMB (3,3',5,5'-tetramethylbenzidine) Microwell™ Peroxidase Substrate System (KPL) was applied in the dark for color development. After 10 min, the enzymatic reaction was quenched by adding TMB BlueSTOP™ (KPL) solution, and plates were read within 30 min at 650 nm using an ELISA reader (VERSA Max™, Molecular Devices).

Example 19

Statistics

All quantified data are shown as the mean±standard deviation (SD). Statistical analyses were performed by two-tailed Student's t-tests. The difference between the two groups was considered statistically significant when p<0.05 or highly significant when p<0.01.

REFERENCES

The following references are referred to above and are incorporated herein by reference:

1. Barr, J. J., Auro, R., Furlan, M., Whiteson, K. L., Erb, M. L., Pogliano, J., Stotland, A., Wolkowicz, R., Cutting, A. S., Doran, K. S., et al. (2013). Bacteriophage adhering to mucus provide a non-host-derived immunity. *Proceedings of the National Academy of Sciences of the United States of America* 110, 10771-10776.
2. Behzadi, S., Serpooshan, V., Tao, W., Hamaly, M.A., Alkawareek, M. Y., Dreaden, E. C., Brown, D., Alkilany, A. M., Farokhzad, O. C., and Mahmoudi, M. (2017). Cellular uptake of nanoparticles: journey inside the cell. *Chemical Society Reviews* 46, 4218-4244.
3. Butler, K. V., Kalin, J., Brochier, C., Vistoli, G., Langley, B., and Kozikowski, A. P. (2010). Rational design and simple chemistry yield a superior, neuroprotective HDAC6 inhibitor, tubastatin A. *Journal of the American Chemical Society* 132, 10842-10846.
4. Casjens, S. R. (2011). The DNA-packaging nanomotor of tailed bacteriophages. *Nature Reviews Microbiology* 9, 647-657.
5. Chen, Z., Sun, L., Zhang, Z., Fokine, A., Padilla-Sanchez, V., Hanein, D., Jiang, W., Rossmann, M. G., and Rao, V. B. (2017). Cryo-EM structure of the bacteriophage T4 isometric head at 3.3-A resolution and its relevance to the assembly of icosahedral viruses. *Proceedings of the National Academy of Sciences of the United States of America* 114, E8184-E8193.
6. Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. *Science* 339, 819-823.
7. D'Astolfo, D. S., Pagliero, R. J., Pras, A., Karthaus, W. R., Clevers, H., Prasad, V., Lebbink, R. J., Rehmann, H., and Geijsen, N. (2015). Efficient intracellular delivery of native proteins. *Cell* 161, 674-690.
8. Danhier, F., Le Breton, A., and Preat, V. (2012). RGD-based strategies to target alpha(v) beta(3) integrin in cancer therapy and diagnosis. *Molecular Pharmaceutics* 9, 2961-2973.
9. de Beer, T., Fang, J., Ortega, M., Yang, Q., Maes, L., Duffy, C., Berton, N., Sippy, J., Overduin, M., Feiss, M., et al. (2002). Insights into specific DNA recognition during the assembly of a viral genome packaging machine. *Molecular Cell* 9, 981-991.
10. DeKelver, R. C., Choi, V. M., Moehle, E. A., Paschon, D. E., Hockemeyer, D., Meijsing, S. H., Sancak, Y., Cui, X., Steine, E. J., Miller, J. C., et al. (2010). Functional genomics, proteomics, and regulatory DNA analysis in isogenic settings using zinc finger nuclease-driven transgenesis into a safe harbor locus in the human genome. *Genome Research* 20, 1133-1142.
11. Dion, M. B., Oechslin, F., and Moineau, S. (2020). Phage diversity, genomics and phylogeny. *Nature Reviews Microbiology* 18, 125-138.
12. Doherty, G. J., and McMahon, H. T. (2009). Mechanisms of endocytosis. *Annual Review of Biochemistry* 78, 857-902.
13. Dong, Y., Siegwart, D. J., and Anderson, D. G. (2019). Strategies, design, and chemistry in siRNA delivery systems. *Advanced Drug Delivery Reviews* 144, 133-147.
14. Escors, D., and Breckpot, K. (2010). Lentiviral vectors in gene therapy: their current status and future potential. *Archivum Immunologiae Et Therapiae Experimentalis* 58, 107-119.
15. Fang, Q., Tang, W. C., Tao, P., Mahalingam, M., Fokine, A., Rossmann, M. G., and Rao, V. B. (2020). Structural morphing in a symmetry-mismatched viral vertex. *Nature Communications* 11, 1713.
16. Fokine, A., Chipman, P. R., Leiman, P. G., Mesyanzhinov, V. V., Rao, V. B., and Rossmann, M. G. (2004). Molecular architecture of the prolate head of bacteriophage T4. *Proceedings of the National Academy of Sciences of the United States of America* 101, 6003-6008.
17. Fokine, A., Islam, M. Z., Zhang, Z., Bowman, V. D., Rao, V. B., and Rossmann, M. G. (2011). Structure of the three N-terminal immunoglobulin domains of the highly immunogenic outer capsid protein from a T4-like bacteriophage. *Journal of Virology* 85, 8141-8148.
18. Fuller, D. N., Rickgauer, J. P., Jardine, P. J., Grimes, S., Anderson, D. L., and Smith, D. E. (2007). Ionic effects on viral DNA packaging and portal motor function in bacteriophage phi 29. *Proceedings of the National Academy of Sciences of the United States of America* 104, 11245-11250.
19. Gao, X., Tao, Y., Lamas, V., Huang, M., Yeh, W. H., Pan, B., Hu, Y. J., Hu, J. H., Thompson, D. B., Shu, Y., et al. (2018). Treatment of autosomal dominant hearing loss by in vivo delivery of genome editing agents. *Nature* 553, 217-221.
20. Hernandez-Garcia, A., Kraft, D. J., Janssen, A. F., Bomans, P. H., Sommerdijk, N. A., Thies-Weesie, D. M., Favretto, M. E., Brock, R., de Wolf, F. A., Werten, M. W., et al. (2014). Design and self-assembly of simple coat proteins for artificial viruses. *Nature Nanotechnology* 9, 698-702.
21. Ishii, T., and Yanagida, M. (1977). The two dispensable structural proteins (soc and hoc) of the T4 phage capsid; their purification and properties, isolation and characterization of the defective mutants, and their binding with the defective heads in vitro. *Journal of Molecular Biology* 109, 487-514.
22. Johnson, J. E., and Chiu, W. (2007). DNA packaging and delivery machines in tailed bacteriophages. *Current Opinion in Structural Biology* 17, 237-243.
23. Kim, Y. B., Zhao, K. T., Thompson, D. B., and Liu, D. R. (2019). An anionic human protein mediates cationic liposome delivery of genome editing proteins into mammalian cells. *Nature Communications* 10, 2905.
24. Kondabagil, K. R., Zhang, Z., and Rao, V. B. (2006). The DNA translocating ATPase of bacteriophage T4 packaging motor. *Journal of Molecular Biology* 363, 786-799.
25. Leffers, G., and Rao, V. B. (1996). A discontinuous headful packaging model for packaging less than headful length DNA molecules by bacteriophage T4. *Journal of Molecular Biology* 258, 839-850.
26. Leiman, P. G., Chipman, P. R., Kostyuchenko, V. A., Mesyanzhinov, V. V., and Rossmann, M. G. (2004). Three-dimensional rearrangement of proteins in the tail of bacteriophage T4 on infection of its host. *Cell* 118, 419-429.
27. Li, Q., Shivachandra, S. B., Zhang, Z., and Rao, V. B. (2007). Assembly of the small outer capsid protein, Soc, on bacteriophage T4: a novel system for high density display of multiple large anthrax toxins and foreign proteins on phage capsid. *Journal of Molecular Biology* 370, 1006-1019.
28. Mali, P., Yang, L., Esvelt, K. M., Aach, J., Guell, M., DiCarlo, J. E., Norville, J. E., and Church, G. M. (2013). RNA-guided human genome engineering via Cas9. *Science* 339, 823-826.
29. Mastrobattista, E., van der Aa, M. A., Hennink, W. E., and Crommelin, D. J. (2006). Artificial viruses: a nanotechnological approach to gene delivery. *Nature Reviews Drug Discovery* 5, 115-121.

30. Meinke, G., Bohm, A., Hauber, J., Pisabarro, M. T., and Buchholz, F. (2016). Cre Recombinase and Other Tyrosine Recombinases. *Chemical Reviews* 116, 12785-12820.
31. Miller, E. S., Kutter, E., Mosig, G., Arisaka, F., Kunisawa, T., and Ruger, W. (2003). Bacteriophage T4 genome. *Microbiology and Molecular Biology Reviews: MMBR* 67, 86-156, table of contents.
32. Mullaney, J. M., and Black, L. W. (1996). Capsid targeting sequence targets foreign proteins into bacteriophage T4 and permits proteolytic processing. *Journal of Molecular Biology* 261, 372-385.
33. Muzyczka, R. J. S. a. N. (2014). AAV-Mediated Gene Therapy for Research and Therapeutic Purposes. *Annual Review of Virology,* 427-451.
34. Natarajan, P., Lander, G. C., Shepherd, C. M., Reddy, V. S., Brooks, C. L., 3rd, and Johnson, J. E. (2005). Exploring icosahedral virus structures with VIPER. *Nature Reviews Microbiology* 3, 809-817.
35. Nayerossadat, N., Maedeh, T., and Ali, P. A. (2012). Viral and nonviral delivery systems for gene delivery. *Advanced Biomedical Research* 1, 27.
36. Nelson, C. E., and Gersbach, C. A. (2016). Engineering Delivery Vehicles for Genome Editing. *Annual Review of Chemical and Biomolecular Engineering* 7, 637-662.
37. Ni, R., Zhou, J., Hossain, N., and Chau, Y. (2016). Virus-inspired nucleic acid delivery system: Linking virus and viral mimicry. *Advanced Drug Delivery Reviews* 106, 3-26.
38. Paez-Espino, D., Eloe-Fadrosh, E. A., Pavlopoulos, G. A., Thomas, A. D., Huntemann, M., Mikhailova, N., Rubin, E., Ivanova, N. N., and Kyrpides, N. C. (2016). Uncovering Earth's virome. *Nature* 536, 425-430.
39. Qin, L., Fokine, A., O'Donnell, E., Rao, V. B., and Rossmann, M. G. (2010). Structure of the small outer capsid protein, Soc: a clamp for stabilizing capsids of T4-like phages. *Journal of Molecular Biology* 395, 728-741.
40. Ran, F. A., Hsu, P. D., Wright, J., Agarwala, V., Scott, D. A., and Zhang, F. (2013). Genome engineering using the CRISPR-Cas9 system. Nature protocols 8, 2281-2308.
41. Rao, V. B., and Feiss, M. (2008). The bacteriophage DNA packaging motor. *Annual Review of Genetics* 42, 647-681.
42. Rao, V. B., and Feiss, M. (2015). Mechanisms of DNA Packaging by Large Double-Stranded DNA Viruses. *Annu Rev Virol* 2, 351-378.
43. Rao, V. B., Thaker, V., and Black, L. W. (1992). A phage T4 in vitro packaging system for cloning long DNA molecules. *Gene* 113, 25-33.
44. Rauch, B. J., Silvis, M. R., Hultquist, J. F., Waters, C. S., McGregor, M. J., Krogan, N. J., and Bondy-Denomy, J. (2017). Inhibition of CRISPR-Cas9 with Bacteriophage Proteins. *Cell* 168, 150-158 e110.
45. Robertson, K., Furukawa, Y., Underwood, A., Black, L., and Liu, J.L. (2012). Deletion of the Hoc and Soc capsid proteins affects the surface and cellular uptake properties of bacteriophage T4 derived nanoparticles. *Biochemical and Biophysical Research Communications* 418, 537-540.
46. Sahin, U., Kariko, K., and Tureci, O. (2014). mRNA-based therapeutics—developing a new class of drugs. *Nature Reviews Drug Discovery* 13, 759-780.
47. Shivachandra, S. B., Rao, M., Janosi, L., Sathaliyawala, T., Matyas, G. R., Alving, C. R., Leppla, S. H., and Rao, V. B. (2006). In vitro binding of anthrax protective antigen on bacteriophage T4 capsid surface through Hoc-capsid interactions: a strategy for efficient display of large full-length proteins. *Virology* 345, 190-198.
48. Stewart, M. P., Sharei, A., Ding, X., Sahay, G., Langer, R., and Jensen, K. F. (2016). In vitro and ex vivo strategies for intracellular delivery. *Nature* 538, 183-192.
49. Sun, L., Zhang, X., Gao, S., Rao, P. A., Padilla-Sanchez, V., Chen, Z., Sun, S., Xiang, Y., Subramaniam, S., Rao, V. B., et al. (2015). Cryo-EM structure of the bacteriophage T4 portal protein assembly at near-atomic resolution. *Nature Communications* 6, 7548.
50. Sun, S., Kondabagil, K., Draper, B., Alam, T. I., Bowman, V. D., Zhang, Z., Hegde, S., Fokine, A., Rossmann, M. G., and Rao, V. B. (2008). The structure of the phage T4 DNA packaging motor suggests a mechanism dependent on electrostatic forces. *Cell* 135, 1251-1262.
51. Tao, P., Mahalingam, M., Marasa, B.S., Zhang, Z., Chopra, A. K., and Rao, V. B. (2013). In vitro and in vivo delivery of genes and proteins using the bacteriophage T4 DNA packaging machine. *Proceedings of the National Academy of Sciences of the United States of America* 110, 5846-5851.
52. Tao, P., Wu, X., and Rao, V. (2018a). Unexpected evolutionary benefit to phages imparted by bacterial CRISPR-Cas9. *Science Advances* 4, eaar4134.
53. Tao, P., Wu, X., Tang, W. C., Zhu, J., and Rao, V. (2017). Engineering of Bacteriophage T4 Genome Using CRISPR-Cas9. *ACS Synthetic Biology* 6, 1952-1961.
54. Tao, P., Zhu, J., Mahalingam, M., Batra, H., and Rao, V. B. (2018b). Bacteriophage T4 nanoparticles for vaccine delivery against infectious diseases. *Advanced Drug Delivery Reviews*.
55. Torchilin, V. P., Rammohan, R., Weissig, V., and Levchenko, T. S. (2001). TAT peptide on the surface of liposomes affords their efficient intracellular delivery even at low temperature and in the presence of metabolic inhibitors. *Proceedings of the National Academy of Sciences of the United States of America* 98, 8786-8791.
56. Vafabakhsh, R., Kondabagil, K., Earnest, T., Lee, K. S., Zhang, Z., Dai, L., Dahmen, K. A., Rao, V. B., and Ha, T. (2014). Single-molecule packaging initiation in real time by a viral DNA packaging machine from bacteriophage T4. *Proceedings of the National Academy of Sciences of the United States of America* 111, 15096-15101.
57. van Meer, G., Voelker, D. R., and Feigenson, G. W. (2008). Membrane lipids: where they are and how they behave. *Nature Reviews Molecular Cell Biology* 9, 112-124.
58. Wang, M., Zuris, J. A., Meng, F., Rees, H., Sun, S., Deng, P., Han, Y., Gao, X., Pouli, D., Wu, Q., et al. (2016). Efficient delivery of genome-editing proteins using bioreducible lipid nanoparticles. *Proceedings of the National Academy of Sciences of the United States of America.*
59. Wu, F., Zhao, S., Yu, B., Chen, Y. M., Wang, W., Song, Z. G., Hu, Y., Tao, Z. W., Tian, J. H., Pei, Y. Y., et al. (2020). A new coronavirus associated with human respiratory disease in China. *Nature* 579, 265-269.

60. Yap, M. L., and Rossmann, M. G. (2014). Structure and function of bacteriophage T4. *Future Microbiology* 9, 1319-1327.
61. Yin, H., Kanasty, R. L., Eltoukhy, A. A., Vegas, A. J., Dorkin, J. R., and Anderson, D. G. (2014). Non-viral vectors for gene-based therapy. *Nature Reviews Genetics* 15, 541-555.
62. Yin, H., Kauffman, K. J., and Anderson, D. G. (2017). Delivery technologies for genome editing. *Nature Reviews Drug Discovery* 16, 387-399.
63. Zhang, Z., Kottadiel, V. I., Vafabakhsh, R., Dai, L., Chemla, Y. R., Ha, T., and Rao, V. B. (2011). A promiscuous DNA packaging machine from bacteriophage T4. *PLoS Biology* 9, e1000592.
64. Zhou, T., Georgiev, I., Wu, X., Yang, Z. Y., Dai, K., Finzi, A., Kwon, Y. D., Scheid, J. F., Shi, W., Xu, L., et al. (2010). Structural basis for broad and potent neutralization of HIV-1 by antibody VRC01. *Science* 329, 811-817.
65. Zhu, J., Tao, P., Mahalingam, M., Sha, J., Kilgore, P., Chopra, A. K., and Rao, V. (2019). A prokaryotic-eukaryotic hybrid viral vector for delivery of large cargos of genes and proteins into human cells. *Science Advances* 5, eaax0064.
66. Zuris, J. A., Thompson, D. B., Shu, Y., Guilinger, J. P., Bessen, J. L., Hu, J. H., Maeder, M. L., Joung, J. K., Chen, Z. Y., and Liu, D. R. (2015). Cationic lipid-mediated delivery of proteins enables efficient protein-based genome editing in vitro and in vivo. *Nature Biotechnology* 33, 73-80.
67. Black L W, Showe M K, Steven A C (1994) Morphogenesis of the T4 head. In: Karam J D (ed) Molecular biology of bacteriophage T4. American Society for Microbiology Press, Washington, D.C., pp 218-258

All documents, patents, journal articles and other materials cited in the present application are incorporated herein by reference.

While the present disclosure has been disclosed with references to certain embodiments, numerous modifications, alterations, and changes to the described embodiments are possible without departing from the sphere and scope of the present disclosure, as defined in the appended claims. Accordingly, it is intended that the present disclosure not be limited to the described embodiments, but that it has the full scope defined by the language of the following claims, and equivalents thereof.

What is claimed is:

1. A human genome remodeling artificial virus (AV) comprising:
   a T4 capsid;
   a Cas9 protein;
   at least one RNA;
   at least one DNA; and
   a lipid coating,
   wherein the DNA is packaged inside the T4 capsid;
   wherein the RNA is selected from the group consisting of a mRNA, a siRNA, and a gRNA,
   wherein the lipid coating comprises at least one cationic lipid.

2. The AV of claim 1, wherein the Cas9 protein and RNA form ribonucleoprotein (RNP) complex and wherein the Cas9 protein is connected to the T4 capsid through at least one protein selected from the group consisting of Hoc and Soc.

3. The AV of claim 2, wherein a Cas9-Soc comprises a sequence set forth in SEQ ID NO: 16.

4. The AV of claim 1, wherein at least one of the Cas9 protein, a Cpf1 protein, the RNA, a Cre, a DNA ligase, and a RNA polymerase is packaged inside the T4 capsid.

5. The AV of claim 1 further comprising a site-specific recombinase Cre, displayed outside the T4 capsid through at least one protein selected from the group consisting of Hoc and Soc.

6. The AV of claim 5, wherein Cre-Hoc comprises a sequence set forth in SEQ ID NO: 18, and Cre-Soc comprises a sequence set forth in SEQ ID NO: 22.

* * * * *

SEQUENCE LISTING

<160> NUMBER OF SEQ ID NOS: 22

<210> SEQ ID NO 1
<211> LENGTH: 120
<212> TYPE: DNA
<213> ORGANISM: Artificial Sequence
<220> FEATURE:
<223> OTHER INFORMATION: Synthetic: DNA template for AAVS1gRNA in vitro
      synthesis

<400> SEQUENCE: 1
aagcaatacg actcactata ggggccacta gggacaggat gttttagagc tagaaatagc      60
aagttaaaat aaggctagtc cgttatcaac ttgaaaaagt ggcaccgagt cggtgctttt     120

<210> SEQ ID NO 2
<211> LENGTH: 20
<212> TYPE: DNA
<213> ORGANISM: Artificial Sequence
<220> FEATURE:
<223> OTHER INFORMATION: Synthetic: AAVS1-Cas9-gRNA1

<400> SEQUENCE: 2
gtcccctcca ccccacagtg                                                  20

<210> SEQ ID NO 3
<211> LENGTH: 20
<212> TYPE: DNA
<213> ORGANISM: Artificial Sequence
<220> FEATURE:
<223> OTHER INFORMATION: Synthetic: AAVS1-Cas9-gRNA2

<400> SEQUENCE: 3
ggggccacta gggacaggat                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic: HBB-Cas9-gRNA

```
<400> SEQUENCE: 4
agtctgccgt tactgccctg                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic: ipIII-Cas9-gRNA

<400> SEQUENCE: 5
ggcctttact acagaagctt                                              20

<210> SEQ ID NO 6
<211> LENGTH: 23
<212> TYPE: DNA
<213> ORGANISM: Artificial Sequence
<220> FEATURE:
<223> OTHER INFORMATION: Synthetic: ipI-Cpf1- gRNA1

<400> SEQUENCE: 6
ttcagcagga gagataacga ttg                                          23

<210> SEQ ID NO 7
<211> LENGTH: 23
<212> TYPE: DNA
<213> ORGANISM: Artificial Sequence
<220> FEATURE:
<223> OTHER INFORMATION: Synthetic: ipI-Cpf1-gRNA2

<400> SEQUENCE: 7
taccattacc gaagctactc tta                                          23

<210> SEQ ID NO 8
<211> LENGTH: 23
<212> TYPE: DNA
<213> ORGANISM: Artificial Sequence
<220> FEATURE:
<223> OTHER INFORMATION: Synthetic: ipII-Cpf1-gRNA1

<400> SEQUENCE: 8
cttctaagtt cggcatgtct atg                                          23

<210> SEQ ID NO 9
<211> LENGTH: 20
<212> TYPE: DNA
<213> ORGANISM: Artificial Sequence
<220> FEATURE:
<223> OTHER INFORMATION: Synthetic: ipII-Cpf1-gRNA2

<400> SEQUENCE: 9
ttacggtctt tatcgggcaa                                              20

<210> SEQ ID NO 10
<211> LENGTH: 23
<212> TYPE: DNA
<213> ORGANISM: Artificial Sequence
<220> FEATURE:
<223> OTHER INFORMATION: Synthetic: ipIII-Cpf1-gRNA1

<400> SEQUENCE: 10
aagtcggaag cctttgtagc taa                                          23

<210> SEQ ID NO 11
<211> LENGTH: 23
```

```
<212> TYPE: DNA
<213> ORGANISM: Artificial Sequence
<220> FEATURE:
<223> OTHER INFORMATION: Synthetic: ipIII-Cpf1-gRNA2

<400> SEQUENCE: 11
tgcttggcaa attcaagacc tgc                                    23

<210> SEQ ID NO 12
<211> LENGTH: 20
<212> TYPE: DNA
<213> ORGANISM: Artificial Sequence
<220> FEATURE:
<223> OTHER INFORMATION: Synthetic: P1

<400> SEQUENCE: 12
ctgccgtctc tctcctgagt                                        20

<210> SEQ ID NO 13
<211> LENGTH: 20
<212> TYPE: DNA
<213> ORGANISM: Artificial Sequence
<220> FEATURE:
<223> OTHER INFORMATION: Synthetic: P2

<400> SEQUENCE: 13
gtgggcttgt actcggtcat                                        20

<210> SEQ ID NO 14
<211> LENGTH: 20
<212> TYPE: DNA
<213> ORGANISM: Artificial Sequence
<220> FEATURE:
<223> OTHER INFORMATION: Synthetic: P3

<400> SEQUENCE: 14
aaaactgacg cacggaggaa                                        20

<210> SEQ ID NO 15
<211> LENGTH: 20
<212> TYPE: DNA
<213> ORGANISM: Artificial Sequence
<220> FEATURE:
<223> OTHER INFORMATION: Synthetic: P4

<400> SEQUENCE: 15
gtggattcgg gtcacctctc                                        20

<210> SEQ ID NO 16
<211> LENGTH: 1462
<212> TYPE: PRT
<213> ORGANISM: Artificial Sequence
<220> FEATURE:
<223> OTHER INFORMATION: Synthetic: Cas9-Soc

<400> SEQUENCE: 16

Pro Lys Lys Lys Arg Lys Val Met Asp Lys Lys Tyr Ser Ile Gly Leu
1               5                   10                  15

Asp Ile Gly Thr Asn Ser Val Gly Trp Ala Val Ile Thr Asp Glu Tyr
            20                  25                  30

Lys Val Pro Ser Lys Lys Phe Lys Val Leu Gly Asn Thr Asp Arg His
        35                  40                  45

Ser Ile Lys Lys Asn Leu Ile Gly Ala Leu Leu Phe Asp Ser Gly Glu
    50                  55                  60
```

```
Thr Ala Glu Ala Thr Arg Leu Lys Arg Thr Ala Arg Arg Tyr Thr
 65                  70                  75                  80

Arg Arg Lys Asn Arg Ile Cys Tyr Leu Gln Glu Ile Phe Ser Asn Glu
                 85                  90                  95

Met Ala Lys Val Asp Asp Ser Phe Phe His Arg Leu Glu Glu Ser Phe
            100                 105                 110

Leu Val Glu Glu Asp Lys Lys His Glu Arg His Pro Ile Phe Gly Asn
            115                 120                 125

Ile Val Asp Glu Val Ala Tyr His Glu Lys Tyr Pro Thr Ile His Leu
        130                 135                 140

Arg Lys Lys Leu Val Asp Ser Thr Asp Lys Ala Asp Leu Arg Leu Ile
145                 150                 155                 160

Tyr Leu Ala Leu Ala His Met Ile Lys Phe Arg Gly His Phe Leu Ile
                165                 170                 175

Glu Gly Asp Leu Asn Pro Asp Asn Ser Asp Val Asp Lys Leu Phe Ile
            180                 185                 190

Gln Leu Val Gln Thr Tyr Asn Gln Leu Phe Glu Glu Asn Pro Ile Asn
            195                 200                 205

Ala Ser Gly Val Asp Ala Lys Ala Ile Leu Ser Ala Arg Leu Ser Lys
210                 215                 220

Ser Arg Arg Leu Glu Asn Leu Ile Ala Gln Leu Pro Gly Glu Lys Lys
225                 230                 235                 240

Asn Gly Leu Phe Gly Asn Leu Ile Ala Leu Ser Leu Gly Leu Thr Pro
                245                 250                 255

Asn Phe Lys Ser Asn Phe Asp Leu Ala Glu Asp Ala Lys Leu Gln Leu
            260                 265                 270

Ser Lys Asp Thr Tyr Asp Asp Leu Asp Asn Leu Leu Ala Gln Ile
            275                 280                 285

Gly Asp Gln Tyr Ala Asp Leu Phe Leu Ala Ala Lys Asn Leu Ser Asp
        290                 295                 300

Ala Ile Leu Leu Ser Asp Ile Leu Arg Val Asn Thr Glu Ile Thr Lys
305                 310                 315                 320

Ala Pro Leu Ser Ala Ser Met Ile Lys Arg Tyr Asp Glu His His Gln
                325                 330                 335

Asp Leu Thr Leu Leu Lys Ala Leu Val Arg Gln Gln Leu Pro Glu Lys
            340                 345                 350

Tyr Lys Glu Ile Phe Phe Asp Gln Ser Lys Asn Gly Tyr Ala Gly Tyr
        355                 360                 365

Ile Asp Gly Gly Ala Ser Gln Glu Glu Phe Tyr Lys Phe Ile Lys Pro
        370                 375                 380

Ile Leu Glu Lys Met Asp Gly Thr Glu Glu Leu Leu Val Lys Leu Asn
385                 390                 395                 400

Arg Glu Asp Leu Leu Arg Lys Gln Arg Thr Phe Asp Asn Gly Ser Ile
                405                 410                 415

Pro His Gln Ile His Leu Gly Glu Leu His Ala Ile Leu Arg Arg Gln
            420                 425                 430

Glu Asp Phe Tyr Pro Phe Leu Lys Asp Asn Arg Glu Lys Ile Glu Lys
        435                 440                 445

Ile Leu Thr Phe Arg Ile Pro Tyr Tyr Val Gly Pro Leu Ala Arg Gly
        450                 455                 460

Asn Ser Arg Phe Ala Trp Met Thr Arg Lys Ser Glu Glu Thr Ile Thr
465                 470                 475                 480

Pro Trp Asn Phe Glu Glu Val Val Asp Lys Gly Ala Ser Ala Gln Ser
```

```
                485                 490                 495
Phe Ile Glu Arg Met Thr Asn Phe Asp Lys Asn Leu Pro Asn Glu Lys
                500                 505                 510

Val Leu Pro Lys His Ser Leu Leu Tyr Glu Tyr Phe Thr Val Tyr Asn
                515                 520                 525

Glu Leu Thr Lys Val Lys Tyr Val Thr Glu Gly Met Arg Lys Pro Ala
            530                 535                 540

Phe Leu Ser Gly Glu Gln Lys Lys Ala Ile Val Asp Leu Leu Phe Lys
545                 550                 555                 560

Thr Asn Arg Lys Val Thr Val Lys Gln Leu Lys Glu Asp Tyr Phe Lys
                565                 570                 575

Lys Ile Glu Cys Phe Asp Ser Val Glu Ile Ser Gly Val Glu Asp Arg
                580                 585                 590

Phe Asn Ala Ser Leu Gly Thr Tyr His Asp Leu Leu Lys Ile Ile Lys
                595                 600                 605

Asp Lys Asp Phe Leu Asp Asn Glu Glu Asn Glu Asp Ile Leu Glu Asp
            610                 615                 620

Ile Val Leu Thr Leu Thr Leu Phe Glu Asp Arg Glu Met Ile Glu Glu
625                 630                 635                 640

Arg Leu Lys Thr Tyr Ala His Leu Phe Asp Asp Lys Val Met Lys Gln
                645                 650                 655

Leu Lys Arg Arg Arg Tyr Thr Gly Trp Gly Arg Leu Ser Arg Lys Leu
                660                 665                 670

Ile Asn Gly Ile Arg Asp Lys Gln Ser Gly Lys Thr Ile Leu Asp Phe
                675                 680                 685

Leu Lys Ser Asp Gly Phe Ala Asn Arg Asn Phe Met Gln Leu Ile His
            690                 695                 700

Asp Asp Ser Leu Thr Phe Lys Glu Asp Ile Gln Lys Ala Gln Val Ser
705                 710                 715                 720

Gly Gln Gly Asp Ser Leu His Glu His Ile Ala Asn Leu Ala Gly Ser
                725                 730                 735

Pro Ala Ile Lys Lys Gly Ile Leu Gln Thr Val Lys Val Val Asp Glu
            740                 745                 750

Leu Val Lys Val Met Gly Arg His Lys Pro Glu Asn Ile Val Ile Glu
                755                 760                 765

Met Ala Arg Glu Asn Gln Thr Thr Gln Lys Gly Gln Lys Asn Ser Arg
            770                 775                 780

Glu Arg Met Lys Arg Ile Glu Glu Gly Ile Lys Glu Leu Gly Ser Gln
785                 790                 795                 800

Ile Leu Lys Glu His Pro Val Glu Asn Thr Gln Leu Gln Asn Glu Lys
                805                 810                 815

Leu Tyr Leu Tyr Tyr Leu Gln Asn Gly Arg Asp Met Tyr Val Asp Gln
                820                 825                 830

Glu Leu Asp Ile Asn Arg Leu Ser Asp Tyr Asp Val Asp His Ile Val
            835                 840                 845

Pro Gln Ser Phe Leu Lys Asp Asp Ser Ile Asp Asn Lys Val Leu Thr
            850                 855                 860

Arg Ser Asp Lys Asn Arg Gly Lys Ser Asp Asn Val Pro Ser Glu Glu
865                 870                 875                 880

Val Val Lys Lys Met Lys Asn Tyr Trp Arg Gln Leu Leu Asn Ala Lys
                885                 890                 895

Leu Ile Thr Gln Arg Lys Phe Asp Asn Leu Thr Lys Ala Glu Arg Gly
                900                 905                 910
```

```
Gly Leu Ser Glu Leu Asp Lys Ala Gly Phe Ile Lys Arg Gln Leu Val
        915                 920                 925

Glu Thr Arg Gln Ile Thr Lys His Val Ala Gln Ile Leu Asp Ser Arg
        930                 935                 940

Met Asn Thr Lys Tyr Asp Glu Asn Asp Lys Leu Ile Arg Glu Val Lys
945                 950                 955                 960

Val Ile Thr Leu Lys Ser Lys Leu Val Ser Asp Phe Arg Lys Asp Phe
        965                 970                 975

Gln Phe Tyr Lys Val Arg Glu Ile Asn Asn Tyr His His Ala His Asp
        980                 985                 990

Ala Tyr Leu Asn Ala Val Val Gly Thr Ala Leu Ile Lys Lys Tyr Pro
        995                 1000                1005

Lys Leu Glu Ser Glu Phe Val Tyr Gly Asp Tyr Lys Val Tyr Asp
    1010                1015                1020

Val Arg Lys Met Ile Ala Lys Ser Glu Gln Glu Ile Gly Lys Ala
    1025                1030                1035

Thr Ala Lys Tyr Phe Phe Tyr Ser Asn Ile Met Asn Phe Phe Lys
    1040                1045                1050

Thr Glu Ile Thr Leu Ala Asn Gly Glu Ile Arg Lys Arg Pro Leu
    1055                1060                1065

Ile Glu Thr Asn Gly Glu Thr Gly Glu Ile Val Trp Asp Lys Gly
    1070                1075                1080

Arg Asp Phe Ala Thr Val Arg Lys Val Leu Ser Met Pro Gln Val
    1085                1090                1095

Asn Ile Val Lys Lys Thr Glu Val Gln Thr Gly Gly Phe Ser Lys
    1100                1105                1110

Glu Ser Ile Leu Pro Lys Arg Asn Ser Asp Lys Leu Ile Ala Arg
    1115                1120                1125

Lys Lys Asp Trp Asp Pro Lys Lys Tyr Gly Gly Phe Asp Ser Pro
    1130                1135                1140

Thr Val Ala Tyr Ser Val Leu Val Val Ala Lys Val Glu Lys Gly
    1145                1150                1155

Lys Ser Lys Lys Leu Lys Ser Val Lys Glu Leu Leu Gly Ile Thr
    1160                1165                1170

Ile Met Glu Arg Ser Ser Phe Glu Lys Asn Pro Ile Asp Phe Leu
    1175                1180                1185

Glu Ala Lys Gly Tyr Lys Glu Val Lys Lys Asp Leu Ile Ile Lys
    1190                1195                1200

Leu Pro Lys Tyr Ser Leu Phe Glu Leu Glu Asn Gly Arg Lys Arg
    1205                1210                1215

Met Leu Ala Ser Ala Gly Glu Leu Gln Lys Gly Asn Glu Leu Ala
    1220                1225                1230

Leu Pro Ser Lys Tyr Val Asn Phe Leu Tyr Leu Ala Ser His Tyr
    1235                1240                1245

Glu Lys Leu Lys Gly Ser Pro Glu Asp Asn Glu Gln Lys Gln Leu
    1250                1255                1260

Phe Val Glu Gln His Lys His Tyr Leu Asp Glu Ile Ile Glu Gln
    1265                1270                1275

Ile Ser Glu Phe Ser Lys Arg Val Ile Leu Ala Asp Ala Asn Leu
    1280                1285                1290

Asp Lys Val Leu Ser Ala Tyr Asn Lys His Arg Asp Lys Pro Ile
    1295                1300                1305
```

```
Arg Glu Gln Ala Glu Asn Ile Ile His Leu Phe Thr Leu Thr Asn
    1310                1315                1320

Leu Gly Ala Pro Ala Ala Phe Lys Tyr Phe Asp Thr Thr Ile Asp
    1325                1330                1335

Arg Lys Arg Tyr Thr Ser Thr Lys Glu Val Leu Asp Ala Thr Leu
    1340                1345                1350

Ile His Gln Ser Ile Thr Gly Leu Tyr Glu Arg Ile Asp Leu Ser
    1355                1360                1365

Gln Leu Gly Gly Asp Gly Gly Gly Ser Arg Ser Gly Gly Tyr
    1370                1375                1380

Val Asn Ile Lys Thr Phe Thr His Pro Ala Gly Glu Gly Lys Glu
    1385                1390                1395

Val Lys Gly Met Glu Val Ser Val Pro Phe Glu Ile Tyr Ser Asn
    1400                1405                1410

Glu His Arg Ile Ala Asp Ala His Tyr Gln Thr Phe Pro Ser Glu
    1415                1420                1425

Lys Ala Ala Tyr Thr Val Val Thr Asp Ala Ala Asp Trp Arg Thr
    1430                1435                1440

Lys Asn Ala Ala Met Phe Thr Pro Thr Pro Val Ser Gly His His
    1445                1450                1455

His His His His
    1460

<210> SEQ ID NO 17
<211> LENGTH: 1334
<212> TYPE: PRT
<213> ORGANISM: Artificial Sequence
<220> FEATURE:
<223> OTHER INFORMATION: Synthetic: Cpf1-Soc

<400> SEQUENCE: 17

Pro Lys Lys Lys Arg Lys Val Met Ser Lys Leu Glu Lys Phe Thr Asn
1               5                   10                  15

Cys Tyr Ser Leu Ser Lys Thr Leu Arg Phe Lys Ala Ile Pro Val Gly
            20                  25                  30

Lys Thr Gln Glu Asn Ile Asp Asn Lys Arg Leu Leu Val Glu Asp Glu
        35                  40                  45

Lys Arg Ala Glu Asp Tyr Lys Gly Val Lys Lys Leu Leu Asp Arg Tyr
    50                  55                  60

Tyr Leu Ser Phe Ile Asn Asp Val Leu His Ser Ile Lys Leu Lys Asn
65                  70                  75                  80

Leu Asn Asn Tyr Ile Ser Leu Phe Arg Lys Lys Thr Arg Thr Glu Lys
                85                  90                  95

Glu Asn Lys Glu Leu Glu Asn Leu Glu Ile Asn Leu Arg Lys Glu Ile
            100                 105                 110

Ala Lys Ala Phe Lys Gly Asn Glu Gly Tyr Lys Ser Leu Phe Lys Lys
        115                 120                 125

Asp Ile Ile Glu Thr Ile Leu Pro Glu Phe Leu Asp Asp Lys Asp Glu
    130                 135                 140

Ile Ala Leu Val Asn Ser Phe Asn Gly Phe Thr Thr Ala Phe Thr Gly
145                 150                 155                 160

Phe Phe Asp Asn Arg Glu Asn Met Phe Ser Glu Ala Lys Ser Thr
                165                 170                 175

Ser Ile Ala Phe Arg Cys Ile Asn Glu Asn Leu Thr Arg Tyr Ile Ser
            180                 185                 190
```

```
Asn Met Asp Ile Phe Glu Lys Val Asp Ala Ile Phe Asp Lys His Glu
            195                 200                 205

Val Gln Glu Ile Lys Glu Lys Ile Leu Asn Ser Asp Tyr Asp Val Glu
        210                 215                 220

Asp Phe Phe Glu Gly Glu Phe Phe Asn Phe Val Leu Thr Gln Glu Gly
225                 230                 235                 240

Ile Asp Val Tyr Asn Ala Ile Ile Gly Gly Phe Val Thr Glu Ser Gly
                245                 250                 255

Glu Lys Ile Lys Gly Leu Asn Glu Tyr Ile Asn Leu Tyr Asn Gln Lys
            260                 265                 270

Thr Lys Gln Lys Leu Pro Lys Phe Lys Pro Leu Tyr Lys Gln Val Leu
        275                 280                 285

Ser Asp Arg Glu Ser Leu Ser Phe Tyr Gly Glu Gly Tyr Thr Ser Asp
    290                 295                 300

Glu Glu Val Glu Val Phe Arg Asn Thr Leu Asn Lys Asn Ser Glu Ile
305                 310                 315                 320

Phe Ser Ser Ile Lys Lys Leu Glu Lys Leu Phe Lys Asn Phe Asp Glu
                325                 330                 335

Tyr Ser Ser Ala Gly Ile Phe Val Lys Asn Gly Pro Ala Ile Ser Thr
            340                 345                 350

Ile Ser Lys Asp Ile Phe Gly Glu Trp Asn Val Ile Arg Asp Lys Trp
        355                 360                 365

Asn Ala Glu Tyr Asp Asp Ile His Leu Lys Lys Ala Val Val Thr
    370                 375                 380

Glu Lys Tyr Glu Asp Asp Arg Arg Lys Ser Phe Lys Lys Ile Gly Ser
385                 390                 395                 400

Phe Ser Leu Glu Gln Leu Gln Glu Tyr Ala Asp Ala Asp Leu Ser Val
                405                 410                 415

Val Glu Lys Leu Lys Glu Ile Ile Ile Gln Lys Val Asp Glu Ile Tyr
            420                 425                 430

Lys Val Tyr Gly Ser Ser Glu Lys Leu Phe Asp Ala Asp Phe Val Leu
        435                 440                 445

Glu Lys Ser Leu Lys Lys Asn Asp Ala Val Val Ala Ile Met Lys Asp
    450                 455                 460

Leu Leu Asp Ser Val Lys Ser Phe Glu Asn Tyr Ile Lys Ala Phe Phe
465                 470                 475                 480

Gly Glu Gly Lys Glu Thr Asn Arg Asp Glu Ser Phe Tyr Gly Asp Phe
                485                 490                 495

Val Leu Ala Tyr Asp Ile Leu Leu Lys Val Asp His Ile Tyr Asp Ala
            500                 505                 510

Ile Arg Asn Tyr Val Thr Gln Lys Pro Tyr Ser Lys Asp Lys Phe Lys
        515                 520                 525

Leu Tyr Phe Gln Asn Pro Gln Phe Met Gly Gly Trp Asp Lys Asp Lys
    530                 535                 540

Glu Thr Asp Tyr Arg Ala Thr Ile Leu Arg Tyr Gly Ser Lys Tyr Tyr
545                 550                 555                 560

Leu Ala Ile Met Asp Lys Lys Tyr Ala Lys Cys Leu Gln Lys Ile Asp
                565                 570                 575

Lys Asp Asp Val Asn Gly Asn Tyr Glu Lys Ile Asn Tyr Lys Leu Leu
            580                 585                 590

Pro Gly Pro Asn Lys Met Leu Pro Lys Val Phe Phe Ser Lys Lys Trp
        595                 600                 605

Met Ala Tyr Tyr Asn Pro Ser Glu Asp Ile Gln Lys Ile Tyr Lys Asn
```

-continued

```
                610                 615                 620
Gly Thr Phe Lys Lys Gly Asp Met Phe Asn Leu Asn Asp Cys His Lys
625                 630                 635                 640

Leu Ile Asp Phe Phe Lys Asp Ser Ile Ser Arg Tyr Pro Lys Trp Ser
                645                 650                 655

Asn Ala Tyr Asp Phe Asn Phe Ser Glu Thr Glu Lys Tyr Lys Asp Ile
                660                 665                 670

Ala Gly Phe Tyr Arg Glu Val Glu Glu Gln Gly Tyr Lys Val Ser Phe
                675                 680                 685

Glu Ser Ala Ser Lys Lys Glu Val Asp Lys Leu Val Glu Glu Gly Lys
690                 695                 700

Leu Tyr Met Phe Gln Ile Tyr Asn Lys Asp Phe Ser Asp Lys Ser His
705                 710                 715                 720

Gly Thr Pro Asn Leu His Thr Met Tyr Phe Lys Leu Leu Phe Asp Glu
                725                 730                 735

Asn Asn His Gly Gln Ile Arg Leu Ser Gly Gly Ala Glu Leu Phe Met
                740                 745                 750

Arg Arg Ala Ser Leu Lys Lys Glu Glu Leu Val Val His Pro Ala Asn
                755                 760                 765

Ser Pro Ile Ala Asn Lys Asn Pro Asp Asn Pro Lys Lys Thr Thr Thr
770                 775                 780

Leu Ser Tyr Asp Val Tyr Lys Asp Lys Arg Phe Ser Glu Asp Gln Tyr
785                 790                 795                 800

Glu Leu His Ile Pro Ile Ala Ile Asn Lys Cys Pro Lys Asn Ile Phe
                805                 810                 815

Lys Ile Asn Thr Glu Val Arg Val Leu Leu Lys His Asp Asp Asn Pro
                820                 825                 830

Tyr Val Ile Gly Ile Asp Arg Gly Glu Arg Asn Leu Leu Tyr Ile Val
                835                 840                 845

Val Val Asp Gly Lys Gly Asn Ile Val Glu Gln Tyr Ser Leu Asn Glu
                850                 855                 860

Ile Ile Asn Asn Phe Asn Gly Ile Arg Ile Lys Thr Asp Tyr His Ser
865                 870                 875                 880

Leu Leu Asp Lys Lys Glu Lys Glu Arg Phe Glu Ala Arg Gln Asn Trp
                885                 890                 895

Thr Ser Ile Glu Asn Ile Lys Glu Leu Lys Ala Gly Tyr Ile Ser Gln
                900                 905                 910

Val Val His Lys Ile Cys Glu Leu Val Glu Lys Tyr Asp Ala Val Ile
                915                 920                 925

Ala Leu Glu Asp Leu Asn Ser Gly Phe Lys Asn Ser Arg Val Lys Val
930                 935                 940

Glu Lys Gln Val Tyr Gln Lys Phe Glu Lys Met Leu Ile Asp Lys Leu
945                 950                 955                 960

Asn Tyr Met Val Asp Lys Lys Ser Asn Pro Cys Ala Thr Gly Gly Ala
                965                 970                 975

Leu Lys Gly Tyr Gln Ile Thr Asn Lys Phe Glu Ser Phe Lys Ser Met
                980                 985                 990

Ser Thr Gln Asn Gly Phe Ile Phe Tyr Ile Pro Ala Trp Leu Thr Ser
                995                 1000                1005

Lys Ile Asp Pro Ser Thr Gly Phe Val Asn Leu Leu Lys Thr Lys
                1010                1015                1020

Tyr Thr Ser Ile Ala Asp Ser Lys Lys Phe Ile Ser Ser Phe Asp
                1025                1030                1035
```

```
Arg Ile Met Tyr Val Pro Glu Glu Asp Leu Phe Glu Phe Ala Leu
    1040                1045                1050

Asp Tyr Lys Asn Phe Ser Arg Thr Asp Ala Asp Tyr Ile Lys Lys
    1055                1060                1065

Trp Lys Leu Tyr Ser Tyr Gly Asn Arg Ile Arg Ile Phe Arg Asn
    1070                1075                1080

Pro Lys Lys Asn Asn Val Phe Asp Trp Glu Glu Val Cys Leu Thr
    1085                1090                1095

Ser Ala Tyr Lys Glu Leu Phe Asn Lys Tyr Gly Ile Asn Tyr Gln
    1100                1105                1110

Gln Gly Asp Ile Arg Ala Leu Leu Cys Glu Gln Ser Asp Lys Ala
    1115                1120                1125

Phe Tyr Ser Ser Phe Met Ala Leu Met Ser Leu Met Leu Gln Met
    1130                1135                1140

Arg Asn Ser Ile Thr Gly Arg Thr Asp Val Asp Phe Leu Ile Ser
    1145                1150                1155

Pro Val Lys Asn Ser Asp Gly Ile Phe Tyr Asp Ser Arg Asn Tyr
    1160                1165                1170

Glu Ala Gln Glu Asn Ala Ile Leu Pro Lys Asn Ala Asp Ala Asn
    1175                1180                1185

Gly Ala Tyr Asn Ile Ala Arg Lys Val Leu Trp Ala Ile Gly Gln
    1190                1195                1200

Phe Lys Lys Ala Glu Asp Glu Lys Leu Asp Lys Val Lys Ile Ala
    1205                1210                1215

Ile Ser Asn Lys Glu Trp Leu Glu Tyr Ala Gln Thr Ser Val Lys
    1220                1225                1230

His Ala Ala Ala Gly Gly Gly Gly Ser Gly Gly Gly Gly Ser Arg
    1235                1240                1245

Ser Gly Gly Tyr Val Asn Ile Lys Thr Phe Thr His Pro Ala Gly
    1250                1255                1260

Glu Gly Lys Glu Val Lys Gly Met Glu Val Ser Val Pro Phe Glu
    1265                1270                1275

Ile Tyr Ser Asn Glu His Arg Ile Ala Asp Ala His Tyr Gln Thr
    1280                1285                1290

Phe Pro Ser Glu Lys Ala Ala Tyr Thr Thr Val Val Thr Asp Ala
    1295                1300                1305

Ala Asp Trp Arg Thr Lys Asn Ala Ala Met Phe Thr Pro Thr Pro
    1310                1315                1320

Val Ser Gly Leu Glu His His His His His His
    1325                1330

<210> SEQ ID NO 18
<211> LENGTH: 742
<212> TYPE: PRT
<213> ORGANISM: Artificial Sequence
<220> FEATURE:
<223> OTHER INFORMATION: Synthetic: Cre-Hoc

<400> SEQUENCE: 18

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
                20                  25                  30

Asp Arg Gln Ala Phe Ser Glu His Thr Trp Lys Met Leu Leu Ser Val
            35                  40                  45
```

```
Cys Arg Ser Trp Ala Ala Trp Cys Lys Leu Asn Asn Arg Lys Trp Phe
 50                  55                  60

Pro Ala Glu Pro Glu Asp Val Arg Asp Tyr Leu Tyr Leu Gln Ala
 65                  70                  75                  80

Arg Gly Leu Ala Val Lys Thr Ile Gln Gln His Leu Gly Gln Leu Asn
                     85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
            115                 120                 125

Glu Arg Ala Lys Gln Ala Leu Ala Phe Glu Arg Thr Asp Phe Asp Gln
            130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                    165                 170                 175

Ile Ala Arg Ile Arg Val Lys Asp Ile Ser Arg Thr Asp Gly Gly Arg
                180                 185                 190

Met Leu Ile His Ile Gly Arg Thr Lys Thr Leu Val Ser Thr Ala Gly
                195                 200                 205

Val Glu Lys Ala Leu Ser Leu Gly Val Thr Lys Leu Val Glu Arg Trp
            210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                    245                 250                 255

Ser Thr Arg Ala Leu Glu Gly Ile Phe Glu Ala Thr His Arg Leu Ile
                260                 265                 270

Tyr Gly Ala Lys Asp Asp Ser Gly Gln Arg Tyr Leu Ala Trp Ser Gly
                275                 280                 285

His Ser Ala Arg Val Gly Ala Ala Arg Asp Met Ala Arg Ala Gly Val
            290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                    325                 330                 335

Arg Leu Leu Glu Asp Gly Asp Gly Ser Glu Phe Gly Gly Ser Gly
                340                 345                 350

Gly Ser Gly Gly Ser Gly Gly Ser Phe Thr Val Asp Ile Thr Pro Lys
            355                 360                 365

Thr Pro Thr Gly Val Ile Asp Glu Thr Lys Gln Phe Thr Ala Thr Pro
370                 375                 380

Ser Gly Gln Thr Gly Gly Gly Thr Ile Thr Tyr Ala Trp Ser Val Asp
385                 390                 395                 400

Asn Val Pro Gln Asp Gly Ala Glu Ala Thr Phe Ser Tyr Val Leu Lys
                    405                 410                 415

Gly Pro Ala Gly Gln Lys Thr Ile Lys Val Val Ala Thr Asn Thr Leu
                420                 425                 430

Ser Glu Gly Gly Pro Glu Thr Ala Glu Ala Thr Thr Ile Thr Val
            435                 440                 445

Lys Asn Lys Thr Gln Thr Thr Leu Ala Val Thr Pro Ala Ser Pro
450                 455                 460
```

```
Ala Ala Gly Val Ile Gly Thr Pro Val Gln Phe Thr Ala Leu Ala
465                 470                 475                 480

Ser Gln Pro Asp Gly Ala Ser Ala Thr Tyr Gln Trp Tyr Val Asp Asp
            485                 490                 495

Ser Gln Val Gly Gly Glu Thr Asn Ser Thr Phe Ser Tyr Thr Pro Thr
            500                 505                 510

Thr Ser Gly Val Lys Arg Ile Lys Cys Val Ala Gln Val Thr Ala Thr
            515                 520                 525

Asp Tyr Asp Ala Leu Ser Val Thr Ser Asn Glu Val Ser Leu Thr Val
            530                 535                 540

Asn Lys Lys Thr Met Asn Pro Gln Val Thr Leu Thr Pro Pro Ser Ile
545                 550                 555                 560

Asn Val Gln Gln Asp Ala Ser Ala Thr Phe Thr Ala Asn Val Thr Gly
            565                 570                 575

Ala Pro Glu Glu Ala Gln Ile Thr Tyr Ser Trp Lys Lys Asp Ser Ser
            580                 585                 590

Pro Val Glu Gly Ser Thr Asn Val Tyr Thr Val Asp Thr Ser Ser Val
            595                 600                 605

Gly Ser Gln Thr Ile Glu Val Thr Ala Thr Val Thr Ala Ala Asp Tyr
610                 615                 620

Asn Pro Val Thr Val Thr Lys Thr Gly Asn Val Thr Val Thr Ala Lys
625                 630                 635                 640

Val Ala Pro Glu Pro Glu Gly Glu Leu Pro Tyr Val His Pro Leu Pro
            645                 650                 655

His Arg Ser Ser Ala Tyr Ile Trp Cys Gly Trp Val Met Asp Glu
            660                 665                 670

Ile Gln Lys Met Thr Glu Glu Gly Lys Asp Trp Lys Thr Asp Asp Pro
            675                 680                 685

Asp Ser Lys Tyr Tyr Leu His Arg Tyr Thr Leu Gln Lys Met Met Lys
            690                 695                 700

Asp Tyr Pro Glu Val Asp Val Gln Glu Ser Arg Asn Gly Tyr Ile Ile
705                 710                 715                 720

His Lys Thr Ala Leu Glu Thr Gly Ile Ile Tyr Thr Tyr Pro Gly Ser
            725                 730                 735

His His His His His His
            740

<210> SEQ ID NO 19
<211> LENGTH: 400
<212> TYPE: PRT
<213> ORGANISM: Artificial Sequence
<220> FEATURE:
<223> OTHER INFORMATION: Synthetic: RGD-Hoc

<400> SEQUENCE: 19

Cys Asp Cys Arg Gly Asp Cys Phe Cys Ser Ala Met Thr Phe Thr Val
1               5                   10                  15

Asp Ile Thr Pro Lys Thr Pro Thr Gly Val Ile Asp Glu Thr Lys Gln
            20                  25                  30

Phe Thr Ala Thr Pro Ser Gly Gln Thr Gly Gly Thr Ile Thr Tyr
            35                  40                  45

Ala Trp Ser Val Asp Asn Val Pro Gln Asp Gly Ala Glu Ala Thr Phe
        50                  55                  60

Ser Tyr Val Leu Lys Gly Pro Ala Gly Gln Lys Thr Ile Lys Val Val
65                  70                  75                  80
```

Ala Thr Asn Thr Leu Ser Glu Gly Gly Pro Glu Thr Ala Glu Ala Thr
            85                  90                  95

Thr Thr Ile Thr Val Lys Asn Lys Thr Gln Thr Thr Leu Ala Val
        100                 105                 110

Thr Pro Ala Ser Pro Ala Ala Gly Val Ile Gly Thr Pro Val Gln Phe
        115                 120                 125

Thr Ala Ala Leu Ala Ser Gln Pro Asp Gly Ala Ser Ala Thr Tyr Gln
        130                 135                 140

Trp Tyr Val Asp Asp Ser Gln Val Gly Gly Glu Thr Asn Ser Thr Phe
145                 150                 155                 160

Ser Tyr Thr Pro Thr Thr Ser Gly Val Lys Arg Ile Lys Cys Val Ala
                165                 170                 175

Gln Val Thr Ala Thr Asp Tyr Asp Ala Leu Ser Val Thr Ser Asn Glu
            180                 185                 190

Val Ser Leu Thr Val Asn Lys Lys Thr Met Asn Pro Gln Val Thr Leu
        195                 200                 205

Thr Pro Pro Ser Ile Asn Val Gln Gln Asp Ala Ser Ala Thr Phe Thr
        210                 215                 220

Ala Asn Val Thr Gly Ala Pro Glu Glu Ala Gln Ile Thr Tyr Ser Trp
225                 230                 235                 240

Lys Lys Asp Ser Ser Pro Val Glu Gly Ser Thr Asn Val Tyr Thr Val
                245                 250                 255

Asp Thr Ser Ser Val Gly Ser Gln Thr Ile Glu Val Thr Ala Thr Val
            260                 265                 270

Thr Ala Ala Asp Tyr Asn Pro Val Thr Val Lys Thr Gly Asn Val
        275                 280                 285

Thr Val Thr Ala Lys Val Ala Pro Glu Pro Glu Gly Glu Leu Pro Tyr
        290                 295                 300

Val His Pro Leu Pro His Arg Ser Ser Ala Tyr Ile Trp Cys Gly Trp
305                 310                 315                 320

Trp Val Met Asp Glu Ile Gln Lys Met Thr Glu Glu Gly Lys Asp Trp
                325                 330                 335

Lys Thr Asp Asp Pro Asp Ser Lys Tyr Tyr Leu His Arg Tyr Thr Leu
            340                 345                 350

Gln Lys Met Met Lys Asp Tyr Pro Glu Val Asp Val Gln Glu Ser Arg
        355                 360                 365

Asn Gly Tyr Ile Ile His Lys Thr Ala Leu Glu Thr Gly Ile Ile Tyr
        370                 375                 380

Thr Tyr Pro Lys Leu Ala Ala Ala Leu Glu His His His His His His
385                 390                 395                 400

<210> SEQ ID NO 20
<211> LENGTH: 90
<212> TYPE: PRT
<213> ORGANISM: Artificial Sequence
<220> FEATURE:
<223> OTHER INFORMATION: Synthetic: CTS-LacI-NLS

<400> SEQUENCE: 20

Met Lys Thr Tyr Gln Glu Phe Ile Ala Glu Met Lys Tyr Val Thr Leu
1               5                   10                  15

Tyr Asp Val Ala Glu Tyr Ala Gly Val Ser His Gln Thr Val Ser Arg
            20                  25                  30

Val Val Asn Gln Ala Ser His Val Ser Ala Lys Thr Arg Glu Lys Val
        35                  40                  45

```
Glu Ala Ala Met Ala Glu Leu Asn Tyr Ile Pro Asn Arg Val Ala Gln
 50                  55                  60

Gln Leu Ala Gly Lys Gln Ser Leu Leu Ile Lys Arg Pro Ala Ala Thr
 65                  70                  75                  80

Lys Lys Ala Gly Gln Ala Lys Lys Lys Lys
                 85                  90

<210> SEQ ID NO 21
<211> LENGTH: 6806
<212> TYPE: DNA
<213> ORGANISM: Artificial Sequence
<220> FEATURE:
<223> OTHER INFORMATION: Synthetic: streptomycin-resistant plasmid
      DS-SPCas

<400> SEQUENCE: 21
```

| | | | | | |
|---|---|---|---|---|---|
| accaggcacg | cctaaccgtc | agtgagattg | gatgagtgaa | cgatattgat | cgagaagagc | 60 |
| cctgcgcagc | cgctgccgtg | cctgcaggaa | gcaacggccc | ggagggtggc | gggcaggacg | 120 |
| cccgccataa | actgccaggc | atcaaattaa | gcagaaggcc | atcctgacgg | atggcctttt | 180 |
| tgcgtttcta | caaactctgc | tagcttctag | agcacagcta | acaccacgtc | gtccctatct | 240 |
| gctgccctag | gtctatgagt | ggttgctgga | taactttacg | ggcatgcata | aggctcgtat | 300 |
| gatatattca | gggagaccac | aacggtttcc | ctctacaaat | aattttgttt | aacttttact | 360 |
| agaggaggag | gcaaaatgg | ataagaaata | ctcataggc | ttagatatcg | gcacaaatag | 420 |
| cgtcggatgg | gcggtgatca | ctgatgaata | taaggttccg | tctaaaaagt | tcaaggttct | 480 |
| gggaaataca | gaccgccaca | gtatcaaaaa | aaatcttata | ggggctcttt | tatttgacag | 540 |
| tggagagaca | gcggaagcga | ctcgtctcaa | acggacagct | cgtagaaggt | atacacgtcg | 600 |
| gaagaatcgt | atttgttatc | tacaggagat | tttttcaaat | gagatggcga | aagtagatga | 660 |
| tagtttcttt | catcgacttg | aagagtcttt | tttggtggaa | gaagacaaga | agcatgaacg | 720 |
| tcatcctatt | tttggaaata | tagtagatga | agttgcttat | catgagaaat | atccaactat | 780 |
| ctatcatctg | cgaaaaaaat | ggtagattc | tactgataaa | gcggatttgc | gcttaatcta | 840 |
| tttggcctta | gcgcatatga | ttaagtttcg | tggtcatttt | ttgattgagg | gagatttaaa | 900 |
| tcctgataat | agtgatgtgg | acaaactatt | tatccagttg | gtacaaacct | acaatcaatt | 960 |
| atttgaagaa | aacccctatta | acgcaagtgg | agtagatgct | aaagcgattc | tttctgcacg | 1020 |
| attgagtaaa | tcaagacgat | tagaaaatct | cattgctcag | ctccccggtg | agaagaaaaa | 1080 |
| tggcttattt | gggaatctca | ttgctttgtc | attgggtttg | acccctaatt | ttaaatcaaa | 1140 |
| ttttgatttg | gcagaagatg | ctaaattaca | gctttcaaaa | gatacttacg | atgatgattt | 1200 |
| agataattta | ttggcgcaaa | ttggagatca | atatgctgat | ttgttttggg | cagctaagaa | 1260 |
| tttatcagat | gctatttac | tttcagatat | cctaagagta | aatactgaaa | taactaaggc | 1320 |
| tcccctatca | gcttcaatga | ttaaacgcta | cgatgaacat | catcaagact | tgactctttt | 1380 |
| aaaagcttta | gttcgacaac | aacttccaga | aaagtataaa | gaaatctttt | ttgatcaatc | 1440 |
| aaaaaacgga | tatgcaggtt | atattgatgg | gggagctagc | caagaagaat | tttataaatt | 1500 |
| tatcaaacca | atttagaaaa | aatggatgg | tactgaggaa | ttattggtga | aactaaatcg | 1560 |
| tgaagatttg | ctgcgcaagc | aacggacctt | tgacaacggc | tctattcccc | atcaaattca | 1620 |
| cttgggtgag | ctgcatgcta | ttttgagaag | acaagaagac | ttttatccat | ttttaaaga | 1680 |
| caatcgtgag | aagattgaaa | aaatcttgac | ttttcgaatt | ccttattatg | ttggtccatt | 1740 |
| ggcgcgtggc | aatagtcgtt | ttgcatggat | gactcggaag | tctgaagaaa | caattacccc | 1800 |

```
atggaatttt gaagaagttg tcgataaagg tgcttcagct caatcattta ttgaacgcat    1860
gacaaacttt gataaaaatc ttccaaatga aaaagtacta ccaaaacata gtttgcttta    1920
tgagtatttt acggtttata acgaattgac aaaggtcaaa tatgttactg aaggaatgcg    1980
aaaaccagca tttctttcag gtgaacagaa gaaagccatt gttgatttac tcttcaaaac    2040
aaatcgaaaa gtaaccgtta agcaattaaa agaagattat ttcaaaaaaa tagaatgttt    2100
tgatagtgtt gaaatttcag gagttgaaga tagatttaat gcttcattag gtacctacca    2160
tgatttgcta aaaattatta aagataaaga ttttttggat aatgaagaaa atgaagatat    2220
cttagaggat attgttttaa cattgacctt atttgaagat agggagatga ttgaggaaag    2280
acttaaaaca tatgctcacc tctttgatga taaggtgatg aaacagctta acgtcgccg    2340 ttatactggt tggggacgtt tgtctcgaaa attgattaat ggtattaggg ataagcaatc    2400
tggcaaaaca atattagatt ttttgaaatc agatggtttt gccaatcgca atttatgca    2460 gctgatccat gatgatagtt tgacatttaa agaagacatt caaaaagcac aagtgtctgg    2520
acaaggcgat agtttacatg aacatattgc aaatttagct ggtagccctg ctattaaaaa    2580 aggtattttta cagactgtaa aagttgttga tgaattggtc aaagtaatgg ggcggcataa    2640
gccagaaaat atcgttattg aaatggcacg tgaaaatcag acaactcaaa agggccagaa    2700
aaattcgcga gagcgtatga acgaatcga agaaggtatc aaagaattag gaagtcagat    2760
tcttaaagag catcctgttg aaaatactca attgcaaaat gaaaagctct atctctatta    2820
tctccaaaat ggaagagaca tgtatgtgga ccaagaatta gatattaatc gtttaagtga    2880
ttatgatgtc gatcacattg ttccacaaag tttccttaaa gacgattcaa tagacaataa    2940
ggtcttaacg cgttctgata aaaatcgtgg taaatcggat aacgttccaa gtgaagaagt    3000
agtcaaaaag atgaaaaact attggagaca acttctaaac gccaagttaa tcactcaacg    3060
taagtttgat aatttaacga aagctgaacg tggaggtttg agtgaacttg ataaagctgg    3120
ttttatcaaa cgccaattgg ttgaaactcg ccaaatcact aagcatgtgg cacaaatttt    3180
ggatagtcgc atgaatacta aatacgatga aaatgataaa cttattcgag aggttaaagt    3240
gattacctta aaatctaaat tagtttctga cttccgaaaa gatttccaat tctataaagt    3300
acgtgagatt aacaattacc atcatgccca tgatgcgtat ctaaatgccg tcgttggaac    3360
tgctttgatt aagaaatatc caaaacttga atcggagttt gtctatggtg attataaagt    3420
ttatgatgtt cgtaaaatga ttgctaagtc tgagcaagaa ataggcaaag caaccgcaaa    3480
atatttcttt tactctaata tcatgaactt cttcaaaaca gaaattacac ttgcaaatgg    3540
agagattcgc aaacgccctc taatcgaaac taatgggaa actggagaaa ttgtctggga    3600
taaagggcga gattttgcca cagtgcgcaa agtattgtcc atgccccaag tcaatattgt    3660
caagaaaaca gaagtacaga caggcggatt ctccaaggag tcaatttac caaaagaaa    3720 ttcggacaag cttattgctc gtaaaaaaga ctgggatcca aaaaaatatg gtggttttga    3780
tagtccaacg gtagcttatt cagtcctagt ggttgctaag gtggaaaaag ggaaatcgaa    3840
gaagttaaaa tccgttaaag agttactagg gatcacaatt atggaaagaa gttccttga    3900 aaaaaatccg attgactttt tagaagctaa aggatataag gaagttaaaa aagacttaat    3960
cattaaacta cctaaatata gtctttttga gttagaaaac ggtcgtaaac ggatgctggc    4020
tagtgccgga gaattacaaa aaggaaatga gctggctctg ccaagcaaat atgtgaattt    4080
tttatattta gctagtcatt atgaaaagtt gaagggtagt ccagaagata acgaacaaaa    4140
```

-continued

```
acaattgttt gtggagcagc ataagcatta tttagatgag attattgagc aaatcagtga     4200
attttctaag cgtgttattt tagcagatgc caatttagat aaagttctta gtgcatataa     4260
caaacataga gacaaaccaa tacgtgaaca agcagaaaat attattcatt tatttacgtt     4320
gacgaatctt ggagctcccg ctgcttttaa atattttgat acaacaattg atcgtaaacg     4380
atatacgtct acaaaagaag ttttagatgc cactcttatc catcaatcca tcactggtct     4440
ttatgaaaca cgcattgatt tgagtcagct aggaggtgac tgaccggctg ataaatttct     4500
ttgaatttct ccttgattat ttgttataaa tgttataaaa taatcttgtt ggaaccattc     4560
aaaacagcat agcaagttaa ataaggcta gtccgttatc aacttgaaaa agtggcaccg     4620
agtcggtgct ttttttgata cttctattct actctgactg caaaccaaaa aaacaagcgc     4680
tttcaaaacg cttgttttat cattttagg gaaattaatc tcttaatcct tttatcattc     4740
tacatttagg cgctgccatc ttgggacaat gaaaacgtta gtcatggcgc gccttgacgg     4800
ctagctcagt cctaggtaca gtgctagctt aattagtcta cgaggtttta gagctatgct     4860
gttttgaatg gtcccaaaac ctgcagacaa gcccggccgg cctaaggcga tgcccctcg     4920 acctcgatca gggaggcgtt caggacgact cacaaagaaa gccgggcaat gcccggcttt     4980
ttccacgcct cctgggctga cttcaggtgc tacatttgaa gagataaatt gcactgaaat     5040
ctagagcggt tcagtagaaa agatcaaagg atcttcttga gatcctttt ttctgcgcgt     5100 aatcttttgc cctgtaaacg aaaaaaccac ctggggaggt ggtttgatcg aaggttaagt     5160
cagttgggga actgcttaac cgtggtaact ggctttcgca gagcacagca accaaatctg     5220
tccttccagt gtagccggac tttggcgcac acttcaagag caaccgcgtg tttagctaaa     5280
caaatcctct gcgaactccc agttaccaat ggctgctgcc agtggcgttt taccgtgctt     5340
ttccgggttg gactcaagtg aacagttacc ggataaggcg cagcagtcgg gctgaacggg     5400
gagttcttgc ttacagccca gcttggagcg aacgacctac accgagccga ataccagtg      5460 tgtgagctat gagaaagcgc cacacttccc gtaaggagaa aaggcggaac aggtatccgg     5520
taaacggcag ggtcggaaca ggagagcgca agagggagcg acccgccgga aacggtgggg     5580
atctttaagt cctgtcgggt ttcgccgta ctgtcagatt catggttgag cctcacggct     5640
cccacagatg caccggaaaa gcgtctgttt atgtgaactc tggcaggagg cggagccta     5700 tggaaaaacg ccaccggcgc ggccctgctg ttttgcctca catgttagtc ccctgcttat     5760
ccacggaatc tgtgggtaac tttgtatgtg tccgcagcgc ccgccgcagt ctcacgcccg     5820
gagcgtagcg accgagtgag ctagctattt gtttattttt ctaaatacat tcaaatatgt     5880
atccgctcat gagacaataa ccctgataaa tgcttcaata atattgaaaa aggaagagta     5940
tgagggaagc ggtgatcgcc gaagtatcga ctcaactatc agaggtagtt ggcgtcatcg     6000
agcgccatct cgaaccgacg ttgctggccg tacatttgta cggctccgca gtggatggcg     6060
gcctgaagcc acacagtgat attgatttgc tggttacggt gaccgtaagg cttgatgaaa     6120
caacgcggcg agctttgatc aacgaccttt tggaaacttc ggcttcccct ggagagagcg     6180
agattctccg cgctgtagaa gtcaccattg ttgtgcacga cgacatcatt ccgtggcgtt     6240
atccagctaa gcgcgaactg caatttggag aatggcagcg caatgacatt cttgcaggta     6300
tcttcgagcc agccacgatc gacattgatc tggctatctt gctgacaaaa gcaagagaac     6360
atagcgttgc cttggtaggt ccagcggcgg aggaactctt tgatccggtt cctgaacagg     6420
atctatttga ggcgctaaat gaaaccttaa cgctatggaa ctcgccgccc gactgggctg     6480
gcgatgagcg aaatgtagtg cttacgttgt cccgcatttg gtacagcgca gtaaccggca     6540
```

```
aaatcgcgcc gaaggatgtc gctgccgact gggcaatgga gcgcctgccg gcccagtatc    6600
agcccgtcat acttgaagct agacaggctt atcttggaca agaagaagat cgcttggcct    6660
cgcgcgcaga tcagttggaa gaatttgtcc actacgtgaa aggcgagatc accaaggtag    6720
tcggcaaata atgtctaaca attcgttcaa gccgaggggc cgcaagatcc ggccacgatg    6780
acccggtcgt cggttcaggg cagggt                                        6806
```

<210> SEQ ID NO 22
<211> LENGTH: 445
<212> TYPE: PRT
<213> ORGANISM: Artificial Sequence
<220> FEATURE:
<223> OTHER INFORMATION: Synthetic: Cre-Soc

<400> SEQUENCE: 22

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
```

-continued

```
            305                 310                 315                 320
Val Met Asn Tyr Ile Arg Asn Leu Asp Ser Glu Thr Gly Ala Met Val
                325                 330                 335

Arg Leu Leu Glu Asp Gly Asp Gly Gly Ser Glu Phe Gly Gly Ser Gly
                340                 345                 350

Gly Ser Gly Gly Ser Gly Gly Ser Gly Gly Tyr Val Asn Ile Lys Thr
                355                 360                 365

Phe Thr His Pro Ala Gly Glu Gly Lys Glu Val Lys Gly Met Glu Val
                370                 375                 380

Ser Val Pro Phe Glu Ile Tyr Ser Asn Glu His Arg Ile Ala Asp Ala
385                 390                 395                 400

His Tyr Gln Thr Phe Pro Ser Glu Lys Ala Ala Tyr Thr Thr Val Val
                405                 410                 415

Thr Asp Ala Ala Asp Trp Arg Thr Lys Asn Ala Ala Met Phe Thr Pro
                420                 425                 430

Thr Pro Val Ser Gly Gly Ser His His His His His His
                435                 440                 445
```